US006872550B1

(12) United States Patent
Livey et al.

(10) Patent No.: US 6,872,550 B1
(45) Date of Patent: Mar. 29, 2005

(54) IMMUNOGENIC FORMULATION OF OSPC ANTIGEN VACCINES FOR THE PREVENTION AND TREATMENT OF LYME DISEASE AND RECOMBINANT METHODS FOR THE PREPARATION OF SUCH ANTIGENS

(75) Inventors: Ian Livey, Vienna (AT); Brian Crowe, Vienna (AT); Friedrich Dorner, Vienna (AT)

(73) Assignee: Baxter Vaccine AG, Vienna (AT)

(*) Notice: Subject to any disclaimer, the term of this patent is extended or adjusted under 35 U.S.C. 154(b) by 0 days.

(21) Appl. No.: 08/284,667

(22) PCT Filed: Apr. 29, 1994

(86) PCT No.: PCT/EP94/01365

§ 371 (c)(1), (2), (4) Date: Aug. 19, 1994

(87) PCT Pub. No.: WO94/25596

PCT Pub. Date: Nov. 10, 1994

Related U.S. Application Data

(63) Continuation-in-part of application No. 08/053,863, filed on Apr. 29, 1993, now abandoned, which is a continuation-in-part of application No. 07/903,580, filed on Jun. 25, 1992, which is a continuation-in-part of application No. 07/824,161, filed on Jan. 22, 1992, now abandoned, which is a continuation-in-part of application No. 07/727,245, filed on Jul. 11, 1991, now abandoned.

(51) Int. Cl.[7] ........................ C12N 15/09; A61K 79/02; C07K 1/00; C07H 19/00

(52) U.S. Cl. ................ 435/69.3; 424/234.1; 424/262.1; 435/69.1; 435/71.1; 530/350; 536/22.1; 536/23.7

(58) Field of Search ........................... 424/234.1, 262.1; 530/350; 536/22.1, 23.7; 435/69.1, 69.3, 71.1

(56) References Cited

U.S. PATENT DOCUMENTS

| | | | | |
|---|---|---|---|---|
| 4,601,903 A | | 7/1986 | Frasch | 424/92 |
| 4,603,112 A | | 7/1986 | Paoletti et al. | 435/235 |
| 4,767,622 A | | 8/1988 | Ristic et al. | 424/88 |
| 5,530,103 A | * | 6/1996 | Livey et al. | 530/416 |
| 5,620,862 A | * | 4/1997 | Padula et al. | 435/7.32 |

FOREIGN PATENT DOCUMENTS

| | | | | |
|---|---|---|---|---|
| DE | 3942728 | * | 5/1991 | C07K/15/04 |
| EP | 0 418 827 | | 3/1991 | A61K/39/40 |
| EP | 522560 | * | 1/1993 | |
| WO | 91/09870 | | 7/1991 | C07K/13/00 |
| WO | 9109870 | * | 7/1991 | |

OTHER PUBLICATIONS

Stevenson. GenEmbl Database Results. PID: g434658. Submitted Dec. 09, 1993. [Retrieved on Dec. 09, 1999].* 1993.*

Stevenson et al. Injection and Immunity 62(8):3568–3571, 1994 (Aug.).*

Padula et al. Injection and Immunity 61(12): 5097–5105, 1993 (Dec.).*

Anderson et al. Journal of Clinical Microbiology 28(12):2693–2699, 1990 (Dec.).*

Fung et al. Injection and Immunity 62(8): 3213–3221, 1994 (Aug.).*

Sequence Search of 5620862 OSPC 2 pages, Run date Mar. 1996.*

Livey et al Poster #370 at the Vth International Conf. on *Lyme borreliosis* Jun. 1992.*

Brockinstedt et al Journal of Immunology 151:900–906, 1993.*

Kantor, Scientific American, Sep. 1994, pp. 34–39 Disarming Lyme Disease.*

Wilske et al World Journal of Microbiology Technology 157:130–136, 1991.*

Fuchs et al. Mol. Microbiology 6:503–509, 1992.*

Wilske et al Annals of New York Academy of Sciences 539: 126–143, 1988.*

Preac–Mursic et al Infection 20:342–349 1992.*

Javris–Heipke et al Med. Microbiol. Immunol. 182:37–50, 1993.*

Wilske et al Infection & Immunity 61:2182–2191, 1993.*

Berzofsky, "Intrinsic and Extrinsic Factors in Protein Antigenic Structure", Science, vol. 29, Sep. 6, 1985, pp. 932–940.

Young et al., "Efficient Isolation of Genes by Using Antibody Probes", Proc. Natl. Acad. Sci. USA vol. 80, 1963, pp. 1194–1198.

Hopp et al., "Prediction of Protein Antigenic Determinants from Amino Acid Sequences", Proc. Natl. Acad. Sci. USA, vol. 78, 1981, pp. 3824–3828.

Wilske, "Immunodominant Borrelia Proteins for the Humoral Immune Response in Lyme Borreliosis", IV International Conference on Lyme Borreliosis, M/TU–P–38, Jun. 18–21, 1990, p. 82.

Fuchs et al., "Molecular Analysis and Expression of a *Borrelia burgdorferi* Gene Encoding a 22 kDa Protein (pC) in *Escherichia coli*,", Molecular Microbiology, 6(4): 503–509 (1992).

(Continued)

*Primary Examiner*—Rodney P Swartz
(74) *Attorney, Agent, or Firm*—Heller Ehrman White & McAuliffe

(57) ABSTRACT

A novel approach to Borrelia vaccine formulation taking into account serological, genotypic and epidemiological information by which OspC proteins from different strains of *B. burgdorferi* are grouped together. OspC antigens are chosen in order to constitute a representative sample of such groupings, so that the resulting vaccine provides the greatest cross-protectivity with the fewest number of antigens.

7 Claims, 53 Drawing Sheets

OTHER PUBLICATIONS

Simon et al., "Recombinant Outer Surface Protein A from *Borrelia burgdorferi* Induces Antibodies Protective Against Spirochetal Infection in Mice", The Journal of Infectious Disease, vol. 164, No. 1, 123–32 (1991).

Edelman, "Perspective on the Development of Vaccines Against Lyme Disease", Vaccine, vol. 9, Aug. 1991, pp. 531–532.

Fikrig et al., "*Borrelia burgdorferi* Strain 25015: characterization of Outer Surface Protein A and Vaccination Against Infection", The Journal of Immunology, 148(7): 2256–2260 (Apr. 1992).

Wilske et al., "Detection of IgM– and IgG Antibodies to *Borrelia burgdorferi* Using Different Strains as Antigen" Stanek (Ed.), Lyme Borreliosis II, Zbl. Bakt. Suppl. 18, pp. 299–309.

Morgan et al., "Approaches to the Discovery of Non–Peptide Ligands for Peptide Receptors and Peptidases", Annual Reports in Medicinal Chemistry, Chapter 26, pp. 243–252, 1989.

Laemmli, "Cleavage of Structural Proteins during the Assembly of the Head of Bacteriophage T4", Nature, vol. 227, Aug. 1970, pp. 680–685.

Wilbur et al., "Rapid Similarity Searches of Nucleic Acid and Protein Data Banks", Proc. Natl. Acad. Sci. USA, vol. 80, pp. 726–730, Feb. 1983.

Baess, "Isolation and Purification of Deoxyribonucleic Acid From Mycobacteria", Acta Path. Microbiol. Scand., Sect. B, 82: 780–784, 1974.

Kohler, et al., "Continuous Cultures of Fused Cells Secreting Antibody of Predefined Specificity", Nature, vol. 256, Aug. 1975, pp. 495–497.

Peter et al., "Polymorphism of Outer Surface Proteins of *Borrelia burgdorferi* as a Tool for Classification", Zbl. Bakjt., 277, pp. 28–33 (1992).

R. Anand, "Pulsed Field Gell Electrophoresis: a technique for fractionating large DNA molecules", Trends In Genetics, Nov. 1986, pp. 278–283.

Yang et al., "Nucleotide Sequence of the Amylase Gene from *Bacillus subtilis*" Nucleic Acids Research, vol. 11, No. 2, 1983, pp. 237–249.

Ulmanen et al., "Transcription and Translation of Foreign Genes in *Bacillus subtilis* by the Aid of a Secretion Vector", Journal of Bacteriology, vol. 162, No. 1, Apr. 1985, pp. 176–182.

Finberg et al., "The Use of Antiidiotypic Antibodies as Vaccines Against Infectious Agents", Critical Reviews in Immunology, vol. 7, Issue 4, 1987, pp. 269–284.

Wallich et al., "Evaluation of Genetic Divergence among *Borrelia burgdorferi* Isolates by Use of OspA, fla, HSP60, and HSP70 Gene Probes", Infection and Immunity, Nov. 1992, pp. 4856–4866.

Achtman et al., "A Comparison of the Variable Antigens Expressed by Clone IV–1 and Subgroup III of *Neisseria meningtidis* Serogroup A", The Journal of Infectious Diseases, 165:53–68 (1992).

LeFebvre et al., "Characterization of *Borrelia burgdorferi* Isolates by Restriction Endonuclease Analysis and DNA Hybridization", Journal of Clinical Microbiology, vol. 27, No. 4, pp. 636–639 (1989).

Postic et al., "Two Genomic Species in *Borrella burgdorferi*", Res. Microbiol., 141, pp. 465–475 (1990).

Marconi et al., "Phylogenetic Analysis of the Gene Borrelia: a Comparison of North American and European Isolates of *Borrelia burgdorferi*", Journal of Bacteriology, vol. 174, No. 1, pp. 241–244 (1992).

Stalhammer–Carlemalm et al., "Plasmid Analysis and Restriction Fragment Length Polymorphisms of Chromosomal DNA Allo9w a Distinction Between *Borrelia burgdorferi* Strains", Genetic Diversity of *Borrelia burgdorferi*, 274: 28–39 (1990).

Adam et al., Phenotypic and Genotypic Analysis of *Borrelia burgdorferi* Isolates from Various Sources, Infection and Immunity, vol. 59, No. 8, pp. 2579–2585 (1991).

Marconi et al., "Species–Specific Identification of and Distinction between *Borrelia burgdorferi* Genomic Groups by Using 16S rRNA–Directed Oligonucleotide Probes", J. of Clincal Microbiology, vol. 30, No. 3, pp. 628–632 (1992).

Welsh et al., "Genomic Fingerprinting by Arbitrarily Primed Polymerase Chain Reaction Resolves *Borrelia burgdorferi* into Three Distinct Phyletic Groups", International Journal of Systematic Bacteriology, vol. 42, No. 3, pp. 370–377 (1992).

Boerlin et al., "Population Genetic Analysis of *Borrelia burgdorferi* Isolates ty Multilocus Enzyme Electrophoresis", Infection and Immunity, vol. 60, No. 4, pp. 1677–1683 (1992).

Baranton et al., "Delineation of *Borrelia burgdorferi* Sensu Stricto, *Borrelia garinii* sp. nov., and Group VS461 Associated withy Lyme Borreliosis", Intl. J. of Systematic Bacteriology, vol. 42, No. 3, pp. 378–383 (1992).

Marconi et al., "Transcriuptional Analyses and Mapping of the ospC Gene in Lyme Disease Spirochetes", Journal of Bacteriology, vol. 175, No. 4, pp. 926–932 (1992).

Barbour et al., "Heterogeneity of Major Proteins in Lyme Disease Borreliae: A Molecular Analysis of North American and European Isolates", Journal of Infectious Diseases, vol. 153, No. 3, pp. 478–484 (1985).

Fikrig et al., "*Borrelia burgdorferi* Strain 25015: Characterization of Outer Surface Protein A and Vaccination Against Infection", Journal of Immunology, vol. 148, No. 7, pp. 2256–2260 (1992).

Wilske et al., Antigenic Variability of *Borrelia burgdorferi*, Annals New York Academy of Sciences, pp. 127–143 (1988).

Fikrig et al., "Protection of Mice Against the Lyme Disease Agent by Immunizing with Recombinant OspA", Science, vol. 250, pp. 553–556 (1990).

Howe et al., "A Single Recombinant Plasmid Expressing Two Major Outer Surface Proteins of the Lyme Disease Spirochete", Science, vol. 227, pp. 645–646 (1985).

Preac–Mursic et al., "Active Immunization with pC Protein of *Borrelia burgdorferi* Protects Gerbils against *B. burgdorferi* Infection", Infection 20, No. 6, pp. 342–349 (1992).

Bergstrom et al., Molecular Analysis of Linear Plasmid–Encoded Major Surface Proteins, OspA and OspB, of the Lyme Disease Spirochaete *Borrelia burgdorferi*, Molecular Microbiology, 3(4): 479–486 (1989).

Barbour et al., "Linear Plasmid of the Bacterium *Borrelia burgdorferi* have Covalently Closed Engs", Science, vol. 237, pp. 409–411 (1987).

Wilske et al., "Antigenic Variation and Strain Heterogeneity in Borrelia spp.", Res. Microbiol., vol. 143, pp. 583–596 (1992).

Bowie et al., "Deciphering the Message in Protein Sequences Tolerance to Amino Acid Substitutions", Science, vol. 247, pp. 1306–1310 (1990).

Kumar et al., Amino Acid Variation at a Single Residue in an Autoimmune Peptide Profoundly Affect its Properties: T–cell Activation, Major Histocompatibility Complex Binding, fand Ability to Block Experimental Alergic Encephalomyelitis, Proc. Natl. Act. Sci. USA, vol. 87, pp. 1337–1341 (1990).

Stern, "Predicting Antigenic Sites on Proteins", TIBTECH, vol. 9, pp. 163169 (1991).

van Regenmortel, "Structural and Functional Approaches to the Study of Protein Antigenicity", Immunology Today, vol. 10, No. 8, pp. 266–272 (1989).

Baess, "Isolation and Purification of Deoxyribonucleic Acid from Mycobacteria", Acta Path. Microbiol. Sand. Sect. B, 82: 780–784 (1974).

* cited by examiner

Fig. 1a

BORRELIA STRAINS USED IN THE STUDY

| STRAIN | COUNTRY | HUMAN | TICK | ANIMAL | DONOR OR REFERENCE |
|---|---|---|---|---|---|
| König | Austria | | I.ricinus | | I.Livey |
| Orth | Austria | | I.ricinus | | I.Livey |
| HB1 | Austria | Blood (Mycsitis) | | | E. Aberer |
| W | Austria | CSF | | | G. Stanek |
| H1 | Austria | Skin | | | E. Aberer |
| H10 | Austria | Skin | | | E. Aberer |
| H11 | Austria | Skin | | | E. Aberer |
| H13 | Austria | Skin | | | E. Aberer |
| H15 | Austria | Skin | | | E. Aberer |
| H2 | Austria | Skin | | | E. Aberer |
| H5 | Austria | Skin | | | E. Aberer |
| H6 | Austria | Skin | | | E. Aberer |
| H8 | Austria | Skin | | | E. Aberer |
| H9 | Austria | Skin | | | E. Aberer |
| Simon | Austria | Skin | | | E. Aberer |
| H12 | Austria | Skin (ACA) | | | E. Aberer |
| H14 | Austria | Skin (ACA) | | | E. Aberer |
| H7 | Austria | Skin (ACA) | | | E. Aberer |
| H3 | Austria | Skin (EM) | | | E. Aberer |
| H4 | Austria | Skin (EM) | | | E. Aberer |
| KL10 | Czech.Republic | | I.ricinus | | J. Jirous |
| KL11 | Czech.Republic | | I.ricinus | | J. Jirous |
| KL5 | Czech.Republic | | I.ricinus | | J. Jirous |

Fig. 1b

| STRAIN | COUNTRY | HUMAN | TICK | ANIMAL | DONOR OR REFERENCE |
|---|---|---|---|---|---|
| KL6 | Czech.Republic | | I.ricinus | | J. Hercogova |
| KC90 | Czech.Republic | Blood (Cardiac) | | | J. Hercogova |
| C78 | Czech.Republic | Blood (NB) | | | J. Hercogova |
| M57 | Czech.Republic | CSF | | | J. Hercogova |
| E180 | Czech.Republic | Skin (EM) | | | J. Hercogova |
| E51 | Czech.Republic | Skin (EM) | | | J. Hercogova |
| E61 | Czech.Republic | Skin (EM) | | | J. Jirous |
| DK6 | Denmark | CSF | | | Theisen et al. 1993 J.Clin.Microiol. 31:2570 |
| DK7 | Denmark | Skin (ACA) | | | Theisen et al. 1993 J.Clin.Microiol. 31:2571 |
| DK26 | Denmark | Skin (EM) | | | Theisen et al. 1993 J.Clin.Microiol. 31:2572 |
| 153 | France | | I.ricinus | | G. Baranton |
| 20047 | France | | I.ricinus | | G. Baranton |
| IP1 | France | CSF | | | G. Baranton |
| IP2 | France | CSF | | | G. Baranton |
| ZS7 | Germany | | I.ricinus | | DSM (5527) |
| PBI | Germany | CSF | | | Jauris-Heipke et al. 1993 Med.Microbiol. Immunol. 182:37 |
| P1H | Germany | Skin (ACA) | | | V. Preac-Mursic |
| PKO | Germany | Skin (EM) | | | J. Jirous |
| MK5 | Hungary | | I.ricinus | | A. Lakos |
| MK6 | Hungary | | I.ricinus | | A. Lakos |
| BITS | Italy | | I.ricinus | | M. Cinco |
| Gaultier | Italy | Skin (EM) | | | M. Cinco |
| J1 | Japan | | I.persulcatus | | G. Baranton |

Fig. 1c

| STRAIN | COUNTRY | HUMAN | TICK | ANIMAL | DONOR OR REFERENCE |
|---|---|---|---|---|---|
| Lithuania | Lithuania | | I.ricinus | | J. Bunikis |
| IP21 | Russia | | I.persulcatus | | E.L. Kornberg |
| IP90 | Russia | | I.persulcatus | | S. Bergstrom |
| IR210 | Russia | | I.ricinus | | E.L. Kornberg |
| JSB | Slovenia | Skin | | | E. Ruzic |
| 871104 | Sweden | CSF | | | J. Jirous |
| NBS16 | Sweden | Neuroborrelios | | | S. Bergstrom |
| NBS1ab | Sweden | Neuroborrelios | | | S. Bergstrom |
| NBS23a | Sweden | Neuroborrelios | | | S. Bergstrom |
| NBS23b | Sweden | Neuroborrelios | | | S. Bergstrom |
| ACA1 | Sweden | Skin (ACA) | | | S. Bergstrom |
| IRS | Switzerland | | I.ricinus | | ATCC (35211) |
| VS102 | Switzerland | | I.ricinus | | O. Peter |
| VS116 | Switzerland | | I.ricinus | | O. Peter |
| VS185 | Switzerland | | I.ricinus | | O. Peter |
| VS215 | Switzerland | | I.ricinus | | O. Peter |
| VS219 | Switzerland | | I.ricinus | | O. Peter |
| VS461 | Switzerland | | I.ricinus | | G. Baranton |
| VSBM | Switzerland | CSF | | | O. Peter |
| VSBP | Switzerland | CSF | | | O. Peter |
| VSDA | Switzerland | CSF | | | O. Peter |

Fig. 1d

| STRAIN | COUNTRY | HUMAN | TICK | ANIMAL | DONOR OR REFERENCE |
|---|---|---|---|---|---|
| 26815 | United States | | | Chipmunk | J.F. Anderson |
| 19857 | United States | | | Rabbit | J.F. Anderson |
| 26816 | United States | | | Vole | J.F. Anderson |
| 21347 | United States | | | White-footet mouse | J.F. Anderson |
| 2591 | United States | | | White-footet mouse | Padula et al. 1993 Infect.Immun. 61:5097 |
| 25015 | United States | | I.dammini | | J.F. Anderson |
| 27579 | United States | | I.dammini | | J.F. Anderson |
| 27985 | United States | | I.dammini | | J.F. Anderson |
| 28354 | United States | | I.dammini | | J.F. Anderson |
| 28691 | United States | | I.dammini | | J.F. Anderson |
| B31 | United States | | I.dammini | | ATCC (35210) |
| 19952 | United States | | I.dentatus | | J.F. Anderson |
| Son 188 | United States | | I.pacificus | | J. Jirous |
| HB4 | United States | Blood | | | J. Jirous |
| 297 | United States | CSF | | | J. Jirous |

Fig. 2

Addresses of Strain Contributors

| Strain Contributor | Address | Strain Contributor | Address |
|---|---|---|---|
| Dr. G. Stanek | University of Vienna<br>Hygiene Institute<br>Kinderspital Gasse 15<br>1095 VIENNA<br>Austria | J. Bunikis | Vilnius University<br>Lab of Zosmoses<br>P O Box 472<br>232007 VILIUS 7<br>Lithmgmiam<br>USS |
| ATCC | American Type Culture<br>Collection<br>12301 Parklawn Drive<br>Rockville; MARYLAND<br>20852-1776 | Dr. G. Baranton | Pasteur Institute<br>28 rue du Dr. Roux<br>75724 Ced 15 PARIS<br>France |
| Dr. J. Jirous | Institute of Hygiene and<br>Epidemiology<br>Svobarova 48<br>100 42 PRAGUE 10<br>Czech. Republic | Docent S. Bergström | University of Umeå<br>Department of<br>Microbiology<br>901 87 UMEA<br>Sweden |
| Dr. M. Cinco | University of Trieste<br>Institute of Microbiology<br>Via Flemin 22<br>TRIESTE<br>Italy | Dr. J.F. Anderson | Danderyd Hospital<br>Department of Infections<br>Diseses<br>182 88 DANDERY<br>Sweden |
| Dr. V. Preac-Mursic | Pettenkofer Institute<br>Pettenkoferstr. 9a<br>8000 München 2<br>Fed.Rep. of Germany | Dr. E. Aberer | II Department of<br>Dermatology<br>Alserstraße 4<br>1090 VIENNA<br>Austria |
| Prof. G. Stierstedt | Danderyd Hospital<br>Department of<br>Infectious Diseases<br>182 88 DANDERY<br>Sweden | Dr. J. Hercogová | Dermatovenerological<br>Clinic<br>Charles University<br>Bodimova 2<br>180 81 PRAGUE 8<br>Czech. Republic |
| Dr. R. Ruzic | Institut for Microbiology<br>Zaleska 4<br>61105 LJUBLJANA<br>Slovenia | Prof. E. Korenberg | The Gamaleya Institute<br>Vector Laboratory<br>Gemeleya Strasse 18<br>123098 Moscow<br>USSR |
| Dr. A. Lakos | Central Hospital<br>Infect Dis<br>P O Box 29<br>1450 BUDAPEST<br>Hungary | Dr. O. Peter | Institut Central des<br>Hospitaux Val<br>1950 Sion<br>Switzerland |

Fig. 3

BBM SERIES OF MONOCLONAL ANTIBODIES USED IN THE CMAT ANALYSIS

| BBM Monoclonal Antibody | Antigen Specificity | M.W. of Homologous Antigen | Homologous Strain | Isotype |
|---|---|---|---|---|
| BBM 33 | E 90 | 90.5 | W/B31 | IgG1 |
| BBM 26 | E 60 | 60.4 | W/B31 | IgG1 |
| BBM 20 | E 60 | 60.4 | W/B31 | IgG1 |
| BBM 21 | E 59 | 58.7 | W/B31 | IgG1 |
| BBM 14 | Fla | 42.2 | W | IgG1 |
| BBM 17 | E 43 | 43.1 | W | IgG1 |
| BBM 16 | E 43 | 43.1 | W | IgG1 |
| BBM 1 | E 29 | 29 | B31 | IgG1 |
| BBM 12 | E 22 | 22 | B31 | IgG1 |
| BBM 10 | E 20 | 20 | B31 | IgG1 |
| BBM 32 | E 18 | 18 | W/B31 | IgG1 |
| BBM 11 | E 10 | <15.0 | B31 | IgG3 |

Fig. 4

COMMON ANTIGEN SCORES USED IN THE CLUSTER ANALYSIS

| CMAT | Rep. Strain | E 90 | E 60 | E 50 | E 41 | E 43 | E 29 | E 19 | E 17 + E 1 | E 10 | Subgroup | Cluster | CMAT |
|---|---|---|---|---|---|---|---|---|---|---|---|---|---|
| 1 | IRS | | 3 | 2 | | 2 | | 2 | 2 | | 1 | 1 | 1 |
| 2 | ZS7 | 2 | 3 | 2 | 1 | 3 | 1 | 2 | 2 | 2 | 1 | 1 | 2 |
| 3 | SON 188 | | 3 | 3 | 1 | 4 | 2 | 1 | 2 | 2 | 1 | 2 | 3 |
| 4 | B31 | 2 | 3 | 3 | 1 | 4 | 2 | 2 | 2 | 2 | 1 | 2 | 4 |
| 5 | 21347 | 2 | 3 | 3 | 1 | 4 | 1 | 1 | 2 | 2 | 1 | 2 | 5 |
| 6 | 26815 | 2 | 3 | 3 | 1 | 4 | 1 | 2 | 2 | 2 | 1 | 2 | 6 |
| 7 | 28354 | 2 | 3 | 3 | 1 | 4 | 3 | 1 | 2 | 2 | 1 | 2 | 7 |
| 8 | 20047 | 2 | 5 | 4 | 1 | 4 | | 1 | 1 | | 2 | 1 | 8 |
| 9 | IP90 | 2 | 5 | 4 | 1 | 4 | 4 | 2 | 1 | | 2 | 1 | 9 |
| 10 | NBS16 | 2 | 6 | 4 | 1 | 4 | | 4 | | | 2 | 1 | 10 |
| 11 | 20515 | 1 | 1 | 4 | 1 | 4 | | 1 | | | 2 | 2 | 11 |
| 12 | JI | 1 | 2 | 2 | 1 | 5 | | 1 | | | 3 | 1 | 12 |
| 13 | ORTH | 3 | 2 | 1 | 1 | 4 | | 1 | | | 3 | 2 | 13 |
| 14 | ACA1 | 3 | 2 | | 1 | 6 | | 4 | | | 3 | 2 | 14 |
| 15 | 19857 | 1 | | 4 | 1 | 6 | | 3 | | 2 | 4 | 1 | 15 |
| 16 | 19952 | 1 | 5 | 3 | 1 | 6 | | 4 | 1 | 2 | 4 | 1 | 16 |
| 17 | 871104 | 4 | 5 | 3 | 1 | 6 | | 4 | | | 4 | 2 | 17 |
| 18 | KL5 | 5 | 5 | 5 | 1 | 6 | | 4 | 1 | | 4 | 2 | 18 |
| 19 | LITH | 5 | 6 | 5 | 1 | 6 | | 4 | | | 4 | 2 | 19 |
| 20 | H13 | 4 | 6 | 5 | 1 | 6 | | 4 | 1 | | 4 | 2 | 20 |
| 21 | 153 | 5 | 2 | 1 | 1 | 6 | | 4 | | | 4 | 2 | 21 |
| 22 | H4 | 6 | | 1 | 1 | 6 | | 4 | | | 4 | 2 | 22 |
| 23 | NBS23 | 4 | 5 | | 1 | 6 | | 1 | | | 4 | 3 | 23 |

POPULATION STRUCTURE OF LYME DISEASE BORRELIA

Fig. 6

OspC Serovar Monoclonal Antibody Reaction Patterns

| Serovar | BBM22 | BBM24 | BBM35 | BBM36 | BBM39 | BBM40 | BBM41 | BBM43 | BBM44 | BBM46 | BBM47 | BBM49 | BBM77 | Type Strain |
|---|---|---|---|---|---|---|---|---|---|---|---|---|---|---|
| 1 | + | | | | | | | | | | | | | VS215 |
| 2 | | +/- | | | | +/- | | | | | | | | B31 |
| 3 | + | | + | | | | | + | | | + | | | H5 |
| 4 | | + | | + | + | + | | | | | | | | ORTH |
| 5 | + | | + | | | + | | + | | | | | | H2 |
| 6 | + | | + | + | | + | | + | | | | | | H15 |
| 7 | + | | | + | | + | | + | + | | | | | PKO |
| 8 | | | + | | | + | | + | | | + | + | | E61 |
| 9 | | | | | | + | | + | | | + | + | | Simon |
| 10 | | | | | | + | | | | | + | | | M57 |
| 11 | | + | | | | | | | | | + | | + | W |
| 12 | | | | | | | + | | + | | | | | KL10 |
| 13 | | | | | | | | | + | | | | | NBS1ab |
| 14 | | | | | | | | | + | | + | | | 20047 |
| 15 | | | | + | | | | + | | | + | | | NBS23a |
| 16 | | | | | | | | | | + | + | | | VS461 |

\+  Strong Reaction
+/-  Sometimes a Weak Reaction

Fig. 7

Restriction Fragment Lenght Polymorphism (RFLP) among ospC genes

| RFLP Type | Type Strain | Undigested | Dpn11 | Dde1 | Dra1 |
|---|---|---|---|---|---|
| 1 | ZS7 | 639 | 103, 189, 347 | 258, 381 | 120, 159, 360 |
| 2 | B31 | 636 | 148, 204, 284 | 255, 381 | 156, 480 |
| 3 | 25015 | 639 | 287, 352 | 045, 141, 453 | 104, 535 |
| 4 | 297 | 636 | 010, 149, 206, 271 | 120, 135, 381 | 156, 480 |
| 5 | H9 | 642 | 284, 358 | 255, 387 | 052, 104, 486 |
| 6 | J1 | 639 | 284, 355 | 639 | 052, 104, 483 |
| 7 | ORTH | 642 | 287, 355 | 120, 135, 387 | 642 |
| 8 | ACA1 | 639 | 206, 433 | 032, 223, 348 | 052, 104, 483 |
| 9 | JSB | 642 | 027, 149, 175, 287 | 165, 222, 255 | 040, 116, 213, 273 |
| 10 | E61 | 639 | 287, 352 | 255, 384 | 156, 483 |
| 11 | Simon | 642 | 149, 206, 287 | 089, 553 | 156, 486 |
| 12 | M57 | 633 | 089, 176, 179, 189 | 253, 378 | 154, 222, 255 |
| 13 | W | 636 | 065, 086, 117, 179, 189 | 636 | 156, 480 |
| 14 | KL10 | 639 | 122, 235, 282 | 114, 261, 264 | 155, 484 |
| 15 | NBS1ab | 639 | 235, 404 | 114, 120, 141, 264 | 156, 483 |
| 16 | IP90 | 639 | 115, 120, 404 | 114, 120, 141, 264 | 156, 483 |
| 17 | BITS | 639 | 101, 115, 120, 303 | 639 | 052, 104, 483 |
| 18 | PBI | 627 | 627 | 027, 228, 372 | 052, 104, 471 |
| 19 | KL11 | 627 | 115, 512 | 005, 027, 223, 372 | 156, 471 |
| 20 | 20047 | 633 | 189, 444 | 261, 372 | 025, 104, 477 |
| 21 | NBS23a | 639 | 215, 424 | 162, 213, 262 | 154, 483 |
| 22 | VS461 | 633 | 149, 206, 278 | 135, 498 | 104, 529 |
| 23 | VSDA | 630 | 119, 160, 355 | 255, 375 | 052, 104, 474 |
| 24 | 2591 | 642 | 281, 361 | 219, 423 | 156, 228, 258 |
| 25 | H13 | 627 | 189, 438 | 024, 213, 390 | 156, 471 |
| 26 | Son188 | 642 | 110, 240, 290 | 205, 437 | 152, 490 |
| 27 | 28691 | 633 | 633 | 255, 378 | 052, 104, 477 |
| 28 | 21347 | 633 | 290, 343 | 108, 132, 393 | 145, 488 |
| 29 | 26815 | 642 | 642 | 083, 559 | 095, 547 |
| 30 | 28354 | 642 | 642 | 245, 397 | 095, 547 |
| 31 | 19857 | 639 | 281, 358 | 275, 382 | 298, 341 |
| 32 | 19952 | 639 | 67, 197, 375 | 260, 373 | 639 |
| 33 | NBS16 | 633 | 090, 195, 348 | 240, 393 | 150, 483 |
| 34 | 153 | 642 | 267, 375 | 120, 120, 402 | 160, 482 |
| 35 | VS116 | 633 | 155, 200, 278 | 633 | 633 |

Fig. 8-1

| | | | |
|---|---|---|---|
| 2591 | TGTAATAATTCAGGGAAAGATGGGAAT----ACATCTGCAAATTCTGCTGA |
| B31 | TGTAATAATTCAGGGAAAGATGGGAAT----ACATCTGCAAATTCTGCTGA |
| 25015 | TGTAATAATTCAGGAAAAGATGGGAACGCTGCATCTACTACTCCTGCTGA |
| ZS7 | TGTAATAATTCAGGGAAAAGATGGGAAT---ACATCTGCAAATTCTGCTGA |
| 297 | TGTAATAATTCAGGGAAAGATGGGAAT----ACATCTGCAAATTCTGCTGA |
| SIMON | TGTAATAATTCAGGAAAAGGTGGGGATTCTACATCTACTACTCCTGCTGA |
| E61 | TGTAATAATTCAGGGAAAGGTGGGGATTCTGCATCTACTACTCCTGCTGA |
| ORTH | TGTAATAATTCAGGGAAAGGTGGAGATTCTGCATCTACTACTCCTGCTGA |
| ACA1 | TGTAATAATTCAGGGAAAGGTGGGGATTCTGCATCTACTACTCCTGCTGA |
| H9 | TGTAATAATTCAGGGAAAGGTGGAGATTCTGCATCTACTACTCCTGCTGA |
| J1 | TGTAATAATTCAGGGAAAGGTGGGGATTCTGCATCTACTACTCCTGCTGA |
| JSB | TGTAATAATTCAGGGAAAGGTGGGGATTCTGCATCTACTACTAATCCTGCTGA |
| VS461 | TGTAATAATTCAGG------TGGGGATACCGCATCTACTACTAATCCTG----A |
| M57 | TGTAATAATTCAGG------TGGGGATACTGCATCTACTACTAATCCTG----A |
| W | TGTAATAATTCAGG------TGGGGATACTGCATCTACTACTAATCCTG----A |
| VSDA | TGTAATAATTCAGG------TGGGGATACTGCATCTACTACTAATCCTG----A |
| NBS23a | TGTAATAATTCAGG------TGGGGATACTGCATCTACTACTAATCCTG----A |
| 20047 | TGTAATAATTCAGG------TGGGGATACTGCATCTACTACTAATCCTG----A |
| KL10 | TGTAATAATTCAGG------TGGGGATACCGCATCTACTACTAATCCTG----A |
| IP90 | TGTAATAATTCAGG------TGGGGATACCGCATCTACTACTAATCCTG----A |
| NBS1AB | TGTAATAATTCAGG------TGGAGATTCTGCATGTGCATCTACTACTAATCCTG----A |
| BITS | TGTAATAATTCAGG------TGGGGATACTGCATCTACTACTAATCCTG----A |
| KL11 | TGTAATAATTCAGG------TGGGGATACTGCATCTACTACTAATCCTG----A |
| PBI | TGTAATAATTCAGG------TGGGGATTCTGCATCTACTACTAATCCTG----A |
| | ************** *** **** * ***** * ***** * |

Fig. 8-2

| | |
|---|---|
| 2591 | TGAGTCTGTTAAAGGGCCTAATCTTACAGAAATAAGTAAAAAATTACAG |
| B31 | TGAGTCTGTTAAAGGGCCTAATCTTACAGAAATAAGTAAAAAATTACGG |
| 25015 | TGAGTCTGTTAAAGGGCCTAATCTTACAGAAATAAGTAAAAAATTACGG |
| ZS7 | TGAGTCTGTTAAAGGGCCTAATCTTACAGAAATAAGTAAAAAATTACGG |
| 297 | TGAGTCTGTTAAAGGGCCTAATCTTACAGAAATAAGTAAAAAATTACAG |
| SIMON | CGAGTCTGCTAAAGGGCCTAATCTTACAGAAATAAGTAAAAAATTACAA |
| E61 | CGAGTCTGCTAAAGGGCCTAATCTTACAGAAATAAGTAAAAAATTACAG |
| ORTH | CGAGTCTGCGAAAGGACCTAATCTTACAGAAATAAGCAAAAAATTACAG |
| ACA1 | CGAGTCTGCGAAAGGGCCTAATCTTACAGAAATAAGCAAAAAATTACAG |
| H9 | CGAGTCTGCGAAAGGGCCTAATCTTACAGAAATAAGCAAAAAATTACAG |
| J1 | CGAGTCTGCGAAAGGGCCTAATCTTACAGAAATAAGCAAAAAATTACAG |
| JSB | CGAGTCTGCGAAAGGGCCTAATCTTACAGAAATAAGCAAAAAATTACAG |
| VS461 | CGAGTCTGCGAAAGGACCTAATCTTACAGAAATAAGCAAAAAATTACAG |
| M57 | TGAGTCTGCGAAAGGACCTAATCTTACAGAGTAAGCAAAAAATTACAG |
| W | TGAGTCTGCAAAAGGACCTAATCTTATAGAAATAAGCAAAAAATTACAG |
| VSDA | TGAATCTGCGAAAGGACCTGATCTTACAGTAATAAGCAAAAAATTACAG |
| NBS23a | TGAGTCTGCGAAAGGACCTAATCTTACAGAAATAAGCAAAAAATTACAG |
| 20047 | TGAGTCTGTTAAGGGGACCTAATCTTACAGAAATAAGCAAAAAATTACAG |
| KL10 | TGAGTCTGCAAAAGGACCTAATCTTATAGAAATAAGCAAAAAATTACAG |
| IP90 | TGAGTCTGCGAAAGGACCTGATCTTACAGTAATAAGCAAAAAATTACAG |
| NBS1AB | TGAGTCTGCAAAAGGACCTAATCTTATAGAAATAAGCAAAAAATTACAG |
| BITS | TGAGTCTGCAAAAGGACCTAATCTTACAGTAATAAGCAAAAAATTACAG |
| KL11 | TGAATCTGCGAAAGGACCTGATCTTACAGTAATAAGCAAAAAATTACAG |
| PBI | TGAGTCTGCAAAAGGACCTAATCTTACCGTAATAAGCAAAAAATTACAG |
| | * * **** ** ***** ** ** ******** * ***** * ******* |

Fig. 8-3

| | |
|---|---|
| 2591 | AATCTAACGCAGTTGTTCTCGCCGTGAAAGAAGTTGAAACTCTGCTTGCA |
| B31 | ATTCTAATGCGGTTTTACTTGCTAGCTGTGTGAAAGAGAGTTGAAGCGTTGCTGTCA |
| 25015 | ATTCTAATACGGTTGTGCTAGCTGTGTGAAAGAAGTTGAAGCTTTGCTACA |
| ZS7 | ATTCTAATGCGGTTTTACTTGCTAGCTGTGAAAGAGAGTTGAAGCGTTGCTGTCA |
| 297 | AATCTAACGCAGTTGTTCTCGCCGTGAAAGAAGTTGAAACTTTGCTTACA |
| SIMON | ATTCTAATGCATTGTACTTGCTGTTAAAGAAGTTGAGACTTTGGTTGCA |
| E61 | ATTCTAATGCATTGTACTTGCTGTTAAAGAAGTTGAGACTTTGGTTGCA |
| ORTH | ATTCTAATGCATTGTACTGGCTGTTAAAGAAGTTGAGACTTTGGTTCA |
| ACA1 | ATTCTAATGCATTTGTACTTGCTGTTAAAGAAGTTGAGACTTTGGTTCA |
| H9 | ATTCTAATGCATTTGTACTTGCTGTTAAAGAAGTTGAGACTTTGGTTTCA |
| J1 | ATTCTAATGCATTTGTACTTGCTGTTAAAGAAGTTGAGACTTTGGTTCT |
| JSB | ATTCTAATGCATTGTACTTGCTGTTAAAGAAGTTGAGACTTTGGTTTA |
| VS461 | ATTCCAATGCAGTTGTACTAGCTGTGAAAGAAGTTGAGGCTTTGCTTTCA |
| M57 | ATTCTAATGCATTGTACTAGCTGTGAAAGAAGTTGAGGCTTTGCTTTCA |
| W | ATTCTAATGCATTTGTACTGGCTGTGAAAGAAGTTGAGGCTTTGATCTCA |
| VSDA | ATTCTAATGCATTGTACTGGCTGTGAAAGAAGTTGAGGCTTTGATCTCA |
| NBS23a | ATTCTAATGCATTGTACTGGCTGTGAAAGAAGTTGAGGCTTTGATTCA |
| 20047 | ATTCTAATGCATTGTACTCGCCGTTAAAGAAGTTGAGGCTTTGATCTCA |
| KL10 | ATTCTAATGCATTGTACTGGCTGTGAAAGAAGTTGAGGCTTTGCTTTCA |
| IP90 | ATTCTAATGCATTGTACTGGCTGTGAAAGAAGTTGAGGCTTTGCTTTCA |
| NBS1AB | ATTCTAATGCATTGTACTGGCTGTGAAAGAAGTTGAGGCTTTGCTTTCA |
| BITS | ATTCTAATGCATTGTACTGGTTGTGAAAGAAGTTGAGGCTTTGCTTTCA |
| KL11 | ATTCTAATGCAGTTGTACTGGCTGTGAAAGAAGTTGAGGCTTTGCTTTCA |
| PBI | ATTCTAATGCATTTTACTGGCTGTGAAAGAAGTTGAGGCTTTGCTTTCA |
| | * *** ** * *** ** ** ***** ***** * |

Fig. 8-4

| | |
|---|---|
| 2591 | TCTATAGATGAAGTTGCTAAGAAAGCTATTGGGAATTTGATAGCCCAAA |
| B31 | TCTATAGATGAAATTGCTGCTAAAGCTATTGGTAAAGCTATTACACCAAA |
| 25015 | TCTATAGATGAACTTGCTACTAAAGCTATTGGTAAAAAATACACCAAAA |
| ZS7 | TCTATAGATGAGCTTGCTA---AAGCTATTGGTAAAAAATAAAAAACGA |
| 297 | TCTATAGATGAGCTTGCTA---AAGCTATTGGTAAAAAATAAAAAACGA |
| SIMON | TCTATAGATGAACTTGCTACTAAAGCTATTGGTAAAAAATAAAAAATGA |
| E61 | TCTATAGATGAACTTGCTACTAAAGCTATTGGTAAAAAATAAAAAATGA |
| ORTH | TCTATAGATGAACTTGCTACTAAAGCTATTGGTAAAAAATACAACAAAA |
| ACA1 | TCTATAGATGAACTTGCCAATAAAGCTATTGGTAAAAAATACAACAAAA |
| H9 | TCTATAGATGAACTTGCTCAAGCTATTGGTAAAAAATACAA---AA |
| J1 | TCTATAGATGAACTTGCTA---AAGCTATTGGTCAAAAATACAA---AA |
| JSB | TCTATAGATGAACTTGCTA---AAACTATTGGTCAAAAATAGACAATAA |
| VS461 | TCTATAGATGAACTTGCTA---AAATAAAGCTATTGGTAAAGTAATACATCAAAA |
| M57 | TCTATAGATGAACTTGCTAATAAGCTATTGGTAAAGTAATACATCAAAA |
| W | TCTATAGATGAACTTGCTAATAAGCTATTGGTAAAAAATAAATCAAAA |
| VSDA | TCTGTAGATGAACTTGCCA---AAGCTATTGGTAAAAGATACATCAAAA |
| NBS23a | TCTGTAGATGAACTTGCTA---AGGCTATTGGTAAAAAATAGATAACAA |
| 20047 | TCTATAGATGAACTTGCTA---AAGCTATTGGTCAAAGAATACAACAAA |
| KL10 | TCTATAGATGAACTTGCTA---AAGGTATTGGTAAAAAATAGATCAAAA |
| IP90 | TCTATAGATGAACTTGCTA---AAGCTATTGGTCAAAAATAGATCAAAA |
| NBS1AB | TCTATAGATGAACTTGCTA---AAGCTATTGGTCAAAAATAGATCAAAA |
| BITS | TCTATAGATGAACTTGCTA---AAGCTATTGGTCAAAAATAGATCAAAA |
| KL11 | TCTATAGATGAACTTTCTA---AAGCTATTGGTAAAAAATAAGAAATGA |
| PBI | TCTATAGATGAACTTTCTA---AAGCTATTGGTAAAAAATAAAAAATGA |

Fig. 8-5

```
2591    T----GGTTTAAATGCCGGTGC----TAATCAAAACGGATCATTGTTAGCGG
B31     TAATGGTTTGGATACCGAAAA----TAATCACAATGGATCATTGTTAGCGG
25015   TAATGGTTTGGATACCGAAAA----TAATCACAATGGATCATTGTTAGCGG
ZS7     TGTTAGTTTAGGTGATGAAGC----AAATCACAACGAGTCATTGTTAGCAG
297     TGTTAGTTTAGATAATGAGGC----AGATCACAACGGATCATTAATATCAG
SIMON   TGGCACTTTAGAGAACGAAGC----AAATCACAACGGATCATTGTTAGCGG
E61     TGGCACTTTAGATAACGAAGC----AAATCACAACGGATCATTGTTAGCAG
ORTH    TAATGGTTTAGGCGCCAATGC----GGATAAAAACGGATCATTGTTAGCAG
ACA1    T----GGTTTAGGCGCCGAAGC----GAATCGCAACGAATCATTGTTGGCCG
H9      CAATGGTTTGACTGCCGAACA----GAATCAAAACGGATCATTATTAGCAG
J1      CAATGGTTTGAGTGCCGAACA----GAATCAAAACGGATCATTATTAGCAG
JSB     TAATGGTTTAGCTGCTGCTTTAAA----TAATCAGAATGGATCGTTGTTAGCAG
VS461   ----TGGTTTGGGTAACGAAGC----GGGTCAAAACGGATCATTGTTAGCAG
M57     TAATGGTTTAAATGCTAATGC----TAATCACAACGGATCATTGTTAGCAG
W       T----GGTTTAGATGCTGATGC----AAATCAAAACGGATCATTGTTAGCAG
VSDA    TAATGGTTTAGATACTCTGTC----AAATCAAAACGGATCACACTTCATTGTTAGCAG
NBS23a  TACTGGTTTAAGTGCTAATCA----GAATCATAACAGCGCATTGTTAGCAG
20047   T----GGTTTAGTTGCTGATGC----GGGTCACAACAGCACACCTCGTTGTTAGCAG
KL10    TAGTGGTTTAGCTGCTGCTACTCAGAATAAAAACACCTCGTTGTTAGCAG
IP90    TAATGGTTTAGCTGCTGCTACTCAGGATAAAAACACCTCATTGTTAGCAG
NBS1AB  TAATGGTTTAGCTGCTGCTACTCAGGATAAAAACACCTCATTGTTAGCAG
BITS    TAATGGTTTAGCTGCTGTGAAGC----GAATTTTAACACCTCATTGTTAGCAG
KL11    TGGTACTTTAGATAACGAAGC----AAATCGAAACGAATCATTGATAGCAG
PBI     TGGTACTTTAGATAACGAAGC----AAATCGAAACGAATCATTGATAGCAG
                ***                    *        **  *  ** *
```

Fig. 8-6

```
2591     GAGCCTACGTAATATCAACCCTAATAGCAGAAAAATTAGATGGATTGA--
B31      GAGCTTATGCAATATCAACCCTAATAAAACAATAAAATTAGATGGATTGA--
25015    GGGCCTATGCAATATCAACGCTAATAACACAAAAGTTAGGTGGATTGA--
ZS7      GAGCTTATACAATATCAACCTTAATAACACAAAATTAAGTAAATTAA--
297      GAGCATATTTAATTTCAACATTAATAACAAAAAAATAAGTGCAATAA--
SIMON    GAGCTTATGCAATATCAAATCTAATAAAAACAAAAATTAGATGGATTGA--
E61      GAGCCTATGCAATATCAACTCTAATAACACAAAATTAAGTGTATTGA--
ORTH     GAGCTTATGCAATATCAACCCTAATAACAGAAAAATTAAGGCATTGA--
ACA1     GAGTTCATGAAATATCAACACTAATAACAGAAAATTAAGTAAATGA--
H9       GAGCCTATGCAATATCAGCCCTAATAACAAAAAATTAGATGAATTGACC
J1       GAGCCTATGCAATATCAACCCTAATAACAAAAACAAAAACTAGATGGATTAA--
JSB      GAGCCTATGCAATATCAACCCTAATAACAAAACAAAATTGAGTAAATTGA--
VS461    GAGCCTATGCAATATCAACCCTAATAACAAAACAAAATTAGATGGATTGA--
M57      GAGCCTATGCAATATCAACCCTAATAACAGAAAATTAAGTAAATTGA--
W        GAGCCCATGCAATATCAACTCTAATAAAACAAAAACAGATGGATTGA--
VSDA     GAGCCTATGCAATATCAACCCTAATAACAAAAATTAGATGGATTGA--
NBS23a   GAGCCTATTCAATATCAACCCTAATAACAGAAAATTAAGTAAATAA--
20047    GAGCCCATGAAATATCAATCCTAATAACACAAAAATTAGATGGATTAA--
KL10     GAGCCTATGCAATATCAGCTCTAATAAAACAAAATTAGATGGATTGC--
IP90     GAGCCTATGCAATATCAGCCCTAATAAAACAAAATTAGATGGATTGC--
NBS1AB   GAGCCTATGCAATATCAGCTCTAATAAAACAAAATTAGATGGATTGC--
BITS     GAGCCTATACAATAATCAACCCTAATAATAACAAAAATTAGATGAATTGATC
KL11     GAGCTTATGAAATATCAAAACTAATAACACAAAAATTAAGTGTATTGA--
PBI      GAGCTTATGAAATATCAAAACTAATAACAAAAATTAAGTGTATTGA--
         *  *          *  *            *  ****  *  *****    *
```

Fig. 8-7

| | |
|---|---|
| 2591 | -AAAATTCAGAAGAATTAAAGGAAAAAAATTGAAGATGCTAAAAAATGTAA |
| B31 | -AAAAT---GAAGAATTAAAGGAAAAAAATTGATGCGGCTAAGAAATGTTC |
| 25015 | -AAAAT---GAAGAATTAAAGGAAAAAGATTGCCGCAGTCAAGAAATGTTC |
| ZS7 | -ACGGATCAGAAGAAGGTTTAAAGGAAAAAGATTGCCGCAGCTAAGAAATGCTC |
| 297 | -AAGATTCAGGAGAATTGAAGGCAGAAATTGAAAGGCTAAGAAATGTTC |
| SIMON | -AAGGTTTAGAAGGATTAAATAAGGAAATTGCGGAGGCCAAGAACTGTTC |
| E61 | ----ATTCAGAAGAATTAAAGGCAGAAATTGTAAAGGCTAAGAAATGTTC |
| ORTH | -AAAATTCAGGAGAATTAAAGGCAAAATTGAAGATGCTAAGAAATGTTC |
| ACA1 | -AAAATTCAGGAGAATTAAAGGCAAAAATTGAAGATGCTAAGAAATGTTC |
| H9 | AAAAATTCAGGAGAATTAAAGGAGAAGTTGAAAAGCTAAGAAATGTTC |
| J1 | -AAGGTCTAGAAGGATTAAATAAGAAATTACAGAGGCCAAAAAATGTTC |
| JSB | -AAAATTTAGAAGAATTAAAGACAGAAATTGCAAAGGCTAAGAAATGTTC |
| VS461 | -AAGGTCTAGAAGGATTAAATAAAGAAATTGCGGAGGCCAAGAAATGTTC |
| M57 | -AAAATTCAGGAGAAGAGTTAAATAAAAAATTGAAGAGGCTAAGAACCATTC |
| W | -AAGATCTAGAAGGTTAAGTAAAGAAATTGCAAAGGTGAAGAATGTTC |
| VSDA | -AAGGTTCAGAAGGATTAAAAGCAGAAATTGCAGAAGCTAAGAAATGTTC |
| NBS23a | -AAAATTTAGAAGGGTTAAAAGCAGAGATTGCAGAAGCTAAGAAATGTTC |
| 20047 | -AAGGTTTAGAAGGATTAAAAGCAGAGATTGCAGAAGCTAAGAAATATTC |
| KL10 | -AAGGTCCAGAAGGGTTAAATAAAGAAATTGAAGCGGCTAAGAAATGTTC |
| IP90 | -AAGGTCCAGAAGAAGGTTAAATAAAGAAATTGAAGCGGCTAAGAAATGTTC |
| NBS1AB | -AAGGTCCAGAAGGGTTAAATAATAAAGAAATTGAAGCGGCTAAGAAATGTTC |
| BITS | AAAAATTCAGGAGAATTAAAAGGAGAAGTTGAAAGGCTAAAAACTGTTC |
| KL11 | ----ATTCAGAAGAATTAAAGGAGAAAAATTAAAGAGGCTAAGGATTGTTC |
| PBI | ----ATTCAGAAGAATTAAAGGAGAAAAAATTAAAGAGGCTAAGGATTGTTC |
| | *  ** *   **  *  *   * ** * |

Fig. 8-8

```
2591     CAAAGCATTTACTGATAAACTAAAAAGTAGTCATGCGGAACTCGGT----A
B31      TGAAACATTTACTAATAATAAAACTAAAAGAAAAACACACAGATCTTGGT----A
25015    TGAAGAATTTACTACTAATAAACTAAACTAAAAGAAGTAGTCACACAGAGCTCGGC----A
ZS7      TGAAGAGTTTAGTACTAAACTAAAAGAAGATAATCATGCACAGCTTGGT----A
297      TGAAGAATTTACTGCTAAATTAAAAGGTGAACACAGATCTTGGT----A
SIMON    TGAAGCATTTACTAAAAACTAAAAGAGAGCACACAGATCTTGGG----A
E61      CGAAGACTTTACTAAAAAACTAAAAGAGATAAGCACACAGAACTTGGT----A
ORTH     TGAAGATTTTACTAAAAAACTAGCTGCTGGGCATGCACACAGCTTGGT----A
ACA1     TGAAGAATTTACTAATAAACTAAGAGTAGTCATGCAGATCTTGGT----A
H9       CGAAGAATTTACTAATAAACTAAAAGGTGGTCATGCAGAGCTTGGA----C
J1       TCAAGACTTTATCAATAAACTAAAAGGTGGTCATGCAGAGCTTGGA----C
JSB      CGAAGAATTTACTAATAAACTAAAAGGTCATGCAGATCTTGGC----A
VS461    CGAAGCATTTACTAATAAAGCTACAGACTAAAAGGTCATGCAGATCTTGGA----A
M57      TGAAGCATTTACTAATAGACTAAAAGGTTCTCATGCACAACTTGGAGT----
W        CGATAAATTTACTAAAAGCTAACAGATAGTCATGCACAGCTTGGAGCAG
VSDA     TGAAGACTTTACTAAAAACTAAAAAGCATACAGAACTTGGAGTTG
NBS23a   TGAAGCATTTACTAAAAACTAAAGATAATCATGCAGATCTTGGAGTGG
20047    TGAAGCATTTACTAAAAACTAAAACTAAAAGATAATCATGCACAGCTTGGTAT-A
KL10     TGAAGCATTTACTAATAATAAAAGAGAAGCACGCAGAACTTGGAGTGA
IP90     TGAAGCATTTACTAATAAATAAAAGAGAAGCACCAAGACCTTGGAGTGG
NBS1AB   TGAAGCATTTACTAATAATAAAAGAGAAGCACCAAGACCTTGGAGTGG
BITS     TGAAGCATTTACTAATAATAAAAGAGAAGAACCCAAGAACTTGCAGTGG
KL11     CGAAAATTTACTACTAAGCTGAGAGATAGTCATGCAGAGCTTGGTAT-A
PBI      CCAAAATTACTACTAAGCTAAAAGATAGTCATGCAGAGCTTGGTAT-A
            *              *              *              ***
```

Fig. 8-9

```
2591     TAGCGAATGGAGCTGCTAGTGATGCTAATGCAAAAGCGGCTATTTTAAAA
B31      AAGAAGGTG------TTACTGATGCTGATGCAAAGAAGCCATTTTAAAA
25015    AACAGGATG------CTCAGGATGATGATGCAAAAAGGCTATCTTAAGA
ZS7      TACAGGGCG------TTACTGATGAAAATGCAAAAAAGCTATTTTAAAA
297      AAGAAGGCG------TTACTGATGATAATGCAAAAAAGCCATTTTAAAA
SIMON    AAGAGAATG------CTACCGATGAAGATGCAAAAGATGCTATTTTAAAA
E61      AACAGGATG------CTAATGATGATGCAAAAAAGCTATTTTAAAA
ORTH     TAGACGGAG------CTACTGATAATGATTCAAAAGAAGCAATTTGAAA
ACA1     AACAAGGTG------TTAATGACGATGATGCAAAAAAGCTATTTTAAAA
H9       TTGCTGCTG------CTACTGATGAAATGCAAAAGCAGCCATTTTAAAA
J1       TTGTTGCTG------CTACTGATGCTAATGCAAAAGCAGCAGCTATTTTAAAA
JSB      AACAGGATG------CTACCGATGATCATGCAAAAGCAGCAGCTATTTTAAAA
VS461    AACATAATG------CTACTGATGCTGATGATCATGCAAAAGAAGCAATTTGAAA
M57      ----------TGCTGCTGCTACTGATGATGATGATGCAAAAGAAGAAGCTATTTTAAAA
W        TTGG---TGGTGCTATTAATGATGATGATCGTGCAAAAGAAGAAGCTATTTTAAAA
VSDA     CTG------CTGCTACTGATGATGATGCAAAAAAGCTATTTTAAAA
NBS23a   CGGGGAATGGAGCTTCTACTGATGAAAATGCACAGAAAGCTATTTTAAAA
20047    C---AGAATGGTGCTTCTCTTGATGATGAGGCAAAAAAAGCTATTTTAAAA
KL10     A----TGGTGGTGATACTACTGATGATAATGCAAAAGCAGCTATTTTTAAA
IP90     C----GAATGGTGATACTACTGATAATAATGCAAAAGCAGCTATTTTAAAA
NBS1AB   C----GAATGGTGATACTACTGATAATAATGCAAAAGCAGCTATTTTAAAA
BITS     C----GGCTGGTGCTGCTACTGATATTGATGCAAAAGAGCTATTTTAAAA
KL11     CAAAA---------CGTTCAGGATGATAATGCAAAAAAGCTATTTTAAAA
PBI      CAAAG---------CGTTCAGGATGATAATGCAAAAAAGCTATTTTAAAA
                           *           **          *         ** ** ** *
```

Fig. 8-10

```
2591     ACAAATGGTAC----TAAAGATAAGGGTGCTCAAGAGCTTGAAAAGTTATT
B31      ACAAATGGTAC----TAAAACTAAAGGTGCTGAAGAACTTGGAAAATTATT
25015    ACACATAATAC----TAAGGATAAGGGTGCTGAAGAACTTGATAAGTTATT
ZS7      GCAAATGCAGCGGGTAAAGATAAGGGTGCTGAAGAACTTGAAAAGTTGTC
297      ACAAATAATGA----TAAACTAAGGGCGCTGATGAACTTGAAAAGTTATT
SIMON    ACAGATGCTAC----TAAAGATAAGGGTGCTGCTGAACTTGAAAAGCTATC
E61      ACAAATGGCGA----TAAAACTTTGGGTGCTGCTGAACTTGAAAAGCTATC
ORTH     ACAAATGGGAC----TAAAACTAAGGGTGCTGAAGAACTTGTAAAGTTATC
ACA1     ACACATGCAGA----TAAAACTAAAGGTGCTGAAGAACTTGGAAAGTTATT
H9       ACAAATGGAAC----TAAAGATAAGGGTGCTGAAGAACTTGAAAAGTTATT
J1       ACAAATGGCGA----TAAAACTAAAGGGCTGACGAATTGAAAAGCTATT
JSB      ACACATGCAAC----TACCGATAAAGGTGCTAAAGAATTTAAAGATTATT
VS461    ACAAATGGGAC----TAAAACTAAGGGTGCTAAAGAACTTGAAGAGTTGTT
M57      TCAAATCCTAC----TAAAGATAAGGGTGCTAAAGAACTTAAAGACTTATC
W        ACACATGGGAC----TAACGATAAGGGTGCTAAAGAACTTAAAGAGTTATC
VSDA     GCAAATGGGGA----TAAGACTTTAGGTGTGTTGAAGAGCTTGAAAAGTTATT
NBS23a   ACAAATGCGAT----TGTCGATAAGGGTGCTAAAGACCTTAAAGAGTTATT
20047    ACAAATGTGGA----CAAAACCAAGGGTGCTGAAGAGCTTGAAAAGTTATT
KL10     ACACATCCTAC----TAAAGATAAGGGTGCTTCGAAGATCTTGAAAAGTTATC
IP90     ACACATGGGAC----TGAGGACAAGGGTGTTAAAGAACTTAAAGATTTGTT
NBS1AB   ACACATGGGAC----TGAGGACAAGGGTGTTAAAGAACTTAAAGATTTGTT
BITS     ACAAATAGGGA----CAAGGACCTAGGTGCTGATGAACTTGGCAAGTTATT
KL11     ACACATGGGAA----TAAAGACAAGGGTGCTAAAGAACTTAAAGAGTTATC
PBI      ACACATGGAAC----TAAAGACAAGGGTGCTAAAGAACTTGAAGAGTTATT
         **  *                           *           **
```

Fig. 8-11 (Page 4) Continuation

| | | | | |
|---|---|---|---|---|
| 2591 | TGAATCAGTAAAAAACTTGTCAAAAGCAGCTCAAGAAACACTAAATAATT |
| B31 | TGAATCAGTAGAGGTCTTGTCAAAAGCAGCTAAAGAGATGCTTGCTAATT |
| 25015 | TAAACCGGTGGAGAACTTGTCAAAAGCGGCTAAAGAGATGCTATCCAATT |
| ZS7 | CGGATCATTAGAGAAAGCTTATCAAAAGCAGCTAAAGAGATGCTTGCTAATT |
| 297 | TGAATCAGTAAAAAACTTGTCAAAAGCAGCTAAAGAGATGCTTACTAATT |
| SIMON | TGAATCAGTAGCAAGCTTAGTAAAAGCGGCTCAAGAAGCACTAACTAATT |
| E61 | TGAATCAGTAACAAGCTTGTCAAAAGCAGCTAAAGAATCACTAACCAATT |
| ORTH | TGAATCAGTAGCAAGCTTGTCAAAAGCGGCTCAAGAAGCATCAGCTAATT |
| ACA1 | TAAATCAGTAGCAAGCTTGGTAAAAGCAGCTCAAGAAGCACTAACCAATT |
| H9 | TAAATCAGTAGAAAGCTTTGTCAAAAGCAGCTCAAGAAGCACTAACTAATT |
| J1 | TAAATCAGTAGAAGGTTTGTTAAAAGCAGCTCAAGAAGCACTAACTAATT |
| JSB | TGAATCAGTAGAAGGTTTGTCAAAAGCAGCTCAAGAAGCACTAACTAATT |
| VS461 | TAAATCAGTAGAAAGCTTGTCAAAAGCAGCTCAAGAAGCATTAAGTAATT |
| M57 | TGAATCAGTAGAAAGCTTGGCAAAAGCAGCGCGCAAGAAGCATTAGCTAATT |
| W | TGAATCAGTAGAAAGCTTGTCAAAAGCAGCGCGCAAGCAGCATTAGCTAATT |
| VSDA | TAAATCAGTAGAAAATTGTCAAAAGCAGCGCGCAAGAAGCACTAGCTAATT |
| NBS23a | TGAATCAGTAGAAAATTGTCAAAAGCAGCGCGCAAGAAGCACTAACTAATT |
| 20047 | TAAATCAGTAGAAAGCTTGTCAAAAGCAGCGCGCAAGAAGCACTAACTAATT |
| KL10 | TGAATCAGTAAAAAGCTTGTCAAAAGCAGCGCGCAAGCAGCATTAAGCAATT |
| IP90 | GAAATCAGTAGAAAGCTTGGCAAAAGCAGCGCGCAAGCAGCATCAAGCAATT |
| NBS1AB | GAAATCAGTAGAAAGCTTGGCAAAAGCAGCGCGCAAGCAGCATCAAGCAATT |
| BITS | TAAATCAGTAGAAAGCTTGTCAAAAGCAGCGCGCAAGAAGCATCAGCTAATT |
| KL11 | TGAATCATTAGAAAATTGTCAAAAGCAGCGCGCAAGAAGCACTAGCTAATT |
| PBI | TAAATCACTAGAAAGCTTGTCAAAAGCAGCGCGCAAGCAGCATTAACTAATT |
| | * * ** ***** ** ** *** |

Fig. 8-12

| | |
|---|---|
| 2591 | CA |
| B31 | CA |
| 25015 | CA |
| ZS7 | CA |
| 297 | CA |
| SIMON | CA |
| E61 | CA |
| ORTH | CA |
| ACA1 | CA |
| H9 | CA |
| J1 | CA |
| JSB | CA |
| VS461 | CA |
| M57 | CA |
| W | CA |
| VSDA | CA |
| NBS23a | CA |
| 20047 | CA |
| KL10 | CA |
| IP90 | CA |
| NBS1AB | CA |
| BITS | CA |
| KL11 | CA |
| PBI | CA* |

Fig. 8a-1

```
28691     TGTAATAATTCAGGAAAAGATGGGAAT----GCATCTGCAAATTCTGCTGA
2591      TGTAATAATTCAGGAAAAGATGGGAAT----ACATCTGCAAATTCTGCTGA
IP2       TGTAATAATTCAGGAAAAGATGGGAAT----ACATCTGCAAATTCTGCTGA
25015     TGTAATAATTCAGGAAAAGATGGGAACGCTGCATCTACTAATCCTGCTGA
ZS7       TGTAATAATTCAGGAAAAGATGGGAAT----ACATCTGCAAATTCTGCTGA
297       TGTAATAATTCAGGAAAAGATGGGAAT----ACATCTGCAAATTCTGCTGA
SIMON     TGTAATAATTCAGGAAAAGGTGGGATTCTACATCTACTAATCCTGCTGA
E61       TGTAATAATTCAGGAAAAGGTGGGATTCTACATCTACTAATCCTGCTGA
ORTH      TGTAATAATTCAGGAAAAGGTGGAGATTCTGCATCTACTAATCCTGCTGA
ACA1      TGTAATAATTCAGGAAAAGGTGGGATTCTGCATCTACTAATCCTGCTGA
H9        TGTAATAATTCAGGAAAAGGTGGGATTCTGCAGATTCTACTAATCCTGCTGA
J1        TGTAATAATTCAGGAAAAGGTGGGATTCTGCATCTACTAATCCTACTGA
JSB       TGTAATAATTCAGGAAAAGGTGGGATTCTGCATCTACTAATCCTGCTGA
VS461     TGTAATAATTCAGG----TGGGGATATGCATCTACTAATCCTG---A
M57       TGTAATAATTCAGG----TGGGGATACCGCATCTACTAATCCTG---A
W         TGTAATAATTCAGG----TGGGGATACTGCATCTACTAATCCTG---A
VSDA      TGTAATAATTCAGG----TGGGGATACTGCATCTACTAATCCTG---A
NBS23a    TGTAATAATTCAGG----TGGGGATACTGCATCTACTAATCCTG---A
20047     TGTAATAATTCAGG----TGGGGATACTGCATCTACTAATCCTG---A
KL10      TGTAATAATTCAGG----TGGGGATACTGCATCTACTAATCCTG---A
IP90      TGTAATAATTCAGG----TGGGGATAGTGCATCTACTAATCCTG---A
NBS1AB    TGTAATAATTCAGG----TGGGGATACTGCATCTACTAATCCTG---A
BITS      TGTAATAATTCAGG----TGGAGATTCTGCATCTACTAATCCTG---A
KL11      TGTAATAATTCAGG----TGGGGATTCTGCATCTACTAATCCTG---A
PBI       TGTAATAATTCAGG----TGGGGATTCTGCATCTACTAATCCTG---A
H13       TGTAATAATTCAGG----TGGGGATACTGCATCTACTAATCCTG---A
          *************    *    *    *    *  **   ****   *
```

Fig. 8a-2

| | |
|---|---|
| 28691 | TGAGTCTGTTAAAGGGCCTAATCTTACAGAAATAAGTAAAAAATTACAG |
| 2591 | TGAGTCTGTTAAAGGGCCTAATCTTACAGAAATAAGTAAAAAATTACAG |
| IP2 | TGAGTCTGTTAAAGGGCCTAATCTTACAGAAATAAGTAAAAAATTACGG |
| 25015 | TGAGTCTGTTAAAGGGCCTAATCTTACAGAAATAAGTAAAAAATTACAG |
| ZS7 | TGAGTCTGTTAAAGGGCCTAATCTTACAGAAATAAGTAAAAAATTACGG |
| 297 | TGAGTCTGTTAAAGGGCCTAATCTTACAGAAATAAGTAAAAAATTACGG |
| SIMON | TGAGTCTGTTAAAGGGCCTAATCTTACAGAAATAAGTAAAAAATTACAA |
| E61 | CGAGTCTGCTAAAGGGCCTAATCTTACAGAAATAAGTAAAAAATTACAG |
| ORTH | CGAGTCTGCGAAAGGACCTAATCTTACAGAAATAAGCAAAAAATTACAG |
| ACA1 | CGAGTCTGCGAAAGGACCTAATCTTACAGAAATAAGCAAAAAATTACAG |
| H9 | CGAGTCTGCGAAAGGACCTAATCTTACAGAAATAAGCAAAAAATTACAG |
| J1 | CGAGTCTGCGAAAGGACCTAATCTTACAGAAATAAGCAAAAAATTACAG |
| JSB | CGAGTCTGCGAAAGGACCTAATCTTACAGAAATAAGCAAAAAATTACAG |
| VS461 | TGAGTCTGCAAAAGGACCTAATCTTACAGTAATAAGCAAAAAATTACAG |
| M57 | TGAGTCTGCGAAAGGACCTAATCTTACAGTAATAAGCAAAAAATTACAG |
| W | TGAGTCTGCGAAAGGACCTAATCTTACAGTAATAAGCAAAAAATTACAG |
| VSDA | TGAATCTGCGAAAGGACCTGATCTTACAGTAATAAGCAAAAAATTACAG |
| NBS23a | TGAGTCTGCGAAAGGACCTGATCTTACAGAAATAAGCAAAAAATTACAG |
| 20047 | TGAATCTGTTAAGGGACCTAATCTTACAGAAATAAGCAAAAAATTACAG |
| KL10 | TGAATCTGCGAAAGGACCTGATCTTACAGAAATAAGCAAAAAATTACAG |
| IP90 | TGAGTCTGCAAAAGGACCTAATCTTTATAGAAATAAGCAAAAAATTACAG |
| NBS1AB | TGAGTCTGCGAAGGACCTGATCTTACAGTAATAAGCAAAAAATTACAG |
| BITS | TGAGTCTGCAAAAGGACCTAATCTTTATAGAAATAAGCAAAAAATTACAG |
| KL11 | TGAGTCTGCAAAAGGACCTAATCTTACAGTAATAAGCAAAAAATTACAG |
| PBI | TGAATCTGCAAAAGGACCTAATCTTACCGTAATAAGCAAAAAATTACAG |
| H13 | TGAGTCCACTAAAGGACCTAATCTTTATAGAAATAAGCAAAAAATTACAG |
| | * ** ** *** **** ***** ****** ****************** |

Fig. 8a-3

```
28691    AATCTAACGCAGTTGTTCTGGCCGTGAAAGAAGTTGAGACCTTACTTGCA
2591     AATCTAACGCAGTTGTTCTCGCCGTGAAAGAAGTTGAAACTCTGCTTGCA
IP2      ATTCTAATGCGGTTTTACTTGCTGTGAAAGAGAGTTGAAGCGTTGCTGTCA
25015    ATTCTAATACGGTTGTGCTAGCTGTGAAAGAAGTTGAAGCTTTGCTTACA
ZS7      ATTCTAATGCGGTTTTACTTGCTGTGAAAGAGAGTTGAAGCGTTGCTGTCA
297      AATCTAACGCAGTTGTTCTCGCCGTGAAAGAAGTTGAAACTTTGCTTACA
SIMON    ATTCTAATGCATTGTACTTGCTGTTAAAGAAGTTGAGACTTTGGTTGCA
E61      ATTCTAATGCATTGTACTTGCTGTTAAAGAAGTTGAGACTTTGGTTGCA
ORTH     ATTCTAATGCATTGTACTTGCTGGCTGTTAAAGAAGTTGAGACTTTGGTTCA
ACA1     ATTCTAATGCATTGTACTTGCTGTGAAAGAAGTTGAGACTTTGGTTCA
H9       ATTCTAATGCATTGTACTTGCTGTTAAAGAAGTTGAGACTTTGGTTCA
J1       ATTCTAATGCATTGTACTTGCTGTTAAAGAAGTTGAGACTTTGGTTCT
JSB      ATTCTAATGCATTGTACTTGCTGTTAAAGAAGTTGAGACTTTGGTTTA
VS461    ATTCCAATGCATTGTACTTGCTGTGAAAGAAGTTGAGGCTTTGCTTCA
M57      ATTCTAATGCAGTTGTACTTGCTGTGAAAGAAGTTGAGGCTTTGATCTCA
W        ATTCTAATGCATTGTACTTGCTGGCTGTGAAAGAAGTTGAGGCTTTGATCTCA
VSDA     ATTCTAATGCATTGTACTTGCTGTGAAAGAAGTTGAGGCTTTGCTTCA
NBS23a   ATTCTAATGCATTGTACTTGCTCGCCGTTGTGAAAGAAGTTGAGGCTTTGATTCA
20047    ATTCTAATGCATTGTACTTGCTGGCTGTGAAAGAAGTTGAGGCTTTGATCTCA
KL10     ATTCTAATGCATTGTACTTGCTGGCTGTGAAAGAAGTTGAAGCTTTGCTTCA
IP90     ATTCTAATGCATTGTACTTGCTGGCTGTGAAAGAAGTTGAGGCTTTGCTTCA
NBS1AB   ATTCTAATGCATTGTACTTGCTGGCTGTGAAAGAAGTTGAGGCTTTGCTTCA
BITS     ATTCTAATGCATTGTACTTGCTGGTTGTGAAAGAAGTTGAGGCTTTGCTTCA
KL11     ATTCTAATGCATTTTACTTGCTGGTTGTGAAAGAAGTTGAGGCTTTGCTTTCA
PBI      ATTCTAATGCAGTTGTACTTGCTGGCTGTGAAAGAAGTTGAGGCTTTGCTTTCA
H13      ATTCCAATGCAGTTGTACTTGGCTGTGAAAGAAGTTGAGGCTTTGATCTCA
         *   * **        *  **   *       *  *        **** ****  *
```

Fig. 8a-4

```
28691   TCTATAGATGAACTTGCTACCAAAGCTATTGGTAAAAAATAGGCAATAA
2591    TCTATAGATGAAGTTGCTAAGAAAGCTATTGGGAATTTGATAGCCCAAA
IP2     TCTATAGATGAAATTGCTGCTAAAGCTATTGGTAAAAAATACACCAAAA
25015   TCTATAGATGAACTTGCTACTAAAGCTATTGGTAAAAAATACACCAAAA
ZS7     TCTATAGATGAGCTTGCTA---AAGCTATTGGTAAAAAATAAAAACGA
297     TCTATAGATGAGCTTGCTA---AAGCTATTGGTAAAAAATAAAAACGA
SIMON   TCTATAGATGAACTTGCTACTAAAGCTATTGGTAAAAAATAAAAATGA
E61     TCTATAGATGAACTTGCTACTAAAGCTATTGGTAAAAAATAAAAATGA
ORTH    TCTATAGATGAACTTGCTACTAAAGCTATTGGTAAAAAATACAACAAAA
ACA1    TCTATAGATGAACTTGCCAATAAAGCTATTGGTAAAAAATACAACAAAA
H9      TCTATAGATGAACTTGCTCAAGCTATTGGTAAAAAATACAA---AA
J1      TCTATAGATGAACTTGCTAATAAAGCTATTGGTCAAAAATACAA---AA
JSB     TCTATAGATGAACTTGCTAAGAAAGCTATTGGTCAAAAATAGACAATAA
VS461   TCTATAGATGAACTTGCTA---AAACTATTGGTAAAAAATAGAGGCAAA
M57     TCTATAGATGAACTTGCTA---AAACTATTGGTAAAAAATAGAGGCAAA
W       TCTATAGATGAACTTGCTAATAAAGCTATTGGTAAAGTAATACATCAAAA
VSDA    TCTATAGATGAACTTGCTAATAAAGCTATTGGTAAAAAATAAATCAAAA
NBS23a  TCTGTAGATGAACTTGCCA---AAGCTATTGGTAAAAAATACATCAAAA
20047   TCTGTAGATGAACTTGCTA---AGGCTATTGGTAAAAAATAGATAACAA
KL10    TCTATAGATGAACTTGCTA---AAGCTATTGGTCAAGAATACAACAAAA
IP90    TCTATAGATGAACTTGCTA---AAGGTATTGGTAAAAAATAGATCAAAA
NBS1AB  TCTATAGATGAACTTGCTA---AAGCTATTGGTCAAAAATAGATCAAAA
BITS    TCTATAGATGAACTTGCTA---AAGCTATTGGTCAAAAATAGATCAAAA
KL11    TCTATAGATGAACTTTCTA---AAGCTATTGGTAAAAAATAAAAATGA
PBI     TCTATAGATGAACTTGCTA---AAGCTATTGGTAAAAAATAAAAATGA
H13     TCTATAGATGAACTTGCTA---AGGCTATTGGTAAAAAAGTAGAGGCAAA
        *** *******  **  *    *  ******* *    *       *
```

Fig. 8a-5

```
28691   T----GGTTTAGAGAGGCCAATCA----GAGTAAAAACACATCATTGTTATCAG
2591    T----GGTTTAAATGCCGGTGC----TAATCAAAACGGATCATTGTTAGCGG
IP2     TAATGGTTTGGATACCGAAAA----TAATCACAATGGATCATTGTTAGCGG
25015   TAATGGTTTGGATACCGAAAA----TAATCACAATGGATCATTGTTAGCGG
ZS7     TGGTAGTTTAGGTGATGAAGC----AAATCACAACGAGTCATTGTTAGCGG
297     TGTTAGTTTAGATAATGAGGC----AGATCACAACGATCATTAATATCAG
SIMON   TGGCACTTTAGAGAACGAAGC----AAATCACAACGATCATTGTTAGCGG
E61     TGGCACTTTAGATAACGAAGC----AAATCACAACGATCATTGTTAGCAG
ORTH    TAATGGTTTAGGCGCGCCAATGC----GGATAAAAACGGATCATTGTTAGCAG
ACA1    T----GGTTTAGGCGCGCCGAAGC----GAATCGCAACGAATCATTGTTGGCCG
H9      CAATGGTTTGACTGCCGAACA----GAATCAAAACGGATCATTGTTAGCAG
J1      CAATGGTTTGAGTGCCGAACA----GAATCAAAACGGATCATTATTAGCAG
JSB     TAATGGTTTTAGCTGCTTTAAA----TAATCAGAATGGATCGTTGTTAGCAG
VS461   ----TGGTTTGGGTAACGAAGC----GGATAAAAACGGATCATTATTAGCAG
M57     TAATGGTTTAAATGCTAATGC----GGGTCAAAACGGATCATTGTTAGCAG
W       T----GGTTTAGATGCTGATGC----TAATCACAACGGATCATTGTTAGCAG
VSDA    TAATGGTTTAGATACTCTGTC----AAATCAAAACGGATCATTGTTAGCAG
NBS23a  TACTGGTTTAAGTGCTAATCA----GAATCATAACACTTCATTGTTAGCAG
20047   T----GGTTTAGTTGCTGATGC----GGGTCACACAGCGCATTGTTAGCAG
KL10    TAGTGGTTTAGCTGCTGCTACTCAGAATAAAAACACCTCGTTGTTAGCAG
IP90    TAATGGTTTAGCTGCTGCTACTCAGGATAAAAACACCTCATTGTTAGCAG
NBS1AB  TAATGGTTTAGCTGCTGCTACTCAGGATAAAAACACCTCATTGTTAGCAG
BITS    TAATGGTTTAGCTGTCGAAGC----GAATTTTAACCATCATTGTTAGCAG
KL11    TAATGGTTTAGATAACGAAGC----AAATCGAAACGAATCATTGATAGCAG
PBI     TGGTACTTTAGATAACGAAGC----AAATCGAAACGAATCATTGATAGCAG
H13     T----GGTTTGGGTAACGAAGC----GGATAGAAACACCTCATTGTTAGCAG
              ***                          *              *  **    *
```

Fig.8a-6

```
28691    GAGCTTATGCAATATCTGACCTAATAGCAGAAAAATTAAATGTATTGA--
2591     GAGCCTACGTAATATCAACCTAATAGCAGAGAAAATTAGATGGATTGA--
IP2      GAGCTTATGCAATATCAACCCTAATAACACAAAAATTAGATGGATTGA--
25015    GGGCCTATGCAATATCAACGCTAATAACACAAAAGTTAGGTGGATTGA--
2S7      GAGCTTATACAATATCAACCTTAATAACACAAAAATTAAGTAAATTAA--
297      GAGCATATTTAATTTCAACATTAATAATAAAAAAATAAGTGCAATAA--
SIMON    GAGCTTATGCAATATCAAATCTAATAAAAGAAAAATTAGATGGATTGA--
E61      GAGCCTATGCAATATCAACTCTAATAACACAAAAATTAAGTGTATTGA--
ORTH     GAGCCTATGCAATATCAACCCTAATAACAGAAAAATTAAAGGCATTGA--
ACA1     GAGTTCATGAAATATCAACACTAATAACAGAAAAATTAAGTAAATTGA--
H9       GAGCCTATGCAATATCAGCCCTAATAACAAAAAAATTAGATGAATTGACC
J1       GAGCCTATGCAATATCAACCCTAATAACAAAAACTAGATGGATTAA--
JSB      GAGCCTATGCAATATCAACCCTAATAACAGAAAAATTGAGTAAATTGA--
VS461    GAGCCTATGCAATATCAACCCTAATAACACAAAAATTAGATGGATTGA--
M57      GAGCCTATGCAATATCAACCCTAATAACACAAAAATTAAGTAAATTGA--
W        GAGCCCATGCAATATCAACCTAATAACAAAAAACAGATGGATTGA--
VSDA     GAGCCTATGCAATATCAACCCTAATAACAAAAAAATTAGATGGATTGA--
NBS23a   GAGCCTATTCAATATCAACCCTAATAACAGAAAAATTAAGTAAATTAA--
20047    GAGCCCATGAAATATCAGTATCAGCTCTAATAACACAAAAATTAGATGGATTGA--
KL10     GAGCCTATGCAATATCAGCTATCAGCTAATAACACAAAAATTAGATGGATTGC--
IP90     GAGCCTATGCAATATCAGCTATCAGCTAATAACACAAAAATTAGATGGATTGC--
NBS1AB   GAGCCTATGCAATATCAGCTCTAATAACAAAAAAATTAGATGGATTGC--
BITS     GAGCCTATACAATATCAACCCTAATAACAATAACAAAAAATTAGATGAATTGATC
KL11     GAGCTTATGAAATATCAAAACTAAAACTAATAACACAAAAATTAAGTGTATTGA--
PBI      GAGCTTATGAAATATCAAAACTAATAACAAAAAATTAAGTGTATTGA--
H13      GAGCTCATGAAATATCAATTCTAATAACAAAATTAACTGCATTAA--
         *  *          *  *       *           *****   *     *   ****
```

Fig.8a-7

| | | | |
|---|---|---|---|
| 28691 | -AAAAT---GAAGAATTAAAGGAAAAGATTGATACAGCTAAGCAATGTTC |
| 2591 | -AAAATTCAGAGAATTAAAGGAAAAAATTGAAGATGCTAAAAATGTAA |
| IP2 | -AAAAT---GAAGGATTAAAGGAAAAAATTGATGCGGCTAAGAAATGTTC |
| 25015 | -AAAAT---GAAGAATTAAAGGAAAAAGATTGCCGCAGTCAAGAAATGTTC |
| ZS7 | -ACGGATCAGAAGGTTAAAGGAAAAAGATTGCCGCAGCTAAGAAATGCTC |
| 297 | -AAGATTCAGGAGAATTGAAGGCAGAAATTGAAAAGGCTAAGAAATGTTC |
| SIMON | -AAGGTTTAGAAGGATTAAATAAGGAAATTGCGGAGGCCAAGAACTGTTC |
| E61 | ----ATTCAGAAGAATTAAAGGCAGAAATTGTAAAGGCTAAGAAATGTTC |
| ORTH | -AAAATTCAGGAGAATTAAAGGCAAAATTGAAGATGCTAAGAAATGTTC |
| ACA1 | -AAAATTCAGAGAATTAAAGGCAGAAATTGAAGATGCTAAGAAATGTTC |
| H9 | AAAAATTCAGAGAATTAAAGGAGAAGTTGAAAAGCTAAGAAATGTTC |
| J1 | -AAGGTCTAGAAGGATTAAATAAAGAAATTACAGAGGCCAAAAAATGTTC |
| JSB | -AAAATTTAGAAGAATTAAAGGACAGAATTGCAAAGGCTAAGAAATGTTC |
| VS461 | -AAGGTCTAGAAGGATTAAATAAAGAAATTGCGGAGGCCAAGAAATGTTC |
| M57 | -AAAATTCAGAAGAATTAAATAAAAAAATTGAAGAGGCTAAGAACCATTC |
| W | -AAGATCTAGAAGGTTAAGTAAAGAAATTGCAAAGGTGAAGAAATGTTC |
| VSDA | -AAGGTTCAGAGAATTAAAAGCAGAAATTGCAGAAGCTAAGAAATGTTC |
| NBS23a | -AAAATTTAGAAGGGTTAAAAGCAGAGATTGCAGAAGCTAAGAAATATTC |
| 20047 | -AAGGTTTAGAAGGGTTAAAAGCAGAGATTGCAGAAGCTAAGAAATGTTC |
| KL10 | -AAGGTCCAGAGAAGGGTTAAATAAAGAAATTGAAGCGGCTAAGAAATGTTC |
| IP90 | -AAGGTCCAGAGAAGGGTTAAATAAAGAAATTGAAGCGGCTAAGAAATGTTC |
| NBS1AB | -AAGGTCCAGAGAAGGGTTAAATAAAGAAATTGAAGCGGCTAAGAAATGTTC |
| BITS | AAAAATTCAGGAGAATTAAAGGAGAAGTTGAAAAGGCTAAAACTGTTC |
| KL11 | ----ATTCAGAAGAATTAAAGGAGAAAATTAAAGAGGCTAAGGATTGTTC |
| PBI | ----ATTCAGAAGAATTAAAGGGAAAAATTAAAGAGGCTAAGGATTGTTC |
| H13 | -AAGATTCAGGAGGATTAAAAGCAGAGATTGCAGAAGCTAAGAAATGTTC |

Fig. 8a-8

```
28691   TACAGAATTTACTAATAAACTAAAAAAGTGAACATGCAGTGCTTGGT----C
2591    CAAAGCATTTACTGATAATAAACTAAAAAAGTAGTCATGCGGAACTCGGT----A
IP2     TGAAACATTTACTACTAATAAATTAAAAGAAAACACAGATCTTGGT----A
25015   TGAAGAATTTACTACTAATAAACTAAAAAAGTAGTCACACAGAGCTCGGC----A
ZS7     TGAAGAGTTTAGTACTAATAAACTAAAAAGATAATCATGCACAGCTTGGT----A
297     TGAAGAATTTACTGCTAAATTAAAAGGTGAACACACAGATCTTGGT----A
SIMON   TGAAGCATTTACTACTAATAAAAACTAAAAGAGAAGCACACAGATCTTGGG----A
E61     CGAAGACTTTACTAAAAAACTAAAAAAACTAAAAGATAAGCACACAGAACTTGGT----A
ORTH    TGAAGATTTTACTAAAAAAACTAGCTCGGCATGCACAGCTTGGT----A
ACA1    TGAAGAATTTACTAATAAACTAAGAGAGTTAGTCATGCAGAGCTTGGT----A
H9      CGAAGAATTTACTAATAAACTAAAAAAGGTGGTCATGCAGAGCTTGGA----C
J1      TCAAGACTTTATCAATAATAAACTAAAAAAGGTGGTCATGCAGAGCTTGGA----C
JSB     CGAAGAATTTACTAATAAACTAAAAAAGTGGTCATGCAGATCTTGGC----A
VS461   CGAAGCATTTACTAAAAAAACTACAAGACTAAAGCAGATAGTAACGCAGATCTTGGA----A
M57     TGAAGCATTTACTAATAATAAGGTTCTCATGCACAACTTGGAGT--
W       CGATAAATTTACTAATAAAGCTAAAAAAACTAAAGATAGTCATGCACAGCTTGGAGCAG
VSDA    TGAAGACTTTACTAAAAAAACTAAAGAAGCATACAGAACTTGGAGTTG
NBS23a  TGAAGCATTTACTAAAAAAACTAAGAATAATCATGCAGATCTTGGAGTGG
20047   TGAAGCATTTACTAAAAAAACTAAAGATAATCATGCACAGCTTGGTAT--A
KL10    TGAAGCATTTACTAAAAAAACTAAAGAGAAGCACGCAGAACTTGGAGTGA
IP90    TGAAGCATTTACTAATTAAAAGAGAAGCACCAGAGACCTTGGAGTGG
NBS1AB  TGAAGCATTTACTAATTAAAGAGAAGCACCAGAACCTTGGAGTGG
BITS    TGAAGCATTTACTAATAAAGAGAAGAGACCCAGAACTTGCAGTGG
KL11    CGAAAAATTTACTACTAAGCTGAGAGATAGTCATGCAGAGCTTGGTAT--A
PBI     CCAAAAATTTACTAAGCTAAAAGATAAGCTAAAAGATAGTCACAGCTTGGTAT--A
H13     TGAAGCATTTACTAATAATAAAAAACTAAAAATGCACAGCTTGGTAT--A
                ****              *                      *      **
```

Fig. 8a-9

```
28691    TGGACAATC-------TTACTGATGATAATGCACAAAGAGCTATTTTAAAA
2591     TAGCGAATGGAGCTGCTAGTGATGCTAATGCAAAAGCGGCTATTTTAAAA
IP2      AAGAAGGTG-------TTACTGATGCTGATGCAAAGAAGCCATTTTAAAA
25015    AACAGGATG-------CTCAGGATGATGATGCAAAAAAGGCTATCTTAAGA
2S7      TACAGGGCG-------TTACTGATGAAAATGCAAAAAAGCTATTTTAAAA
297      AAGAAGGCG-------TTACTGATGATAATGCAAAAAGCCATTTTAAAA
SIMON    AAGAGAATG-------CTACCGATGAAGATGCAAAAAAGCTATTTTAAAA
E61      AACAGGATG-------CTAATGATGATGCAAAAAAGCTATTTTAAAA
ORTH     TAGACGGAG-------CTACTGATAATGATTCAAAAGAAGCAATTTGAAA
ACA1     AACAAGGTG-------TTAATGACGATGATGCAAAAAAGCTATTTTAAAA
H9       TTGCTGCTG-------CTACTGATGAAAATGCAAAAAAGCCATTTTAAAA
J1       TTGTTGCTG-------CTACTGATGCTAATGCATGCAAAAGCCATTTTAAAA
JSB      AACAGGATG-------CTACCGATGATCATGCAAAAGCAGCAGCTATTTTAAAA
VS461    AACATAATG-------CTACTGATGCTGATTCATGCAAAAGAAGCAATTTGAAA
M57      ---------TGCTGCTGCTATTAATGATGATGATGCAAAAGAAGAAGCTATTTTAAAG
W        TTGG----TGGTGCTATTAATGATGATGATGCAAAAGAAGAAGCTATTTTAAAA
VSDA     CTG-------CTGCTACTGACTGCTACTGATGATAATGCACAGAAAAGCTATTTTAAAA
NBS23a   CGGGGAATGGAGCTTCTACTGCTTCTCTTGATGATGAAAAAGCTATTTTAAAA
20047    C---AGAATGGTGCTTCTCTCTTGATGATGATGAAAAGCAGCTATTTTAAAA
KL10     A---TGGTGGTGATACTACTGATGATAATGCAAAAGCAGCTATTTTAAAA
IP90     C---GAATGGTGATACTACTGATGATAATAATGCAAAAGCAGCTATTTTAAAA
NBS1AB   C---GAATGGTGATACTACTGATAATAATGCAAAAGCAGCTATTTTAAAA
BITS     C---GGCTGGTGCTGCTACTACTGATATTGATGCAAAAAAGCAGCTATTTTAAAA
KL11     CAAAA---------CGTTCAGGATGATAATGCAAAAAAGAGCTATTTTAAAA
PBI      CAAAG---------CGTTCAGGATGATAATGCAAAAAAGCTATTTTAAAA
H13      CAAAA---------CGTTCAGGATGTTGAGGCAAAAAAGCTATTTTAAAA
                       *         **        *  *    ** ** ** ** *
```

| | |
|---|---|
| 28691 | TAAAGCGGTAGAAAACTTATCAAAAGCAGCTCAAGACACACATTAAAAAATG |
| 2591 | TGAATCAGTAAAAAACTTGTCAAAAGCAGCTCAAGAAACACTAAATAATT |
| IP2 | TGAATCAGTAGAGGTCTTGTCAAAAGCAGCTCAAGAGATGCTTGCTAATT |
| 25015 | TAAACCGGTGGAGAACTTGTCAAAAGCGGCTAAAGAGATGCTATCCAATT |
| ZS7 | CGGATCATTAGAAAGCTTATCAAAAGCAGCTAAAGAGATGCTTGCTAATT |
| 297 | TGAATCAGTAAAAACTTGTCAAAAGCAGCTAAAGAGATGCTTACTAATT |
| SIMON | TGAATCAGTAGCAAGCTTAGTAAAAGCGGCTCAAGAAGCACTAACTAATT |
| E61 | TGAATCAGTAACAAGCTTGTCAAAAGCAGCTAAAGAATCACTAACCAATT |
| ORTH | TGAATCAGTAGCAAGCTTGTCAAAAGCGGCTCAAGAAGCATCAGCTAATT |
| ACA1 | TAAATCAGTAGTGGAAGGTTTGTCAAAAGCAGCTCAAGAAGCACTAACTAATT |
| H9 | TAAATCAGTCAGTAGAAAGCTTGTCAAAAGCAGCTCAAGAATCACTAACCAATT |
| J1 | TAAATCAGTAGAAGGTTTGTTAAAAGCAGCTAAAGAAGCACTAACTAATT |
| JSB | TGAATCAGTAGAAGGTTTGTTAAAAGCAGCTAAAGAAGCACTAACTAATT |
| VS461 | TAAATCAGTAGAAAGCTTGTCAAAAGCAGCTAAAGAAGCATTAAGTAATT |
| M57 | TGAATCAGTAGAAAGCTTGGCAAAAGCAGCAGGCGCAGCATTAGCTAATT |
| M | TGAATCAGTAGAAAGCTTGGCAAAAGCAGCAGGCGCAGCATTAGCTAATT |
| VSDA | TAAATCAGTAGAAAATTGTCAAAAGCAGCTCAAGAAGCACTAGCTAATT |
| NBS23a | TGAATCAGTAGAAAATTGTCAAAAGCAGCAGGCGCAGCAGCACTAGCTAATT |
| 20047 | TAAATCAGTAGAAAGTTGTCAAAAGCAGCAGGCGCAGCACTAACTAATT |
| KL10 | TGAATCAGTAAAAGTTGCTAAAAGCAGCAGGCGCAGCATTAAGCAATT |
| IP90 | GAAATCAGTAAAAGCTTGTCAAAAGCAGCAGGCGCAAGCATCAAGCAATT |
| NBS1AB | GAAATCAGTAGAAAGCTTGGCAAAAGCAGCAGGCGCAAGCATCAAGCAATT |
| BITS | TAAATCAGTAGAAAGCTTGTCAAAAGCAGCAGGCGCAAGCATCAGCTAATT |
| KL11 | TGAATCATTAGAAAATGTCAAAAGCAGCAGGCGCAAGCATCAGCTAATT |
| PBI | TAAATCACTAGAAAAGCTTGTCAAAAGCAGCAGGCGCAAGCATTAACTAATT |
| H13 | TGAATCAGTAGAAAGCTTGGCAAAAGCAGCAGGCGCAGCACTAGCTAATT |
| | * *   * *  ***** * ** * *** |

Fig. 8a-12

```
28691   CTGTTAAAGAGCTTACAAGTCCTATTGTGGCAGAAAGTCCAAAAAAACCTTAA
2591    CAGTTAAAGAAGCTTACAAGTCCTGTTGTGGCAGAAAATCCAAAAAAAACCTTAA
IP2     CAGTTAAAGAGCTTACAAGCCCTGTTGTGGCAGAAAGTCCAAAAAAACCTTAA
25015   CA
ZS7     CAGTTAAAGAGCTTACAAGTCCTGTTGTGGTAGAAAGTCCAAAAAAACCTTAA
297     CAGTTAAAGAGCTTACAAGCCCTGTTGTGGCAGAAAGTCCAAAAAAAACCTTAA
SIMON   CA
E61     CAGTTAAAGAGAACTTACAAGTCCTGTTGTAGCAGAAACTCCAAAAAAACCTTAA
ORTH    CAGTTAAAGAGCTTACAAGTCCTGTTGTAGCAGAAAGTCCAAAAAAACCTTAA
ACA1    CAGTTAAAGAGCTTACAAGTCCTGTTGTAGCAGAAAGTCCAAAAAAAACCTTAA
H9      CAGTTAAAGAGCTTACAACCCTGTTGTAGCAGAAAGTCCAAAAAAACCTTAA
J1      CA
JSB     CAGTTAAAGAGAACTTACAAGTCCTGTTGTAGCAGAAAGTCCAAAAAAACCTTAA
VS461   CAGTTAAAGAGCTTACAAGTCCTGTTGTAGCAGAAAGTCCAAAAAAACCTTAA
M57     CAGTTAAAGAGCTTACAAGTCCTGTTGTGGCAGAAACTCCAAAAAAACCTTAA
W       CAGTTAAAGAGCTTACAAGTCCTGTTGTGTGGCAGAAACTCCAAAAAAACCTTAA
VSDA    CAGTTAAAGAGCTTACAAGTCCTGTTGTGGCAGAAACTCCAAAAAAAACCTTAA
NBS23a  CAGTTCAAGAGCTTACAAGTCCTGTTGTGGCAGAAACTCCAAAAAAACCTTAA
20047   CAGTTAAAGAGCTTACAAATCCTGTTGTGGCAGAAACTCCAAAAAAACCTTAA
KL10    CAGTTAAAGAGCTTACAAGTCCTGTTGTGGCAGAAACTCCAAAAAAACCTTAA
IP90    CAGTTAAAGAGCTTACAAGTCCTGTTGTGGCAGAAGCTCCAAAAAAACCTTAA
NBS1AB  CA
BITS    CAGTTAAAGAGCTTACAAGTCCTGTTGTGGCAGAAACTCCAAAAAAAACCTTAA
KL11    CAGTTAAAGAGCTTACAAGTCCTGTTGTGGCAGAAACTCCAAAAAAAACCTTAA
PBI     CA
H13     CAGTTCAAGAGCTTACAAGCCCTGTTGTGGCAGAAACTCCAAAAAAACCTTAA
        * *** **** ******   *** ***** * ***** **************
```

Fig. 9-1

```
2591    CNNSGKDGNT-SANSADESVKGPNLTEISKKITESNAVVLAVKEVETLLASIDEVAKKAIGNLI
B31     CNNSGKDGNT-SANSADESVKGPNLTEISKKITDSNAVLLAVKEVEALLSSIDEIAAKAIGKKI
25015   CNNSGKDGNAASTNPADESVKGPNLTEISKKITDSNTVVLAVKEVEALLTSIDELATKAIGKKI
ZS7     CNNSGKDGNT-SANSADESVKGPNLTEISKKITDSNAVLLAVKEVEALLSSIDELA-KAIGKKI
297     CNNSGKDGNT-SANSADESVKGPNLTEISKKITESNAVVLAVKEVETLLTSIDELA-KAIGKKI
SIMON   CNNSGKGGDSTSTNPADESAKGPNLTEISKKITNSNAFVLAVKEVETLVASIDELATKAIGKKI
E61     CNNSGKGGDSTSTNPADESAKGPNLTEISKKITDSNAFVLAVKEVETLVASIDELATKAIGKKI
ORTH    CNNSGKGGDSASTNPADESAKGPNLTEISKKITDSNAFVLAVKEVETLVSSIDELATKAIGKKI
ACAI    CNNSGKGGDSASTNPADESAKGPNLTEISKKITDSNAFVLAVKEVETLVSSIDELANKAIGKKI
H9      CNNSGKGGDSASTNPADESAKGPNLTEISKKITDSNAFVLAVKEVETLVSSIDELAAQAIGKKI
J1      CNNSGKGGDSASTNPTDESAKGPNLTEISKKITDSNAFVLAVKEVETLVSSIDELANKAIGKKI
JSB     CNNSGKGGDSASTNPADESAKGPNLTEISKKITDSNAFVLAVKEVETLVLSIDELAKKAIGQKI
VS461   CNNSGKGGDIASTNP-DESAKGPNLTEISKKITDSNAVVLAVKEVEALLSSIDELA-KTIGKKI
M57     CNNSG--GDTASTNP-DESAKGPNLTVISKKITDSNAFVLAVKEVEALISSIDELANKAIGKVI
W       CNNSG--GDTASTNP-DESAKGPNLIEISKKITDSNAFVLAVKEVEALISSIDELANKAIGKKI
VSDA    CNNSG--GDTASTNP-DESAKGPNLTVISKKITDSNAFVLAVKEVEALLSSVDELA-KAIGKKI
NBS23A  CNNSG--GDTASTNP-DESAKGPDLTVISKKITDSNAFVLAVKEVEALLSSVDELA-KAIGKKI
20047   CNNSG--GDTASTNP-DESAKGPNLTEISKKITDSNAFVLAVKEVEALLSSIDELA-KAIGQRI
KL10    CNNSG--GDTASTNP-DESVKGPNLTEISKKITDSNAFVLAVKEVEALISSIDELA-KGIGKKI
IP90    CNNSG--GDTASTNP-DESAKGPNLIEISKKITDSNAFVLAVKEVEALLSSIDELA-KAIGQKI
NBS1AB  CNNSG--GDSASTNP-DESAKGPDLTVISKKITDSNAFVLAVKEVEALLSSIDELA-KAIGQKI
BITS    CNNSG--GDSASTNP-DESAKGPNLIEISKKITDSNAVVLAVKEVEALLSSIDELS-KAIGKKI
KL11    CNNSG--GDSASTNP-DESAKGPDLTVISKKITDSNAVVLVKEVEALLSSIDELS-KAIGKKI
PBI     CNNSG--GDSASTNP-DESAKGPNLTVISKKITDSNAFLLAVKEVEALLSSIDELS-KAIGKKI
        ****  . *  ***  * ***  * ***  ** ***  * ****  *** ** *   ** ***
```

Fig.9-2

```
2591    AQN-GLNAGANQ-NGSLLAGAYVISTLIAEKLDGL-KNSEELKEKIEDAKKCNKAFTDKLKSSH
B31     HQNNGLDTENNH-NGSLLAGAYAISTLIKQKLDGL-KN-EGLKEKIDAAKKCSETFTNKLKEKH
25015   HQNNGLDTENNH-NGSLLAGAYAISTLITQKLGGL-KN-EELKEKIAAVKKCSEEFTNKLKSSH
2S7     KNDGSLGDEANH-NESLLAGAYTISTLITQKLSKL-NGSEGLKEKIAAAKKCSEEFSTKLKDNH
297     KNDVSLDNEADH-NGSLISGAYLISTLITKKISAI-KDSGELKAEIEKAKKCSEEFTAKLKGEH
SIMON   KNDGTLENEANH-NGSLLAGAYAISNLIKQKLDGL-KGLEGLNKEIAEAKNCSEAFTKKLKEKH
E61     KNDGTLDNEANH-NGSLLAGAYAISTLITQKLSVL-NS-EELKAEIVKAKKCSEDFTKKLKDKH
ORTH    QQNNGLGANADK-NGSLLAGAYAISTLITEKLKAL-KNSGELKAKIEDAKKCSEDFTKKLAAGH
ACAI    QQN-GLGAEANR-NESLLAGVHEISTLITEKLSKL-KNSGELKAKIEDAKKCSEEFTNKLRVSH
H9      QNN-GLTAEQNQ-NGSLLAGAYAISALITKKLDELTKNSGELKGEVEKAKKCSEEFTNKLKGGH
J1      QNN-GLSAEQNQ-NGSLLAGAYAISTLIKQKLDGL-KGLEGLNKEITEAKKCSQDFINKLKGGH
JSB     DNNGLAALNNQ-NGSLLAGAYAISTLITEKLSKL-KNLEELKTEIAKAKKCSEEFTNKLKSGH
VS461   EAN-GLGNEADK-NGSLLAGAYAISTLIKQKLDGL-KGLEGLNKEIAEAKKCSEAFTKKLQDSN
M57     HQNNGLNANAGQ-NGSLLAGAYAISTLITEKLSKL-KNSEELNKKIEEAKNHSEAFTNRLKGSH
W       NQN-GLDADANH-NGSLLAGAHAISTLIKQKTDGL-KDLEGLSKEIAKVKECSDKFTKKLTDSH
VSDA    HQNNGLDTLSNQ-NGSLLAGAYAISTLITKKLDGL-KGSEGLKAEIAEAKKCSEDFTKKLKEKH
NBS23A  DNNTGLSANQNH-NTSLLAGAYSISTLITEKLSKL-KNLEGLKAEIAEAKKCSEDFTKKLKDNH
20047   QQN-GLVADAGH-NSALLAGAHEISILITQKLDGL-KGLEGLKAEIAEAKKYSEAFTKKLKDNH
KL10    DQNSGLAAATQNKNTSLLAGAYVSALIKQKLDGL-QGPEGLNKEIEAAKKCSEAFTNKLKEKH
IP90    DQNNGLAAATQDKNTSLLAGAYAISALIKQKLDGL-QGPEGLNKEIEAAKKCSEAFTNKLKEKH
NBS1AB  DQNNGLAAATQDKNTSLLAGAYAISALIKQKLDGL-QGPEGLNKEIEAAKKCSEAFTNKLKEKH
BITS    DRNNGLAVEANF-NTSLLAGAYTISTLITKKLDELIKNSGELKGEVEKAKNCSEAFTNKLKEKH
KL11    RNDGTLDNEAN-RNESLIAGAYEISKLITQKLSVL--NSEELKEKIKEAKDCSEKFTKLRDSH
PBI     KNDGTLDNEAN-RNESLIAGAYEISKLITQKLSVL--NSEELKEKIKEAKDCSQKFTKLKDSH
                 *      *   *                         *      *        *
```

Fig. 9-3

```
2591      AELGIAN-GAASDANAKAAILKTNGT-KDKGAQELEKLFESVKNLSKAAQETLNNS
B31       TDLGKEG---VTDADAKEAILKTNGT-KTKGAEELGKLFESVEVLSKAAKEMLANS
25015     TELGKQD---AQDDDAKKAILRTHNT-KDKGAEELDKLFKPVENLSKAAKEMLSNS
ZS7       AQLGIQG---VTDENAKKAILKANAAGKDKGVEELEKLSGSLESLSKAAKEMLANS
297       TDLGKEG---VTDDNAKKAILKTNN-DKTKGADELEKLFESVKNLSKAAKEMLTNS
SIMON     TDLGKEN---ATDEDAKKAILKTDAT-KDKGAAELEKLSESVASLVKAAQEALTNS
E61       TELGKQD---ANDDDAKKAILKTNGD-KTLGAAELEKLSESVTSLSKAAKESLTNS
ORTH      AQLGIDG---ATDNDSKEAILKTNGT-KTKGAEELVKLSESVASLSKAAQEASANS
ACAI      ADLGKQG---VNDDDAKKAILKTNAD-KTKGAEELGKLFKSVEGLVKAAQEALTNS
H9        AELGLAA---ATDENAKKAILKTNGT-KDKGAEELEKLFKSVESLAKAAKESLTNS
J1        AELGLVA---ATDANAKAAILKTNGD-KTKGADEFEKLFKSVEGLLKAAQEALTNS
JSB       ADLGKQD---ATDDHAKAAILKTHAT-TDKGAKEFKDLFESVEGLLKAAQVALTNS
VS461     ADLGKHN---ATDADSKEAILKTNGT-KTKGAKELEELFKSVESLSKAAKEALSNS
M57       AQLGVAA-AT--DDHAKEAILKSN PT-KDKGAKELKDLSESVESLAKAAQAALANS
W         AQLGAVG-GAINDDRAKEAILKTHGT-NDKGAKELKELSESVESLAKAAQAALANS
VSDA      TELGVA---AATDDNAKKAILKANGD-KTLGVEELEKLFKSVEKLSKAAQEALANS
NBS23A    ADLGVAGNGASTDENAQKAILKTNAI-VDKGAKDLKELFESVEKLSKAAQEALANS
20047     AQLGIQ-NGASLDDEAKKAILKTHPT-KDKGAEELEKLFKSVESLSKAAQEALTNS
KL10      AELGVNG-GDTTDDNAKAAIFKTHPT-KDKGVEDLEKLSESVKSLLKAAQAALSNS
IP90      QDLGVAN-GDTTDDNNAKAAILKTHGT-EDKGVKELKDLLKSVESLAKAAQAASSNS
NBS1AB    QDLGVAN-GDTTDNNAKAAILKTHGT-EDKGVKELKDLLKSVESLAKAAQAASSNS
BITS      QELAVAA-GAATDIDAKKAILKTNRD-KDLGADELGKLFKSVESLSKAAQEASANS
KL11      AELGIQN---VQDDNAKRAILKTHGN-KDKGAKELKELSESLEKLSKAAQAALANS
PBI       AELGIQS---VQDDNAKKAILKTHGT-KDKGAKELELELFKSLESLSKAAQAALTNS
          .*.         *      ** ....   *  . .  *   *   ***  *    **
```

Fig. 9a-1

```
28691   CNNSGKDGNA-SANSADESVKGPNLTEISKKITESNAVVLAVKEVETLLASIDELATKAIGKKI
2591    CNNSGKDGNT-SANSADESVKGPNLTEISKKITESNAVVLAVKEVETLLASIDEVAKAIGNLI
IP2     CNNSGKDGNT-SANSADESVKGPNLTEISKKITDSNAVLLAVKEVETLLASIDEIAAQAIGKKI
25015   CNNSGKDGNA-ASTNPADESVKGPNLTEISKKITDSNTVVLAVKEVEALLTSIDELATKAIGKKI
ZS7     CNNSGKDGNA-SANSADESVKGPNLTEISKKITDSNAVLLAVKEVEALLSSIDELA-KAIGKKI
297     CNNSGKDGNT-SANSADESVKGPNLTEISKKITESNAVVLAVKEVETLLTSIDELA-KAIGKKI
SIMON   CNNSGKGGDSTSTNPADESAKGPNLTEISKKITNSNAFVLAVKEVETLVASIDELATKAIGKKI
E61     CNNSGKGGDSTSTNPADESAKGPNLTEISKKITDSNAFVLAVKEVETLVASIDELATKAIGKKI
ORTH    CNNSGKGGDSASTNPADESAKGPNLTEISKKITDSNAFVLAVKEVETLVSSIDELATKAIGKKI
ACAI    CNNSGKGGDSASTNPADESAKGPNLTEISKKITDSNAFVLAVKEVETLVSSIDELANKAIGKKI
H9      CNNSGKGGDSASTNPADESAKGPNLTEISKKITDSNAFVLAVKEVETLVSSIDELAAQAIGKKI
J1      CNNSGKGGDSASTNPTDESAKGPNLTEISKKITDSNAFVLAVKEVETLVSSIDELANKAIGKKI
JS3     CNNSGKGGDSASTNPADESAKGPNLTEISKKITDSNAFVLAVKEVETLVLSIDELAKKAIGQKI
VS461   CNNSGKGGDIASTNP-DESAKGPNLTEISKKITDSNAVVLAVKEVEALLSSIDELA-KTIGKKI
M57     CNNSG---GDTASTNP-DESAKGPNLTVISKKITDSNAFVLAVKEVEALISSIDELANKAIGKVI
W       CNNSG---GDTASTNP-DESAKGPNLIEISKKITDSNAFVLAVKEVEALLSSIDELANKAIGKKI
VSDA    CNNSG---GDTASTNP-DESAKGPNLTEISKKITDSNAFVLAVKEVEALLSSVDELA-KAIGKKI
NBS23A  CNNSG---GDTASTNP-DESAKGPNLTEISKKITDSNAFVLAVKEVEALISSVDELA-KAIGKKI
20047   CNNSG---GDTASTNP-DESVKGPNLTEISKKITDSNAFVLAVKEVEALISSIDELA-KAIGQRI
KL10    CNNSG---GDTASTNP-DESAKGPNLTEISKKITDSNAFVLAVKEVEALLSSIDELA-KGIGKKI
IP90    CNNSG---GDTASTNP-DESAKGPDLTVISKKITDSNAFVLAVKEVEALLSSIDELA-KAIGQKI
NBS1AB  CNNSG---GDSASTNP-DESAKGPDLTVISKKITDSNAFVLAVKEVEALLSSIDELA-KAIGQKI
BITS    CNNSG---GDSASTNP-DESAKGPDLTVISKKITDSNAFVLAVKEVEALLSSIDELA-KAIGQKI
KL11    CNNSG---GDTASTNP-DESAKGPNLTVISKKITDSNAVVLVVKEVEALLSSIDELS-KAIGKKI
PBI     CNNSG---GDSASTNP-DESAKGPNLTVISKKITDSNAFLLAVKEVEALLSSIDELS-KAIGKKI
H13     CNNSG---GDTASTNP-DESTKGPNLIEISKKITDSNAVVLAVKEVEALISSIDELA-KAIGKKV
        ****    *   * *  ** ***   * ******  ****  ***  ***      **    *
```

Fig.9a-2

```
28691  GNN-GLEANQSK-NTSLLSGAYAISDLIAEKLNVL-KN-EELKEKIDTAKQCSTEFTNKLKSEH
2591   AQN-GLNAGANQ-NGSLLAGAYVISTLIAEKLDGL-KNSEELKEKIEDAKKCNKAFTDKLKSSH
IP2    HQNNGLDTENNH-NGSLLAGAYAISTLIKQKLDGL-KN-EGLKEKIDAAKKCSETFTNKLKEKH
25015  HQNNGLDTENNH-NGSLLAGAYAISTLIITQKLGGL-KN-EELKEKIAAVKKCSEEFTNKLKSSH
ZS7    KNDGSLGDEANH-NESLLAGAYTISTLIITQKLSKL-NGSEGLKEKIAAAKKCSEEFSTKLKDNH
297    KNDVSLDNEADH-NGSLISGAYLISTLITKKISAI-KDSGELKAEIEKAKKCSEEFTAKLKGEH
SIMON  KNDGTLENEANH-NGSLLAGAYAISNLIKQKLDGL-KGLEGLNKEIAEAKNCSEAFTKKLKEKH
E61    KNDGTLDNEANH-NGSLLAGAYAISTLITQKLSVL-NS-EELKAEIVKAKKCSEDFTKKLKDKH
ORTH   QQNNGLGANADK-NGSLLAGAYAISTLITEKLKAL-KNSGELKAKIEDAKKCSEDFTKKLAAGH
ACAI   QQN-GLGAEANR-NESLLAGVHEISTLIITEKLSKL-KNSGELKAKIEDAKKCSEEFTNKLRVSH
H9     QNN-GLTAEQNQ-NGSLLAGAYAISALITKKLDELTKNSGELKGEVEKAKKCSEEFTNKLKGGH
J1     QNN-GLSAEQNQ-NGSLLAGAYAISTLIKQKLDGL-KGLEGLNKEITEAKKCSQDFINKLKGGH
JS3    DNNNGLAALNNQ-NGSLLAGAYAISTLITEKLSKL-KNLEELKTEIAKAKKCSEEFTNKLKSGH
VS461  EAN-GLGNEADK-NGSLLAGAYAISTLIKQKLDGL-KGLEGLNKEIAEAKKCSEAFTKKLQDSN
M57    HQNNGLNANAGQ-NGSLLAGAYAISTLITEKLSKL-KNSEELNKKIEEAKNHSEAFTNRLKGSH
W      NQN-GLDADANH-NGSLLAGAHAISTLIKQKTDGL-KDLEGLSKEIAKVKECSDKFTKKLTDSH
VSDA   HQNNGLDTLSNQ-NGSLLAGAYAISTLITKKLDGL-KGSEGLKAEIAEAKKCSEDFTKKLKEKH
NBS23A DNNTGLSANQNH-NTSLLAGAYSISTLITEKLSKL-KNLEGLKAEIAEAKKCSEDFTKKLKDNH
20047  QQN-GLVADAGH-NSALLAGAHEISILITQKLDGL-KGLEGLKAEIAEAKKYSEAFTKKLKDNH
KL10   DQNSGLAAATQNKNTSLLAGAYAVSALIKQKLDGL-QGPEGLNKEIEAAKKCSEAFTNKLKEKH
IP90   DQNNGLAAATQDKNTSLLAGAYAISALIKQKLDGL-QGPEGLNKEIEAAKKCSEAFTNKLKEKH
NBS1A3 DQNNGLAAATQDKNTSLLAGAYAISALIKQKLDGL-QGPEGLNKEIEAAKKCSEAFTNKLKEKH
BITS   DRNNGLAVEANF-NTSLLAGAYTISTLIKKLDELIKNSGELKEKIKEAKDCSEKFTTKLRDSH
KL11   RNDGTLDNEANR-NESLLAGAYEISKLITQKLSVL--NSEELKEKIKEAKDCSEKFTTKLRDSH
PBI    KNDGTLDNEANR-NESLLAGAYEISKLITQKLSVL--NSEELKEKIKEAKDCSQKFTTKLKDSH
H13    EAN-GLGNEADR-NTSLLAGAHEISILITQKLTAL-KDSGGLKAEIAEAKKCSEAFTKKLKDNN
              *    *       *. *:   .   *   *.  .    *  :   .*.. ** **::.
```

Fig. 9a-3

```
28691   AVLGLDN----LTDDNAQRAILKKHAN-KDKGAAELEKLFKAVENLSKAAQDTLKNAVKELTSPIVAESPKKP
2591    AELGIAN-GAASDANAKAAILKTNGT-KDKGAQELEKLFESVKNLSKAAQETLNNSVKELTSPVVAENPKKP
IP2     TDLGKEG----VTDADAKEAILKTNGT-KTKGAEELGKLFESVEVLSKAAKEMLANSVKELTSPVVAESPKKP
25015   TELGKQD----AQDDDAKKAILRTHNT-KDKGAEELDKLFKPVENLSKAAKEMLSNS
ZS7     AQLGIQG----VTDENAKKAILKANAAGKDKGVEELEKLSGSLESLSKAAKEMLANSVKELTSPVVESPKKP
297     TDLGKEG----VTDDNAKKAILKTNND-KTKGADELEKLFESVKNLSKAAKEMLTNSVKELTSPVVAESPKKP
SIMON   TDLGKEN----ATDEDAKKAILKTDAT-KDKGAAELEKLFKSVESLSKAAKESLTNSVKELTSPVVAETPKKP
E61     TELGKQD----ANDDDAKKAILKTNGD-KTLGAAELEKLSESVTSLSKAAKESLTNSVKELTSPVVAESPKKP
ORTH    AQLGIDG----ATDNDSKEAILKTNGT-KTKGAEELVKLSESVASLSKAAQEASANSVKELTSPVVAETPKKP
ACAI    ADLGKQG----VNDDDAKKAILKTNAD-KTKGAEELGKLFKSVEGLVKAAQEALTNSVKELTSPVVAESPKKP
H9      AELGLAA----ATDENAKKAILKTNGT-KDKGAEELEKLFKSVESLAKAAKESLTNSVKELTNPVVAESPKKP
J1      AELGLVA----ATDANAKAILKTNGD-KTKGADEFEKLFKSVEGLLKAAQEALTNS
JSB     ADLGKQD----ATDDHAKAAILKTHAT-TDKGAKEFKDLFESVEGLLKAAQVALTNSVKELTSPVVAETPKKP
VS461   ADLGKHN----ATDADSKEAILKTNGT-KTKGAEELEELFKSVESLSKAAKEALSNSVKELTSPVVAESPKKP
M57     AQLGVAA----ATDDHAKEAILKSNPT-KDKGAKELKDLSESVESLAKAAQEALANSVKELTSPVVAETPKKP
W       AQLGAVG-GAINDDRAKEAILKTHGT-NDKGAKELKELSESVESLAKAAQAALANSVKELTSPVVAETPKKP
VSDA    TELGVAA----ATDDNAKKAILKANGD-KTLGVEELEKLFKSVEKLSKAAQEALANSVQELTSPVVAETPKKP
NBS23A  ADLGVAGNGASTDENAQKAILKTNAI-VDKGAKDLKELFESVEKLSKAAQEALANSVKELTSPVVAETPKKP
20047   AQLGIQ-NGASLDDEAKKAILKTNVD-KTKGAEELEKLFKSVESLSKAAQEALTNPVVAETPKKP
KL10    AELGVNG-GDTTDDNAKAAIFKTHPT-KDKGVEDLEKLSESVKSLLKAAQAALSNSVKELTSPVVAEAPKKP
IP90    QDLGVAN-GDTTDNNAKAAILKTHGT-EDKGVKELKDLLKSVESLAKAAQAASNS
NBS1AB  QDLGVAN-GDTTDNNAKAAILKTHGT-EDKGVKELKDLLKSVESLAKAAQAASSNS
BITS    QELAVAA-GAATDIDAKKAILKTNRD-KDLGADELGKLFKSVESLSKAAQEASANSVKELTSPVVAETPKKP
KL11    AELGIQN----VQDDNAKRAILKTHGN-KDKGAKELKELSESLEKLSKAAQAALANSVKELTSPVVAETPKKP
PBI     AELGIQS----VQDDNAKKAILKTHGT-KDKGAKELEELFKSLESLSKAAQAALTNS
H13     AQLGIQN----VQDVEAKKAILKTNGD-ISKGAKELKELFESVESLAKAAQAALANSVQELTSPVVAETPKKP
         *.       *          *   *.  *                       *.           *  ****
```

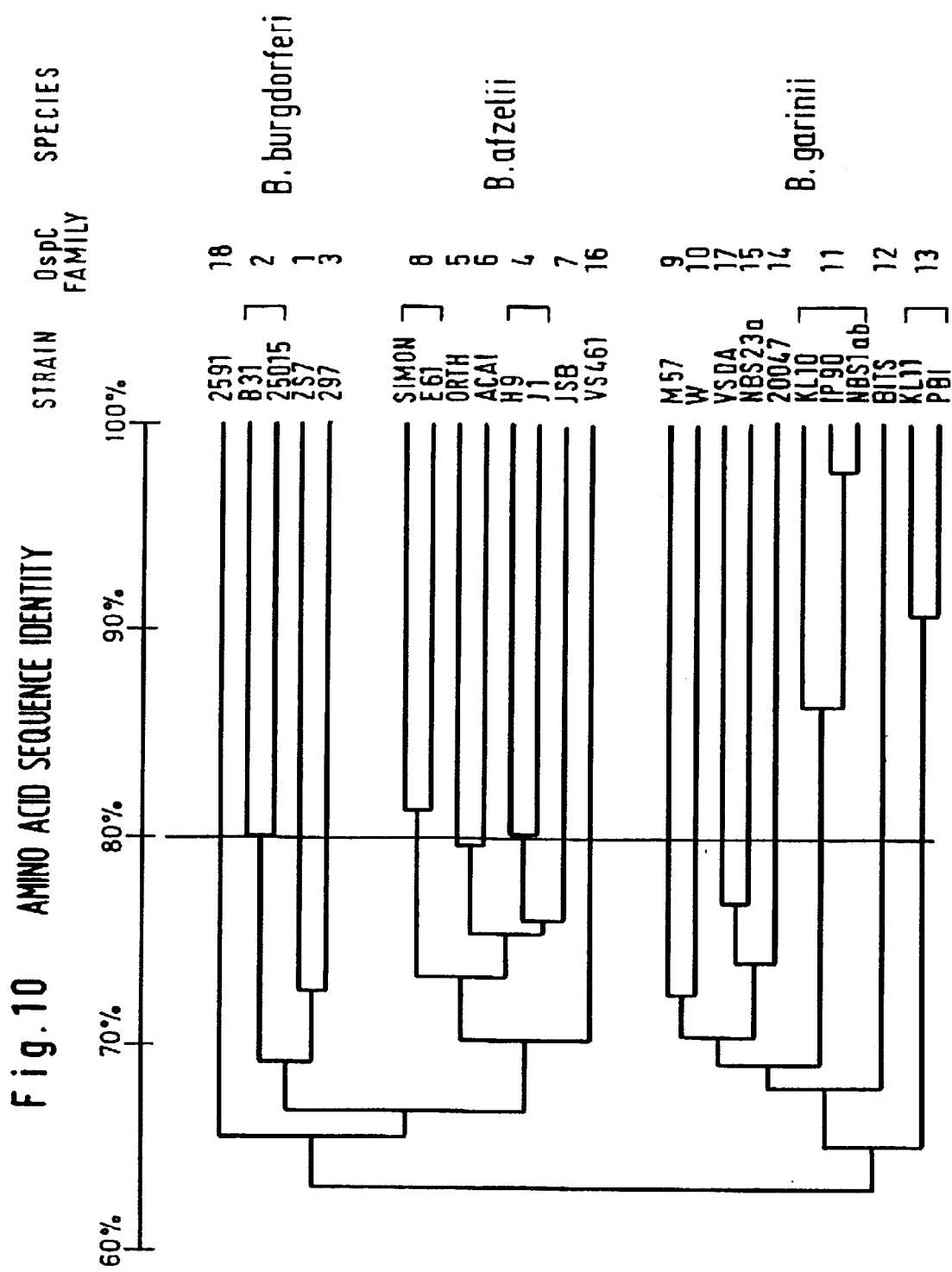

Fig. 11

| OspC Families and Type Strains ||
|---|---|
| OspC Family | Representative |
| 1 | ZS 7 |
| 2 | B31 |
| 3 | 297 |
| 4 | H9 |
| 5 | Orth |
| 6 | ACA1 |
| 7 | JSB |
| 8 | E61 |
| 9 | M57 |
| 10 | W |
| 11 | KL10 |
| 12 | BITS |
| 13 | KL11 |
| 14 | 20047 |
| 15 | NBS23a |
| 16 | VS461 |
| 17 | VSDA |
| 18 | 2591 |
| 19 | H13 |
| 20 | 28691 |

Biological and geographical origin of Borrelia strains and association with CMAT and OspC types  Fig. 12a

| STRAIN | CMAT | FAMILY | RFLP | SEROVAR | HUMAN | TICK | ANIMAL | COUNTRY |
|---|---|---|---|---|---|---|---|---|
| IRS | 1.1.01 | 1 | 1 | NT | | I.ricinus | | Switzerland |
| ZS7 | 1.1.02 | 1 | 1 | NT | | I.ricinus | | Germany |
| DK7 | NT(1) | 1 | 1 | NA | | | | Denmark |
| VS215 | 1.1.02 | 1 | 1 | 01 | Skin (ACA) | I.ricinus | | Switzerland |
| VS219 | 1.1.02 | 1 | 1 | 01 | | I.ricinus | | Switzerland |
| 27985 | 1.2.04 | 2 | 2 | 02 | | I.dammini | | United States |
| B31 | 1.2.04 | 2 | 2 | 02 | | I.dammini | | United States |
| HB4 | 1.2.04 | 2 | 2 | 02 | Blood | | | United States |
| IP1 | 1.2.04 | 2 | 2 | 02 | CSF | | | France |
| IP2 | 1.2.04 | 2 | 2 | 02 | CSF | | | France |
| 26816 | 1.2.04 | 2 | 2 | 02 | | | Vole | United States |
| HB1 | 1.2.04 | 2 | 2 | 02 | Blood(Myositis) | | | Austria |
| H3 | 1.2.04 | 2 | 2 | 02 | Skin (EM) | | | Austria |
| IP21 | 1.2.04 | 2 | 2 | NT | | I.persulcatus | | Russia |
| 25015 | 2.2.11 | 2 | 2 | 02 | | I.dammini | | United States |
| 297 | 1.2.04 | 2 | 3 | NT | CSF | | | United States |
| H9 | 3.2.13 | 4 | 4 | 03 | Skin | | | Austria |
| H10 | 3.2.13 | 4 | 5 | 03 | Skin | | | Austria |
| H5 | 3.2.13 | 4 | 5 | 03 | Skin | | | Austria |
| H1 | 3.2.13 | 4 | 5 | 03 | Skin | | | Austria |
| J1 | 3.1.12 | 4 | 6 | 03 | | I.persulcatus | | Japan |
| H7 | 3.2.13 | 5 | 7 | 04 | Skin (ACA) | | | Austria |
| Gaultier | 3.2.13 | 5 | 7 | 04 | Skin (EM) | | | Italy |
| H11 | 3.2.13 | 5 | 7 | 04 | Skin | | | Austria |
| Orth | 3.2.13 | 5 | 7 | 04 | | I.ricinus | | Austria |

Fig. 12b

| STRAIN | CMAT | FAMILY | RFLP | SEROVAR | HUMAN | TICK | ANIMAL | COUNTRY |
|---|---|---|---|---|---|---|---|---|
| König | 3.2.13 | 6 | 8 | 05 | Skin | I.ricinus | | Austria |
| H2 | 3.2.13 | 6 | 8 | 05 | Skin (ACA) | | | Austria |
| ACA1 | 3.2.14 | 6 | 8 | NR | Skin | | | Sweden |
| H15 | 3.2.13 | 6 | 8 | 06 | Skin | | | Austria |
| H6 | 3.2.13 | 6 | 8 | 05 | Skin | | | Austria |
| H14 | 3.2.13 | 6 | 8 | 05 | Skin (ACA) | | | Austria |
| JSB | 3.2.13 | 7 | 9 | 07 | Skin | | | Slovenia |
| PKO | 3.2.13 | 7 | 9 | 07 | Skin (EM) | | | Germany |
| DK26 | NT (3) | 7 | 9 | NA | Skin (EM) | | | Denmark |
| P1H | 3.2.13 | 7 | 9 | 07 | Skin (ACA) | | | Germany |
| H12 | 3.2.13 | 7 | 9 | NT | Skin (ACA) | | | Austria |
| E61 | 3.2.13 | 8 | 10 | 08 | Skin (EM) | | | Czech.Republic |
| Simon | 3.2.13 | 8 | 11 | 09 | Skin | | | Austria |
| IR210 | 4.2.18 | 9 | 12 | 10 | | I.ricinus | | Russia |
| KL5 | 4.2.18 | 9 | 12 | 10 | | I.ricinus | | Czech.Republic |
| M57 | 4.2.18 | 9 | 12 | 10 | CSF | | | Czech.Republic |
| H4 | 4.2.22 | 10 | 12 | 11 | Skin (EM) | | | Austria |
| W | 4.2.22 | 10 | 13 | 11 | CSF | | | Austria |
| MK6 | 4.2.18 | 11 | 14 | 12 | | I.ricinus | | Hungary |
| KL10 | 4.2.18 | 11 | 14 | 12 | | I.ricinus | | Czech.Republic |
| NBS1ab | 4.2.18 | 11 | 15 | 13 | Neuroborrelios | | | Sweden |
| Lithuania | 4.2.19 | 11 | 15 | 13 | | I.ricinus | | Lithuania |
| IP90 | 2.1.09 | 11 | 16 | 13 | | I.persulcatus | | Russia |
| VSBM | 4.2.18 | 12 | 17 | NR | CSF | | | Switzerland |
| BITS | 4.2.17 | 12 | 17 | NR | | I.ricinus | | Italy |
| PBI | NT(4) | 13 | 18 | NA | CSF | | | Germany |
| DK6 | NT(4) | 13 | 18 | NA | CSF | | | Denmark |

Fig. 12c

| STRAIN | CMAT | FAMILY | RFLP | SEROVAR | HUMAN | TICK | ANIMAL | COUNTRY |
|---|---|---|---|---|---|---|---|---|
| VSBP | 4.2.18 | 13 | 19 | NR | CSF | | | Switzerland |
| KL11 | 4.2.18 | 13 | 19 | NR | | I.ricinus | | Czech.Republic |
| 871104 | 4.2.17 | 13 | 19 | NT | CSF | | | Sweden |
| KL6 | 4.2.18 | 13 | 19 | NR | | I.ricinus | | Czech.Republic |
| MK5 | 4.2.18 | 13 | 19 | NT | | I.ricinus | | Hungary |
| E180 | 4.2.18 | 14 | 20 | 14 | Skin (EM) | | | Czech.Republic |
| VS102 | 4.2.18 | 14 | 20 | 14 | | I.ricinus | | Switzerland |
| VS185 | 4.2.18 | 14 | 20 | 14 | | I.ricinus | | Switzerland |
| 20047 | 2.1.08 | 14 | 20 | 14 | | I.ricinus | | France |
| NBS23a | 4.3.23 | 15 | 21 | 15 | Neuroborreliosis | | | Sweden |
| NBS23b | 4.3.23 | 15 | 21 | 15 | Neuroborreliosis | | | Sweden |
| VS461 | 3.2.13 | 16 | 22 | 16 | | I.ricinus | | Switzerland |
| C78 | 3.2.13 | 16 | 22 | NT | Blood (NB) | | | Czech.Republic |
| KC90 | 3.2.13 | 16 | 22 | NT | Blood (Cardiac) | | | Czech.Republic |
| E51 | 3.2.13 | 16 | 22 | 16 | Skin (EM) | | | Czech.Republic |
| VSDA | 4.2.18 | 17 | 23 | NR | CSF | | | Switzerland |
| 2591 | NT(1) | 18 | 24 | NA | | | White-footed mouse | United States |
| H13 | 4.2.20 | 19 | 25 | NR | Skin | | | Austria |
| H8 | 4.2.20 | 19 | 25 | NR | Skin | | | Austria |
| 28691 | 1.2.04 | 20 | 26 | 16 | | I.dammini | | United States |
| Son188 | 1.2.03 | 99 | 27 | NT | | I.pacificus | | United States |
| 275579 | 1.2.04 | 99 | 27 | NT | | I.dammini | | United States |
| 21347 | 1.2.05 | 99 | 28 | NT | | | White-footed mouse | United States |
| 26815 | 1.2.06 | 99 | 29 | NT | | | Chipmunk | United States |
| 28354 | 1.2.07 | 99 | 30 | NR | | I.dammini | | United States |
| 19857 | 4.1.15 | 99 | 31 | NT | | | Rabbit | United States |
| 19952 | 4.1.16 | 99 | 32 | NT | | I.dentatus | | United States |

Fig. 12d

| STRAIN | CMAT | FAMILY | RFLP | SEROVAR | HUMAN | TICK | ANIMAL | COUNTRY |
|---|---|---|---|---|---|---|---|---|
| NBS16 | 2.1.10 | 99 | 33 | NR | Neuroborrelios | | | Sweden |
| 153 | 4.2.21 | 99 | 34 | 16 | | I.ricinus | | France |
| VS116 | NA | 99 | 35 | NT | | I.ricinus | | Switzerland |

Fig. 13

OSPC PROTEIN EPITOPE FREQUENCIES AMOUNG 77 STRAINS TESTED BY MEMBRANE ELISA USING THE BBM SERIES OF MONOCLONAL ANTIBODIES

| BBM-Number | Number of Reactions | Primary Epitope Sequence |
|---|---|---|
| BBM 22* | 14 | VKLS[ESVASL]SKAA |
| BBM 24* | 2 | |
| BBM 25 | 2 | |
| BBM 27 | 2 | |
| BBM 28 | 29 | TDNDS[KEAIL]KTNGT |
| BBM 29 | 41 | KELT[SPVVAET]PKKP |
| BBM 34 | 37 | F[VLAVKEVET]L |
| BBM 35* | 17 | YA[ISTLITEKLK]AL |
| BBM 36* | 12 | |
| BBM 37 | 47 | PNLTE[ISKKI]TDSNA |
| BBM 38 | 4 | TDNDSKEAIL |
| BBM 39* | 4 | TDNDS[KEAIL]KTNGT |
| BBM 40* | 23 | ASAN[SVKELT]SPVV |
| BBM 41* | 2 | |
| BBM 42 | 49 | S[PVVAETPKK]P |
| BBM 43* | 32 | SPVVAESPKK |
| BBM 44* | 9 | GK[KIQQNNGL]GA |
| BBM 45 | 66 | S[PVVAETPKK]P |
| BBM 46* | 1 | |
| BBM 47* | 21 | |
| BBM 48 | 6 | |
| BBM 49* | 9 | |
| BBM 75 | 3 | |
| BBM 76 | 3 | |
| BBM 77* | 3 | |

* denote monoclonal antibodies ultimately used in the serovar analysis

II. GROUPING OF REACTION FREQUENCIES

| BBM-Number | Reaction number low 0-10 | Reaction number medium 10-24 | Reaction number high >25 |
|---|---|---|---|
| Frequency | 13 | 5 | 7 |

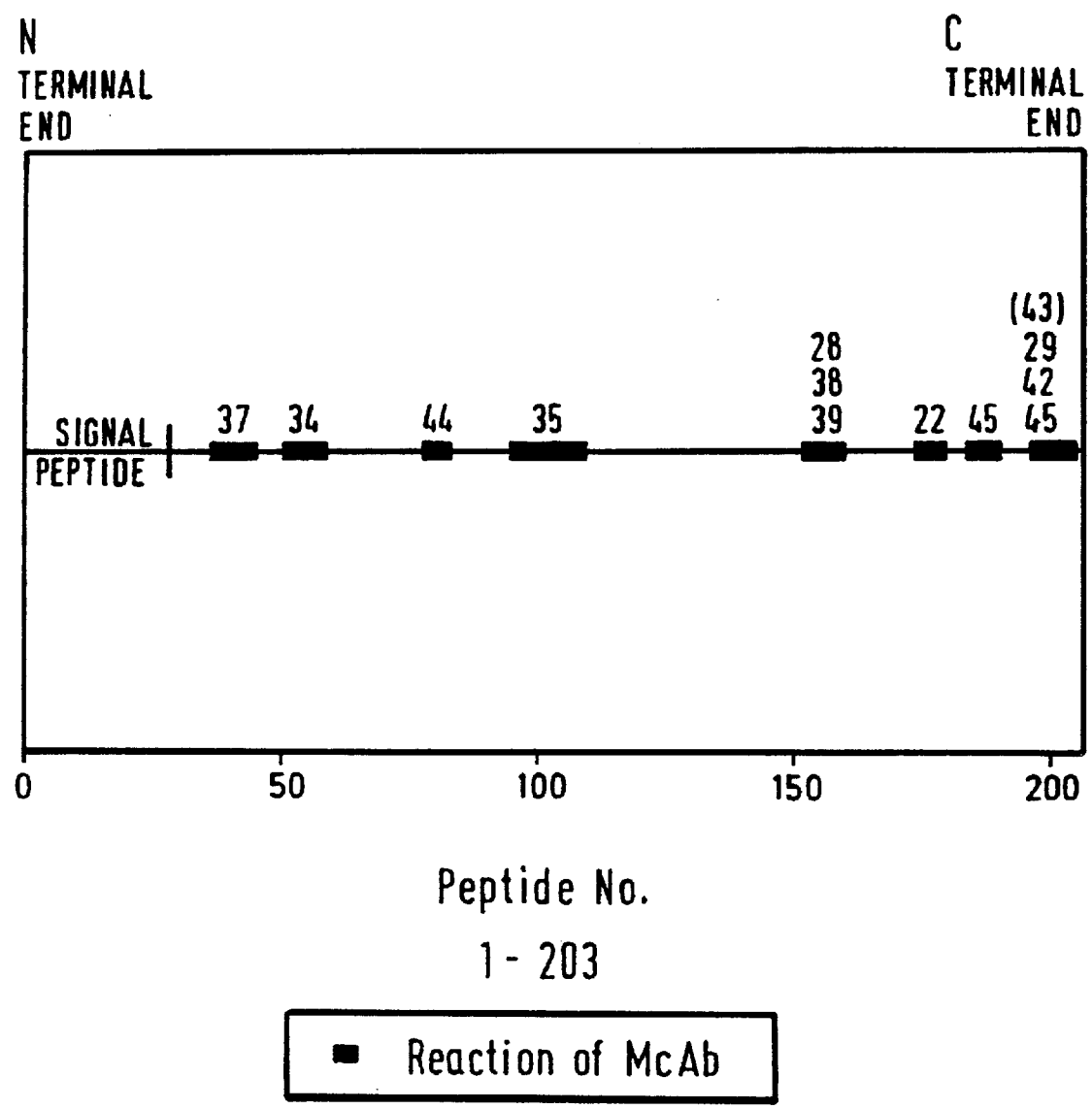

Fig. 15

Cross-Protection between OspC proteins from different OspC families

| Expt. | Test OspC antigen | | No. infected/tested | | |
|---|---|---|---|---|---|
| | OspC Family | Source | Immunized with test OspC | Immunized with Orth OspC$_a$ | Non-immunizied |
| A | 1 | ZH7 | 10/10 | 1/10 | 10/10 |
| B | 5 | H7 | 0/10 | 0/10 | 10/10 |
| C | 7 | PKO | 10/10 | 2/10 | 9/10 |
| D | 10 | W$^b$ | 9/10 | 5/10 | 10/10 |

$a$ OspC family 5.

$b$ With aluminium hydroxide as adjuvant and not titermax as in experiments A-C.

Fig. 16

SUMMARY OF TYPING DATA AND THE FREQUENCY OF THE SPECIFIC
ANTI OSP C ANTIBODIES IN THE HUMAN HUMORAL RESPONSE

| OspC Family | OspC Genotype | OspC Serovar | Number of Strains | Number of Human Isolate | Strain used in Frequency Study | % Frequency* |
|---|---|---|---|---|---|---|
| 1 | 1 | 1 | 5 | 1 | ZS7 | 6 |
| 2 | 2 | 2 | 9 | 5 | B31 (IP2) | 12 |
| 2 | 3 | 2 | 1 | - | | |
| 3 | 4 | - | 1 | 1 | 297 | 6 |
| 4 | 5 | 3 | 4 | 4 | H5 | 29 |
| 4 | 6 | 3 | 1 | - | | |
| 5 | 7 | 4 | 4 | 3 | ORTH | 35 |
| 6 | 8 | 5 | 4 | 3 | H14 | 12 |
| 6 | 8 | 6 | 1 | 1 | H15 | 29 |
| 6 | 8 | N.R. | 1 | 1 | | |
| 7 | 9 | 7 | 5 | 3 | JSB | 18 |
| 8 | 10 | 8 | 1 | 1 | E61 | 12 |
| 8 | 11 | 9 | 1 | 1 | | |
| 9 | 12 | 10 | 3 | 1 | M57 | 6 |
| 10 | 13 | 11 | 2 | 2 | W | 0 |
| 11 | 14 | 12 | 2 | - | KL10 | 0 |
| 11 | 15 | 13 | 3 | 1 | NSB1ab | 0 |
| 12 | 17 | N.R. | 2 | 1 | BITS | 0 |
| 13 | 18 | | 2 | 1 | KL11 | 6 |
| 13 | 19 | N.R. | 4 | 1 | | |
| 14 | 20 | 14 | 4 | 1 | 20047 | 12 |
| 15 | 21 | 15 | 2 | 2 | | |
| 16 | 22 | 16 | 4 | 3 | VS461 | 6 |
| 17 | 23 | N.R. | 1 | 1 | | |
| 18 | 24 | | 1 | - | H8 | 0 |
| 19 | 25 | N.R. | 2 | 2 | | |
| 20 | 26 | 16 | 1 | - | | |

* total number of positive ospC sera=17
N.R. non reactive

Plasmid pPC-PP4

Fig. 18

| Antigen | Adjuvant | challenge strain | challenge dose | infected / tested |
|---------|----------|------------------|----------------|-------------------|
| OspC | Titermax | Orth | $1 \times 10^4$ | 2/10 |
| OspC/ P. pastoris | Titermax | Orth | $1 \times 10^4$ | 0/10 |
| None | Titermax | Orth | $1 \times 10^4$ | 9/10 |

Fig. 19

Examples of OspC Vaccine Formulations Dsigned to Protect Against Specific Human Disease Associated Clones or Clonal Clusters of Lyme Disease Borrelia.

| Vaccine against the HDA clone (CMAT 4) of Borrelia burgdorferi sensu stricto | Vaccine against the HDA clone (CMAT 13) of Borrelia afzelii | Vaccine against the HDA clonal cluster (CMATs 17; 18; 20 & 22) of Borrelia garinii sp. nov. |
|---|---|---|
| Family 2 | Family 4 | Family 9 |
| Family 3 | Family 5 | Family 10 |
| Family 20 | Family 6 | Family 11 |
|  | Family 7 | Family 12 |
|  | Family 8 | Family 13 |
|  | Family 16 | Family 14 |
|  |  | Family 17 |
|  |  | Family 19 |

IMMUNOGENIC FORMULATION OF OSPC ANTIGEN VACCINES FOR THE PREVENTION AND TREATMENT OF LYME DISEASE AND RECOMBINANT METHODS FOR THE PREPARATION OF SUCH ANTIGENS

This application is a continuation-in-part of 08/053,863 filed Apr. 29, 1993 now abandoned, which is a continuation-in-part of 07/903,580 filed Jun. 25, 1992, which is a continuation-in-part of 07/824,161 filed Jan. 22, 1992 now abandoned, which is continuation-in-part of 07/727,245 filed Jul. 11, 1991 now abandoned.

The present invention relates to the prevention and treatment of Lyme disease in mammals and in particular to immunogenic formulations comprising different serological forms of OspC to retard or prevent the development of Lyme disease. The invention also comprises recombinant methods for the preparation of novel antigens.

BACKGROUND OF THE INVENTION

Lyme disease or Lyme borreliosis are terms used to describe the diverse clinical symptoms associated with tick-borne spirochetal infections caused by Lyme Disease Borrelia. Common manifestations of Lyme disease include disorders affecting the skin [erythema migrans (EM) or acrodermatitis chronica atrophicans (ACA)], nervous system (neuroborreliosis), and joints (arthritis) but other organs and tissues may become infected and diseased. Lyme disease has a world-wide distribution and is the most prevalent tick-borne disease in both the United States and Europe. The range of clinical symptoms commonly associated with Lyme disease in Europe is broader than that in the United States, with skin and nervous system disorders being common in Europe but rare in the United States, whereas arthritis is more common in the United States than in Europe. The clinical symptoms in North America appear to be a subset of those observed in Europe.

Lyme disease is typically treated with antibiotics. Treatment may be delayed, however, due to the often complex clinical picture and the lack of widely available, reliable diagnostic tests. If the disease is allowed to proceed to a chronic condition, treatment with antibiotics is more difficult and is not always successful. Furthermore the prospect that permanent damage is induced is likely to be increased during the course of a prolonged infection. Accordingly, a vaccine to prevent Lyme disease is desirable.

Two antigens from Lyme disease Borrelia have been described that can protect against infection/disease by this organism as determined in animal models of Lyme disease. These antigens, OspA and OspC (or "pC"), therefore are likely candidates for inclusion in any vaccine designed to protect against Lyme disease. See Simon et al., European patent No. 418,827; Fikrig et al., Science 250: 553–56 (1990); Preac-Mursic et al., Infection 20: 342–49 (1992). OspA and OspC share many characteristics. Both are lipoproteins that are exposed at the cell-surface, (Howe et al., Science 227: 645–46 (1985); Bergstrom et al. Mol. Microbiol. 3: 479–486 (1989)), both are plasmid-encoded (Barbour et al., Science 237: 409–11 (1987); Marconi et al., J. Bacteriol. 175: 926–32 (1993)), the genes for these proteins are present in most strains (Barbour et al., J. Infect. Dis. 152: 478–84 (1985); Marconi et al., J. Bacteriol. 175: 926–32 (1993)), and both exist in multiple serologically distinct forms (Wilske et al., (1989)).

The existence of multiple, serologically distinct forms of these antigens is an obstacle to the development of an OspA and/or OspC vaccine to protect against most, if not all, forms of Lyme disease. For instance, it has been demonstrated by Fikrig et al., J. Immun. 148: 2256–60 (1992), that immunization with one serological form of OspA, such as recombinant OspA of strain N40, need not protect against a challenge with a strain expressing a different OspA, for example, strain 25015. Consequently, it is necessary to develop typing schemes to classify and group the different variants of the antigen (i.e., OspA and/or OspC) such that the optimal mixture of serologically distinct forms of the antigen(s) that are needed to give broad protection can be determined.

A serotyping system for OspA has been developed using a limited number of monoclonal antibodies as the typing tools and 7 serotypes of OspA have been described using this methodology. Wilske et al., Ann. N.Y. Acad. sci. 539: 126–43 (1988). Restriction fragment length polymorphism (RFLP) analysis of OspA genes from 55 different European and North American strains identified six distinct genogroups. Wallich et al., Infection and Immunity 60: 4856–66 (1992). OspA proteins from North American isolates seem to be reasonably uniform since twelve of fourteen OspA's belonged to OspA type I and two to OspA type III. By contrast, the OspA's from European isolates are much more heterogeneous and include representatives of OspA types I (18), II (17), IV (4) and V (1). Construction of a phylogenetic tree based on sequence data for twelve OspA proteins from individual strains of B. burgdorferi supports the findings of the RFLP analysis but sequence information from isolates from two of the six genogroups is still lacking. At present no typing system exists for OspC.

Another consideration when selecting the appropriate antigens for inclusion in a vaccine is whether they are derived from strains that are epidemiologically important for the disease. In the mid-1970's it was postulated that pathogenic bacteria arise from a limited number of clones of highly related bacteria that in some way have a selective advantage in causing disease. This clonal hypothesis has since been confirmed. See Achtman et al., J. Infect. Dis. 165: 53–68 (1992). Thus, it is highly likely that among the numerous strains of Lyme disease Borrelia found in nature, only a limited number of "clones" exist that are highly adapted to causing mammalian, and in particular human, disease. In developing a vaccine to protect against disease in mammals and hence also in humans, it is of paramount importance to identify disease associated clones so that efforts can be concentrated against them. Thus it is necessary to elucidate the population structure of the species Lyme disease Borrelia and identify disease associated clones.

To date, a number of methods have been used to resolve the population structure of Lyme disease Borrelia, including (A) RFLP analysis of genomic DNA or of specific genes (LeFebvre et al., J. Clin. Micriobiol. 27: 636–39 (1989); Marconi & Garon, J. Bacteriol 174: 241–44 (1992); Postic et al., Res. Micriobiol. 141: 465–75 (1990); Stahlhammar-Carlemalm et al., Zbl. Bak 274: 28–39 (1990); Adam et al., Infect. Immun. 549: 2579–85 (1991); Wallich et al., Infect. Immun. 60: 4856–66 (1992)), (B) DNA-DNA hybridization (LeFebvre et al., J. Clin. Micriobiol. 27: 636–39 (1989); Postic et al., Res. Micriobiol. 141: 465–75 (1990)), (C) analysis of 16S rRNA by hybridization to oligcnucleotide probes (Marconi et al., J. Clin. Micriobiol 30: 628–32 (1992) or by sequencing (Adam et al., Infect. Immun. 59: 2579–85 (1991); Marconi & Garon, J. Bacteriol. 174: 241–44 (1992)), (D) fingerprinting by an arbitrarily primed polymerase chain reaction (Welsh et al., Int. J. System. Bacteriol. 42: 370–77 (1992)), (E) multi-locus enzyme electrophoresis (Boerlin et al., Infect. Immun. 60: 1677–83 (1992)) and (F) serotyping of isolates (Peter & Bretz, Zbl. Baktk. 277: 28–33 (1992)).

There is broad agreement between the results obtained by these different procedures. In general, it appears that Lyme disease Borrelia isolates can be divided into at least three major groups. Indeed, some investigators believe that the genetic distances between members of these groups is sufficient to merit differentiating them into three separate species: *B. burgdorferi* sensu stricto (type strain B31), *B. garinii* sp. nov. (type strain 20047) and a species designated *B. afzelii* or the "group VS461 Borrelia." See Baranton et al., Int. J. Syst. Bacteriol. 42: 378–383, 1992; Marconi & Garon, supra.

The significance of the existence of these different groups for vaccine development remains to be fully elucidated. It is clear from the data of Wallich et al., Infection & Immunity 60: 4856–66 (1992), that there is a strong association between the genogroup to which an isolate belongs and the type of OspA that is produced: isolates from the group containing strain B31 (genogroup AAA or *B. burgdorferi* sensu stricto) produce a type I OspA (all of thirty strains analyzed), isolates from the group containing strain 20047 (genogroup BBB or *B. garinii* sp. nov.) usually produce a type II (17/19) OspA but types V (1/19) and VI (3/39) were also noted, isolates from the clone containing strain B023 (genogroup BBA or group VS 461) produce a type IV OspA (4/4), the remaining two isolates (genogroup B, B/A, A) produce a type III OspA.

Lyme disease isolates from North America predominantly belong to one group (genogroup AAA or *B. burgdorferi* sensu stricto), represented by strain B31, and consequently produce a type I OspA. This suggests that a vaccine containing a type I OspA may be sufficient to protect against most isolates causing Lyme disease in North America at the present time. In Europe the picture is more complex, since all three major clones are found and there is correspondingly an increased diversity in the types of OspA present (genotypes I, II, IV, V, VI). Furthermore, OspA was found not to protect in two studies, conducted using Lyme disease isolates from Europe, which also demonstrated the utility of OspC as a protective antigen. See U.S. patent application No. 07/903,580; Preac-Mursic et al., Infection 20: 342–49 (1992).

It was not known heretofore whether OspC was clonally inherited, with specific types of OspC restricted to particular groups of Lyme disease isolates (that is, to *B. burgdorferi* sensu stricto, *B. garinii* sp. nov. or group VS461). As OspC is plasmid encoded, Marconi et al., J. Bacteriol. 175: 926–32 (1993), it was conceivable that there had been plasmid-mediated transfer of the OspC gene between the different species of Lyme disease isolates. If this were the case, then the different types of OspC which are known to exist but which have not been defined, would not necessarily be clonally inherited.

SUMMARY OF THE INVENTION

It is the object of the present invention to provide an effective OspC vaccine, with broad cross protective levels in relation to all strains, against Lyme disease in mammals, by selecting OspC formulations based on defined OspC families resolved by phenotypic typing (the OspC "serovar" typing) and RFLP typing analyses, and sequence analysis of a large variety of strains of worldwide origin.

Furthermore, the OspC gene has been discovered to be clonally inherited. Consequently, it now is possible to interpret the results of the OspC typing schemes in view of epidemiological information from a "Common Membrane Antigen Typing" (CMAT) scheme, described below, which can be used to elucidate the clonal population structure of Lyme disease Borrelia strains. By the same token, it also now is possible to select the most appropriate OspC vaccine formulations either (a) to enable one to design vaccines to protect against strains prevalent within defined geographical regions or (b) to protect specifically and preferentially against epidemiological important disease associated clones or clonal clusters of *B. burgdorferi.*

In accomplishing these and other objectives, there has been provided, in accordance with one aspect of the present invention, an immunogenic composition comprising (a) an amount of material comprising (i) one or more OspC antigens of Lyme disease Borrelia substantially purified from each of the 20 currently recognized OspC families of FIG. 11 or (ii) OspC variants or OspC mimetics of said OspC antigens, said OspC variants or OspC mimetics having a structure that is sufficiently similar to native OspC to induce the production of protective antibodies; and (b) a physiologically-acceptable excipient therefore, wherein said amount is sufficient to elicit, in a mammal susceptible to Lyme borreliosis, an immune response that is protective against Lyme borreliosis.

According to a further embodiment, the above immunogenic composition comprises one or more, preferably two or more, OspC antigens of Lyme disease Borrelia of the 20 currently recognized OspC-families of FIG. 11 or OspC variants or OspC mimetics of said antigens as defined above under (ii), and a physiologically-acceptable excipient as defined above under (b).

In accordance with another aspect of the present invention, an immunogenic composition is provided that comprises an amount of material comprising (i) one or more OspC antigens of Lyme disease Borrelia substantially purified from each of the OspC-families of FIG. 19 expressed by the human disease associated (HDA) clones and clonal clusters or (ii) OspC variants or OspC mimetics of the OspC antigens, said OspC variants or OspC mimetics having a structure that is sufficiently similar to native OspC to induce the production of protective antibodies; and (b) a physiologically-acceptable excipient therefore, wherein said amount is sufficient to elicit, in a mammal susceptible to Lyme borreliosis, an immune response that is protective against Lyme borreliosis.

As a preferred embodiment, the above immunogenic composition comprises one or more, preferably two or more, OspC antigens of the OspC-families of FIG. 19, or OspC variants or OspC mimetics as defined above under (ii), and a physiologically-acceptable excipient as defined above under (b).

In a preferred embodiment, an immunogenic composition within the present invention is designed to protect against Lyme disease Borrelia strains prevalent within a particular geographic region, such as North America, Europe or Austria.

As a preferred embodiment a combined OspA/OspC vaccine, which is superior to a vaccine formulated with either antigen alone is claimed:

The invention also comprises recombinant methods for the production of novel OspC antigens together with DNA sequences, expression vectors, and transformed host cells.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 describes 77 Borrelia strains which were used in the experimental investigations. The country of origin and the biological source (i.e. human, tick or animal) from which these strains were isolated is described. The clinical material and disease syndrome from which the human isolates were obtained is shown too (Abbreviations: CSF, cerebrospinal fluid; ACA, acrodermatitis chronica atrophicans; EM, erythema migrans). The properties of 5 additional strains not experimentally studied are also included, since published information pertaining to these strains was used in some of the analyses.

FIG. 2 lists the addresses of all strain contributors.

FIG. 3 lists the monoclonal antibodies and their common membrane antigen specificities. The homologous reacting strain and the isotype of the monoclonal antibody are also indicated.

FIG. 4 shows the individual scores and representative strains for each of the CMATs resolved by the CMAT typing scheme.

FIG. 6 gives the reaction pattern of a panel of 16 OspC-specific monoclonal antibodies with the various serovar type strains.

FIG. 7 shows the sizes of the restriction fragments obtained when PCR amplified OspC genes (prepared as described in example 4 are digested with the enzymes Dpn11, Dde1 and Dra1. The data presented shows the 35 unique patterns of restriction fragments (i.e. 35 ospC RFLP types) identified from an analysis of the restriction fragment data from the 82 strains listed in Type strains chosen to represent each of the OspC RFLP types are also given.

FIGS. 8A–8D show the FIG. 1 aligned, partial nucleotide sequences of twenty-four OspC genes selected from strains belonging to OspC RFLP types 1–24. (SEQ ID NOS 3, 53, 7, 9, 11, 13, 15, 17, 19, 21, 23, 25, 27, 29, 31, 33, 35, 37, 39, 41, 43, 45, 47, and 49 are partially shown in this Figure.)

FIGS. 8E–8H show the complete sequences of the novel OspC genes according to FIG. 8 including the 3' end. Additionally FIGS. 8E–8H include the sequences for the OspC genes of strains H13 and 28691. (SEQ ID NOS 1, 3, 5, 7, 9, 11, 13, 15, 17, 19, 21, 23, 25, 27, 29, 31, 33, 35, 37, 39, 41, 43, 45, 47, 49 and 51 are shown in this Figure.) FIG. 9A shows the aligned, partial amino acid sequences deduced from the nucleotide sequence data of FIGS. 8A–8D. The sequenced region corresponds to the first 92% of the mature OspC protein. (SEQ ID NOS 4, 54, 8, 10, 12, 14, 16, 18, 20, 22, 24, 26, 28, 30, 32, 34, 36, 38, 40, 42, 44, 46, 48 and 50 are partially shown in this Figure.)

FIG. 9B shows the complete amino acid sequences of the novel OspC antigens according to FIG. 9A including the C-terminal. Additionally FIG. 9B includes the sequences for the OspC antigens of strains H13 and 2869. (SEQ ID NOS 2, 4, 6, 8, 10, 12, 14, 16, 18, 20, 22, 24, 26, 28, 30, 32, 34, 36, 38, 40, 42, 44, 46, 48, 50 and 52 are shown in this Figure.)

FIG. 10 is a dendrogram of the OspC protein sequence data of Figure 9B showing the phylogenetic relationships between the sequences and the degree of sequence identity. This analysis has been used to assign the OspC proteins into OspC families. Members of an OspC family comprise related OspC sequences with >80% sequence identity. It is also shown that OspC proteins cluster in a species-specific manner indicating that the OspC protein is clonally inherited.

FIG. 11 lists the 20 OspC families and indicates strains chosen as a representative of that family.

FIG. 12 summarizes the results of the CMAT and OspC typing analyses of the 82 strains from FIG. 1. The data are sorted by OspC family and RFLP-type to show the frequency with which strains belonging, to a particular OspC family occur. Strains which have not been assigned an OspC family are designated 99. The biological and geographical origins of the strains is included to allow a comparison of these parameters with the OspC family. CMAT values have been assigned to 5 strains for which there was a published description but which were not tested (i.e. strains of B. burgdorferi, B. afzelii and B. garinii correspond to CMATs 1,3 and 4 respectively). OspC serovars have not been assigned to all strains; 5 strains were not available (NA), others were not tested (NT) since they expressed insufficient amounts of OspC for reliable typing and some were tested but were non-reactive (NR) with the panel of monoclonal antibodies.

FIG. 13 lists the sequences (SEQ ID NOS 67–76) of the mapped OspC epitopes together with the frequency of their occurrence among the strains analyzed. At the bottom of the table the monoclonals are grouped into categories according to the frequency with which they react with the seventy seven strains in the study.

FIG. 14 shows the map of the generalized OspC protein marking the location of the epitopes of numerous BPM monoclonal antibodies indicated by their numbers.

FIG. 15 shows the results of active immunization experiments using the gerbil model. Groups of animals were immunized with purified OspC protein variants of either the same (H7) or different OspC family (ZS7, PKO and W) to that of the challenge strain Orth. The results indicate that there is strong cross protection when one immunizes with a variant of the same family as that expressed by the challenge strain, but that there is little or no protection when one immunized with an OspC variant of a different OspC family to that of the challenge strain.

FIG. 16 summarizes the OspC typing information and the distribution of human isolates among the various OspC types. The specificity and prevalence of OspC antibodies present in human Lyme disease sera form the Czech Republic is also shown. OspC antibody specificity was defined by testing against a panel of 18 different Borrelia strains representing 16 OspC families.

FIG. 18 shows the results of active immunization experiments using the gerbil model. Animals were immunized with purified OspC protein derived from B. burgdorferi strain Orth and recombinantly produced from P. pastoris GS115/pPC-PP-4. The results indicate a strong protection with the Borrelia derived as well as with the Yeast-derived OspC protein.

FIG. 19 shows examples of OspC vaccine formulations designed to protect against specific human disease associated clones or clonal clusters of Lyme disease Borrelia.

DETAILED DESCRIPTION OF THE INVENTION

By the serovar, restriction fragment length polymorphism (RFLP) and sequencing analyses described in greater detail below, it has been discovered that, despite the high degree of OspC protein heterogeneity across different Lyme disease isolates, OspC proteins can be grouped into a limited number of families on the basis of similarity in amino acid sequence, inter alia. In accordance with the present invention, the implications of this finding are realized in the design of vaccine formulations that provide a high level of cross-protectivity, relative to different strains, which has not been attained previously.

In order to achieve such cross-protection one must be able to predict the effectiveness of the components of a given vaccine in protecting against all possible disease-causing strains. Pursuant to the present invention, this problem is overcome by insuring that the heterogeneity of protective antigen components in a vaccine optimally reflects the heterogeneity found in nature. In particular, for the OspC protein this is achieved by formulating vaccines that contain representatives for all of the OspC families revealed by the sequence analysis described here. An example of such a formulation entails including in a vaccine the twenty OspC proteins that are representative of all of the aforementioned OspC families. An OspC family is defined as a group of OspC proteins that have more than 80% amino acid sequence identity over the first 92% of the mature OspC protein i.e. excluding the information for the 18aa leader sequence and the final 16aa as shown in FIGS. 9A, 9B and 10.

The present invention thus relates in one aspect to an immunogenic composition comprising one or more OspC antigens substantially purified from each of the twenty OspC families which the present inventors have delineated for the first time. The use of twenty antigens, for example, is an improvement over the prospect of including all possible OspC variants found in nature (cf. 35 OspC RFLP types described here). In accordance with another aspect of the present invention, the formulation of a Lyme disease vaccine is simplified further by restricting the number of antigenic components, in a manner that does not reduce the protective efficacy of the vaccine, by the combined application of OspC typing data and epidemiological data. Exemplary of this approach, as described in greater detail below, are (A) the design of vaccine formulations for use in a particular geographic region, such as North America, Europe or a particular country such as Austria, and (B) the design of a vaccine that is targeted to protect specifically against only those clones, identified by CMAT analysis, which are associated with human disease. In one embodiment under rubric (A), a vaccine is formulated for use in North America and contains antigens representing only those OspC families observed for American strains, namely, families 2 and 3 (see FIG. 12).

According to another embodiment said vaccine formulated for use in North America comprises strains from families 2, 3, 18 and 20.

In order to identify clones of Lyme disease Borrelia, a population structure analysis was carried out by CMAT analysis. A "CMAT (type)" is defined as a unique, nine-digit score resulting from the combined score of molecular weight variants of nine common membrane antigens detected, and in some cases differentially discerned, by a given set of monoclonal antibodies specific for these antigens. A "CMAT cluster" is a group of related CMAT (types) having at least 50% similarity in their CMAT score. A "CMAT group" is used here to denote a group of CMAT types having more than or equal to 20% similarity in their CMAT score. Consequently, a CMAT group may be comprised of several CMAT clusters which in turn may be comprised of several CMAT types.

A "clone" is defined as a CMAT type comprising more than one strain, or otherwise, a clone is a group of strains having the same CMAT type and thus are considered as arising from a common ancestral strain. A "clonal cluster" is a group of clones related at the CMAT cluster level (that is, where their CMAT types are more than 50% similar). A "human disease-associated clone" is a clone that, based on epidemiological and clinical data, can be shown to be associated frequently with human disease. Likewise, a "human disease-associated clonal cluster" is a clonal cluster that can be shown, from epidemiological and clinical data, to be associated frequently with human disease. Thus in an embodiment under rubric B (see above), an OspC vaccine is formulated against the human disease associated CMAT clones 1.2.4., 3.2.13, and the clonal cluster 4.2.17, 4.2.18, 4.2.20 and 4.2.22.

OspC is known to be a suitable immunogen for eliciting a protective immune response in animal models of Lyme disease when the challenge organism is the same Lyme disease isolate from which the OspC was derived. Due to the serological heterogeneity of OspC proteins among Lyme disease Borrelia strains, however, it was thought that immunization with OspC from one strain might not protect against infection with a wide range of Lyme disease Borrelia isolates and recognized a need to validate this assumption based upon cross-protection studies (Example 6). Based upon these studies, it became clear that an OspC based vaccine would have to contain several serologically distinct forms of OspC. A prerequisite to the formulation of such a multivalent OspC vaccine is knowledge of the degree of diversity among the different forms of OspC and of how these different forms are related. Accordingly, such information is applied, pursuant to the present invention, in the development of new vaccine formulations against Lyme disease Borrelia.

The first step towards acquiring the required information was the development of a monoclonal antibody based typing system (Example 1) for characterizing the OspC proteins from different Lyme disease Borrelia strains. In order to ensure that the widest range of OspC proteins would be analyzed a large number of Lyme disease Borrelia strains (i.e. 62 of the 82 strains depicted in FIG. 1 were selected as producing sufficient OspC to allow a reliable characterization) from different geographical locations and isolated from humans (for example, skin, cerebrospinal fluid and blood), animal and ticks were studied. Another key aspect of this analysis was the use of a large number of OspC-specific monoclonal antibodies (25 in the present example) that had been produced not simply to one OspC protein but to six different OspC proteins, thereby increasing the diversity of OspC epitopes capable of being recognized and hence increasing the power to discriminate between different OspC proteins. The data collected in this analysis clearly showed that a large degree of serological heterogeneity exists among the OspC proteins from different sources. Examples of the reaction patterns of the 16 distinct types, or serovars, of OspC that were identified with a collection of 13 monoclonal antibodies are shown in FIG. 6. In addition, 12 strains were non-typable as they did not react with any of the monoclonal antibodies.

Figure 5:
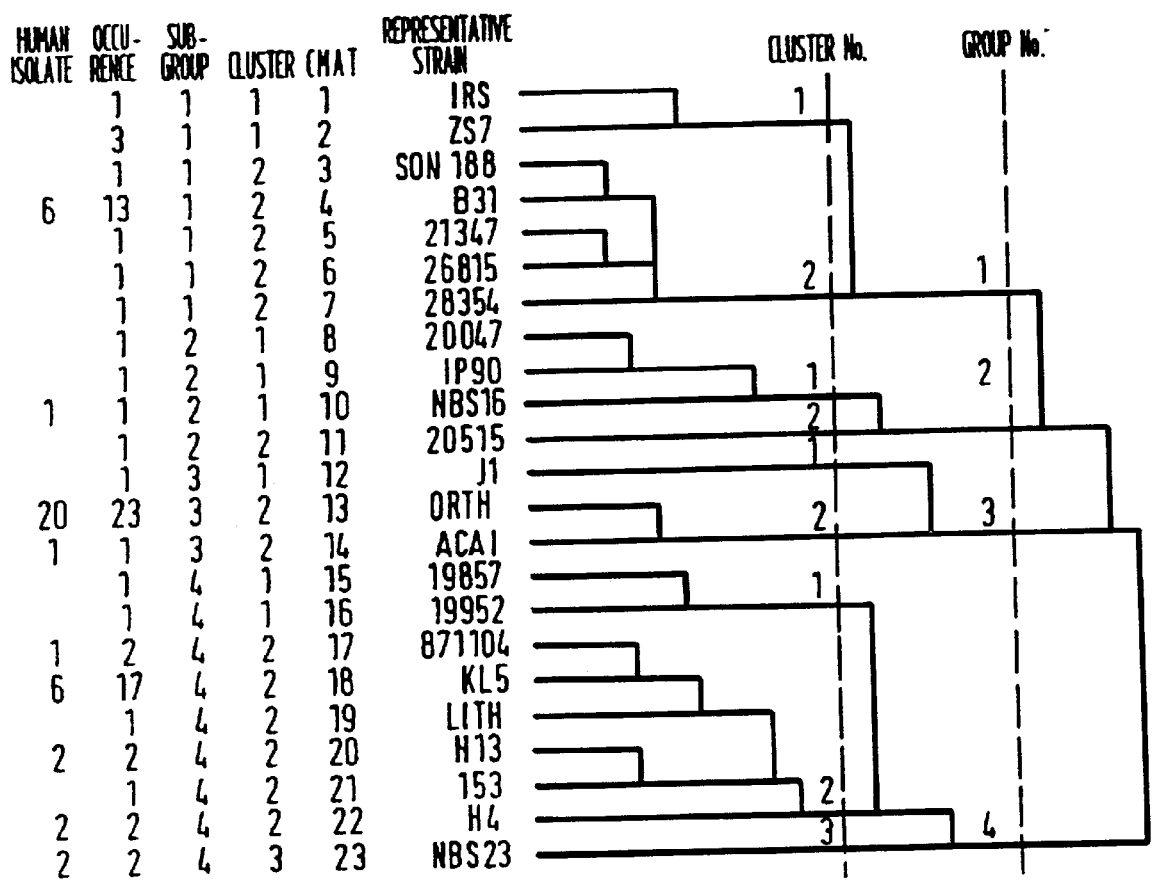
FIG. 5 shows the dendrogram of the cluster analysis performed on the CMAT typing data. The frequency of occurrence of the CMATs among the strains tested also is indicated, as are the grouping of the individual CMATs into CMAT clusters (all CMATs with >50% similarity) and CMAT subgroups (all CMATs with >20% similarity).
Figure 17:
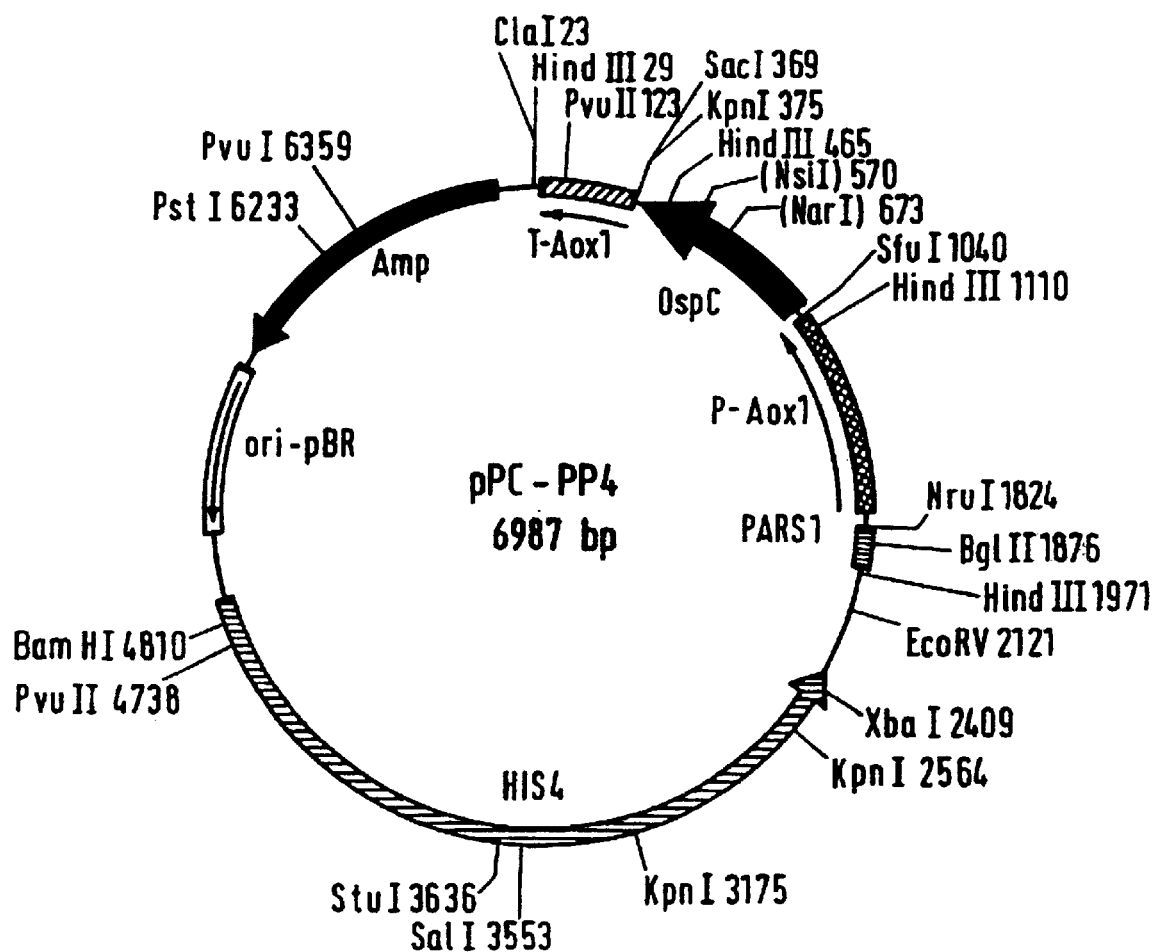
FIG. 17 shows the yeast expression vector pPC-PP4 with the OspC coding sequence under transcriptional control of the methanol inducible AOX-1 promotor.

Although highly effective, the typing of OspC by serological means was nevertheless incomplete, since it requires both that OspC is expressed as a major protein and that a set of antibodies with a wide range of specificities is available. It was clear from the results of the serovar analysis that the full-spectrum of antigenic diversity was not being detected with the monoclonal antibodies being used, even although they had been chosen to minimize this problem. Consequently, the heterogeneity of OspC was further studied by analysing the restriction fragment length polymorphism (RFLP) occurring within the ospC gene (Example 3). An analysis of the data from 82 strains (i.e. experimental data from all 77 strains in our culture collection plus information deduced from 5 published ospC sequences; see FIG. 1) revealed the presence of 35 distinct RFLP ospC types. Although this method detects more variation than evident from the serovar typing, there is extremely good agreement between the results obtained with the two methods (FIG. 12).

The classification of Borrelia strains into serovars and RFLP-types according to the OspC protein or gene that they possess, made it possible, pursuant to the present invention, to select for more detailed characterization a limited number of OspC variants which are representative of the population as a whole. Thus, a panel of 29 strains comprising one or more representatives from each of the most ubiquitous OspC types was selected, the OspC gene was amplified by PCR, and the nucleotide and deduced amino acid sequence determined (see Example 4). The amino acid sequence of the mature OspC protein (from cysteine 19; see U.S. patent application Ser. No. 07/903,580, previously incorporated by reference), less the last 16 amino acids, was used to determine the relationship between OspC proteins from the different OspC serovars/RFLP-types.

The relationship between closely related OspC proteins from the same OspC type was investigated as a further check on the validity of the typing systems and to establish whether within a given OspC type there was further heterogeneity. The nucleotide and deduced amino acid sequences for the OspC proteins from 24 strains are shown in FIGS. 8A–9B, respectively (i.e. 22 sequences from this study and 2 published sequences for strains 2591 and PBI). The dendrogram showing the phylogenetic relationship between the OspC protein is presented in FIG. 10.

An OspC antigen-based immunogen of the present invention can comprise a mixture of different serological forms of naturally occurring OspC protein. In another embodiment of the invention, the immunogenic composition comprises OspC variants or OspC mimetics of OspC antigens. Thus, in addition to OspC protein obtained from Lyme disease Borrelia cells, as described hereinafter, recombinant OspC variants of the naturally-occurring molecule ("OspC variants") and "mimetics"—compounds having mimotopes which mimic OspC epitopes—can be employed.

The category of OspC variants includes, for example, oligopeptides and polypeptides corresponding to immunogenic portions of the OspC molecule and any non-proteinaceous immunogenic portions of the OspC molecule. Thus, a variant is intended to include a polypeptide that is homologous to and retains the salient immunological features of the natural OspC molecule. In this regard, "homology" between two sequences connotes a likeness short of identity indicative of a derivation of the first sequence from the second. For example, a polypeptide is "homologous" to OspC if it contains an amino acid sequence which corresponds to an epitope recognized by OspC specific antibodies or T-cells. Such a sequence may be only a few amino acids long and may be a linear determinant or one which arises when amino acids from separated portions of a linear sequence are spatially juxtaposed after protein folding or after being subjected to covalent bond modification. The amino acid sequences which are antigenic determinants for purposes of this invention can be ascertained, for example, by monoclonal mapping analysis techniques which are known in the art. See Regenmortel, Immunology Today 10: 266–72 (1989), and Berzofsky et al., Immunological Reviews 98: 9–52 (1987). For instance, in the present invention, the OspC antigen comprises one or more of the following amino acid sequence (SEQ ID NOS 67–76)(FIG. 13):

(1) VKLSESVASLSKAA;
(2) TDNDSKEAILKTNGT;
(3) KELTSPVVAETPKKP;
(4) FVLAVKEVETL;
(5) YAISTLITEKLKAL;
(6) PNLTEISKKITDSNA;
(7) ASANSVKELTSPVV;
(8) SPVVAETPKKP;
(9) GKKIQQNNGLGA; and
(10) SPWAESPKK or variants or mimetics of the above epitope sequences. In the preferred embodiment, the vaccine would comprise peptides corresponding to serotype-specific epitopes selected from one or more of the OspC proteins from the OspC families described herein. Cross-protection studies (Example 6) indicate that protective immunity is induced by serotype-specific epitopes. An example of a serotype-specific epitope is sequence #2 from strain Orth (see above), which is recognized by monoclonal antibodies BBM38 and BBM39 which are specific for OspC proteins from OspC family 5 (serovar 4). This epitope corresponds to the putative epitope (DNDSKE) predicted from a hydrophilicity analysis of the Orth OspC. Potential serotype-specific epitopes can likewise be predicted to occur between amino acid residues 120–155 (starting from the first cysteine residue) in OspC proteins from other OspC families (example 4). Such a vaccine may include variants or mimetics of the peptide sequences, as described below. Assaying for this type of similarity can also be effected via a competitive-inhibition study in the case of antibodies or by T-cell proliferation.

Polypeptides which qualify as OspC variants according to these criteria can be produced, pursuant to the present invention, by conventional reverse genetic techniques, i.e., by designing a genetic sequence based upon an amino acid sequence or by conventional genetic splicing techniques. For example, OspC variants can be produced by techniques which involve site-directed mutagenesis or oligonucleotide-directed mutagenesis. See, for example, "Mutagenesis of Cloned DNA," in CURRENT PROTOCOLS IN MOLECULAR BIOLOGY 8.0. 3 et seq. (Ausubel et al. eds. 1989) ("Ausubel").

Other OspC variants within the present invention are molecules that correspond to a portion of OspC, or that comprise a portion of OspC but are not coincident with the natural molecule, and that display the immunogenic activity of OspC when presented alone or, alternatively, when linked to a carrier. An OspC variant of this sort could represent an actual fragment of the natural molecule or could be a polypeptide synthesized de novo or recombinantly.

To be used in recombinant expression of OspC or an OspC variant, a polynucleotide molecule encoding such a molecule would preferably comprise a nucleotide sequence, corresponding to the desired amino acid sequence, that is optimized for the host of choice in terms of codon usage, initiation of translation, and expression of commercially useful amounts of OspC or a desired OspC variant. Also, the vector selected for transforming the chosen host organism with such a polynucleotide molecule should allow for efficient maintenance and transcription of the sequence encoding the polypeptide. The encoding poly-ucleotide molecule may code for a chimeric protein; that is, it can have a nucleotide sequence encoding an immunological portion of the OspC molecule operably linked to a coding sequence for a non-OspC moiety, such as a signal peptide for the host cell.

In order to isolate a DNA segment which encodes an OspC molecule, total Lyme disease Borrelia DNA can be prepared, according to published methods. See, for example, Maniatis, et al., MOLECULAR CLONING: A LABORATORY MANUAL (Cold Spring Harbor Laboratories, NY 1982); Baess, Acta Pathol. Microbiol. Scand. (Sect. B) 82: 780–84 (1974). The DNA thus obtained can be partially digested with a restriction enzyme to provide a more or less random assortment of genomic fragments; an enzyme with a tetranucleotide recognition site, such as Sau3A (MboI), is suitable for this purpose. The fragments from such a partial digestion then can be size-fractionated, for example, by sucrose gradient centrifugation (see Maniatis, supra) or by pulsed field gel electrophoresis, see Anal, Trends in Genetics (November 1986), at pages 278–83, to provide fragments of a length commensurate with that of DNA encoding the OspC molecule.

According to well-known methods described, for example, in Ausubel at 5.0.1 et seq., the selected fragments can be cloned into a suitable cloning vector. A DNA thus obtained could be inserted, for example, at the BamHI site of the pUC18 cloning vector. Chimeric plasmids or phage, inter alia, produced by joining the size-selected fragments to the cloning vector can then be transformed into *E. coli* or other host cells, which are screened thereafter for expression of the encoded protein. A variety of methods can be used for screening libraries to identify a clone containing the OspC gene. These methods include screening with a hybridization probe specific for OspC, such as an oligonucleotide probe, or screening for OspC antigen expression using a OspC specific immunological reagent. The latter, for instance, may be accomplished by immunoblotting a library with anti-OspC monoclonal antibodies or with a specific polyclonal antibody prepared from animals immunized with purified OspC. Once a clone containing OspC encoding DNA is identified in the library, the DNA can be isolated, the region encoding OspC protein fully characterized (as by sequencing), and, subsequently, the DNA can be used to produce ospC expression vectors suitable to the production of OspC-active protein.

As noted previously, to provide an effective immunogen the structure of the recombinantly expressed pC protein should be sufficiently similar to that of native (non-denatured) OspC so that the protein induces the production of protective antibodies. To this end, it is preferable to express OspC-encoding DNA in such a way that intracellular proteolysis and aggregation of the expression product, in denatured form, are avoided. One way to avoid these problems is to recombinantly produce pC in a host-vector system that provides for secretion of pC from the host cell, preferably directly into the culture medium. One such system is provided by Bacillus subtilis. A suitable secretion vector can be constructed for *B. subtilis* by linking the *B. amyloliguefaciens* α-amylase signal sequence, see Young, et al., Nucleic Acid Res. 11: 237–49 (1983), to the Bacillus plasmid vector pUB110, as described by Ulmanen, et al., J. Bacteriol. 162: 176–82 (1985). According to this approach, the coding sequence for the foreign protein is cloned downstream of the promoter, the ribosome binding site and the signal sequence for α-amylase. Transcription and translation of OspC is under control of the α-amylase promoter and translation machinery in this construct, and secretion of pC from the host cell is provided by the α-amylase signal sequence. The present invention comprises expression vectors which are functional in procaryotes as well as eucaryotes. Similar vectors for use in yeast have been described and the expression secretion of OspC in yeast using these vectors could be achieved. A suitable expression vector can be constructed by linking the OspC coding sequence to an inducible promotor in a yeast replication plasmid. According to this approach, the coding sequence of the foreign protein is cloned downstream of e.g. the AOX-1 promotor and transcription and translation can be induced by the addition of methanol to the culture medium. Either intracellular expression or secretion of the foreign protein (by linking a signal sequence to the coding sequence of the mature protein) can be obtained. A preferred yeast strain is *Pichia pastoris*. In yeast, especially *P. pastoris*, high yields of the expression products were obtained.

Yet another approach for expressing OspC in a host vector-system which avoids proteolysis, aggregation and denaturation is the use of vaccinia virus as a vector capable of expression in a variety of mammalian host cells susceptible to vaccinia infection. This approach would entail preparing a recombinant vaccinia virus-derived vector in which the pC gene is placed under the control of a promoter, along with translation and secretion signals, suitable for expressing OspC protein in a vaccinia-infected host. As described in U.S. Pat. No. 4,603,112, the contents of which are hereby incorporated by reference, the plasmid also would comprise, 5' to the transcription control regions and 3' to the 3' termination and polyadenylation signals, flanking sequences which are conducive to homologous recombination into a wild-type vaccinia genome. When a construct of this sort is introduced into a vaccinia infected host cell, the flanking sequences direct recombination between the plasmid vector and the vaccinia virus, with the result that a cloned structural sequence (here, encoding OspC) becomes part of, propagates with and is expressed with the vaccinia virus. Preferably, the region between the flanking sequences also contains a selectable marker, such that in the presence of selection medium only those cells containing recombined vaccinia virus (and, in the present context, the sequence encoding a OspC-active polypeptide), will survive.

A recombinant vaccinia strain produced in this manner can be used to infect mammalian cells, such as Vero cells or CVl cells, suitable for high density fermentative growth. The OspC-active protein expressed in these cells during fermentation would be secreted into the fermentation medium, from which it would be purified via conventional methodology.

In addition to natural OspC and OspC variants, the present invention comprehends compounds ("mimetics") which mimic OspC epitopes ("mimotopes"). One example of a mimetic is an anti-idiotype antibody, that is, an antibody that is produced by immunizing an animal with an antibody which specifically binds to an epitope on an antigen. The anti-idiotype antibody recognizes and conforms to the combining site on the first antibody. Therefore, the shape of its combining site closely resembles the epitope which fits into the combining site of the first antibody. Because an antiidiotype antibody has a combining site whose shape mimics the original antigen, it can be used as a vaccine to generate antibodies which react with the original antigen. See Fineberg & Ertl, CRC Critical Reviews in Immunology 7: 269–84 (1987). Appropriate mimetics could be identified by screening with a OspC antibody to detect which compounds bind thereto or could be produced by molecular modelling. See Morgan et al., "Approaches to the Discovery of Non-Peptide Ligands for Peptide Receptors and Peptidases," in ANNUAL REPORTS IN MEDICINAL CHEMISTRY (Academic Press 1989), at pages 243 et seq.

The vaccine of the present invention is intended for the immunization of a susceptible mammal, including a human being, against Lyme disease. The term "immunogen" means an antigen which evokes a specific immune response leading to humoral or cell-mediated immunity, in this context, to infection with Borrelia. "Immunity" thus denotes the ability of the individual to resist or overcome infection more easily when compared to individuals not immunized, or to tolerate the infection without being clinically affected.

The immunogen of the present invention may be further comprised of an acceptable physiological carrier. Such carriers are well-known in the art and include macromolecular carriers. Examples of suitable carriers in mammals include tuberculin PPD, bovine serum albumin, ovalbumin or keyhole limpet hemocyanin. The carrier should preferably be non-toxic and non-allergenic.

The immunogen may be further comprised of an adjuvant such as an aluminum compound, water and vegetable or mineral oil emulsions (for example, Freund's adjuvant), liposomes, ISCOM (immunostimulating complex), water-soluble glasses, polyanions (such as poly A:U, dextran sulphate or lentinan), non-toxic lipopolysaccharide analogues, muramyl dipeptide, and immunomodulating substances (for example, interleukins 1 and 2) or combinations thereof. The preferred adjuvant is aluminum hydroxide. Immunogenicity can also be enhanced in mammals which have received live attenuated bacterial vectors, such as Salmonella or Mycobacteria, or viral vectors like vaccinia, which express an OspC-active polypeptide.

Techniques for formulating such immunogens are well-known in the art. For instance, the immunogen of the present invention may be lyophilized for subsequent rehydration in a physiologically acceptable excipient such as saline or other physiological solution. In any event, the vaccine of the present invention is prepared by mixing an immunologically effective amount of OspC with the excipient in an amount resulting in the desired concentration of the immunogenically effective component of the vaccine. The amount of immunogenically effective component in the vaccine will depend on the mammal to be immunized, with consideration given to the age and weight of the subject as well as the immunogenicity of the immunogenic component present in the vaccine. In most cases, an amount of the immunogenic component of the vaccine will be in the range of 1 to 100 micrograms per antigen per dose, and preferably will be in the range of 10 to 50 micrograms per antigen per dose.

In yet another embodiment of the present invention, the immunogenic composition is comprised of one or more OspC antigens or OspC variants or OspC mimetics or the OspC antigens substantially purified from each of the OspC-families of FIG. 11 expressed by the human disease associated clones and clonal clusters, as described in Example 1.

Thus, the invention comprises according to claims 1–3 immunogenic compositions of OspC antigens of Lyme disease Borrelia consisting either or one or more, preferably two or more, OspC antigens of the 20 currently recognized OspC-families as shown in FIG. 11 or of one or more OspC antigens from each of the 20 currently recognized OspC-families of FIG. 11. Instead of the above OspC antigens, the combination may comprise OspC variants or OspC mimetics of said OspC antigens, said OspC variants or OspC mimetics having a structure that is sufficiently similar to native OspC to induce the protection of protective antibodies.

Figure 13 shows the sequences of essential epitopes. According to the invention, OspC antigens are included which comprise one or more of such epitopes. consequently, these antigens or polypeptides according to the invention comprise at least the epitopic sequence as shown in FIG. 13. This epitopic sequence may be as short as the amino acid sequence given in brackets in FIG. 13.

As a further embodiment the invention also comprises immunogenic compositions which contain either one or more, preferably two or more, OspC antigens of the OspC-families of FIG. 19 or one or more OspC antigens from each of the OspC-families of FIG. 19. These immunogenic compositions correspond to patent claims 4–6.

In another embodiment, the immunogenic composition is formulated to protect against Lyme disease Borrelia strains prevalent within a particular geographic region. Thus, in one embodiment, a vaccine is formulated which is preferentially protective against Lyme disease Borrelia strains most prevalent in North America. In another embodiment, a vaccine is formulated for Lyme disease Borrelia strains most prevalent in Europe. In a third embodiment, a vaccine is formulated for Lyme disease Borrelia strains most prevalent in Austria. Vaccine formulations for each of these geographical locations are shown in Example 7.

In addition, to OspC vaccine formulations a combined OspA/OspC vaccine is considered since this could be superior to a vaccine formulated with either antigen alone;

firstly, because Lyme disease Borrelia strains may not always express one or the other of these antigens but they always express either OspA or OspC;

secondly, it has been reported that there is reciprocal regulation of these two antigens such that if the expression of one is down regulated (e.g. in response to the immune response) the expression of the other is enhanced.

thirdly, at least for in vitro studies with OspA it has been demonstrated that vaccine escape mutants could arise, a problem that can be circumvented by the inclusion of a second antigen since a double mutational event in two independent antigens is extremely improbable.

fourthly, the immune response of vaccinees to a given antigen is not uniform. The inclusion of two antigens enhances the probability that an individual, who responds poorly to either OspA or OspC, would nevertheless be protected by making a protective response to the other antigen.

Finally, it is to be expected that there could be a synergetic effect and that a more solid immunity would be obtained with a vaccine comprising OspA and OspC.

In one embodiment one or more OspC proteins from the OspC families 1–20 would be combined with one or more OspA proteins as expressed by Borrelia strains B31, Orth, H4 and KL11.

In another embodiment a combined OspA/OspC vaccine for the United States comprises an OspC from OpsCs family 2 and 3 together with an OspA as expresssed by strains B31. In a further embodiment a combined OspA/OspC vaccine For use in Europe comprises 14 OspCs from OspC families 2, 4–7, 9, 10, 15 12, 13 and 14, 15–17, 19 together with OspAs as expressed by strains B31, Orth, H4 and KL11. A further embodiment of a combined OspA/OspC vaccine for Austria comprises OspCs from families 2, 4–7, 10, 13 and 19.

The invention also comprises the use of a combination of antigens as comprised by the above-described immunogenic compositions for the manufacture of a vaccine for the treatment or prevention of Lyme borreliosis in a mammal. As a preferred embodiment this vaccine is useful for humans.

The methods for preparing of vaccines according to the present invention are designed to ensure that the identity and immunological effectiveness of the specific molecules are maintained and that no unwanted microbial contaminants are introduced. The final products are distributed and maintained under aseptic conditions. The method of immunizing a mammal against Lyme disease involves administering to the mammal an effective amount of the foregoing immunogen. Administration may involve any procedure well-known in the art. For instance, a suitable administration strategy may involve administering the above described vaccine to mammals which are known to be exposed to ticks bearing Lyme disease Borrelia, approximately 6 months to 1 year prior to the time of anticipated exposure. Any immunization route which may be contemplated or shown to produce an appropriate immune response can be employed, in accordance with the present invention, although parenteral administration is Preferred. Suitable administration forms include subcutaneous, intracutaneous or intramuscular injections or preparations suitable for oral, nasal or rectal administration.

By "substantially purified" is meant a homogenous protein free of any toxic components, thereby reducing the likelihood of an adverse reaction. "Homogenous" in this context means that at least 80% (w/v) of the protein is fully intact OspC, with nearly all of the remainder represented by OspC breakdown products. Thus, impurities in the form of media constituents and other Borrelia proteins are present, if at all, only in trace amounts. Homogenous OspC may be comprised of more than one serological form of OspC.

In this way the present invention enables the removal of unwanted, potentially immunogenic proteins which could induce autoantibodies and cause harmful autoimmune reactions in the immunized mammal. By the same token, the above-described purification method also ensures lot-to-lot reproducibility during vaccine production.

The preferred method of purification comprises the following steps:

(a) disruption of Lyme disease Borrelia cells and fractionation by centrifugation into "membrane" and "cytoplasmic" components;

(b) extraction of the membrane fraction with a non-denaturing detergent followed by centrifugation to obtain a supernatant comprising solubilized protein and to remove insoluble material as a pellet; and (c) fractionation of solubilized antigens by ion-exchange chromatography (diethylaminoethyl or "DEAE") adsorbed antigens being eluted with a NaCl gradient.

The purification method can include concentration and further purification of the antigens by:

(a) hydroxylapatite chromatography, adsorbed antigens being eluted by increasing the phosphate content of the buffer; and/or (b) immobilized metal-affinity chromatography, adsorbed antigens being eluted with imidazole.

Other elution methods known in the art include elution by a reduction in pH or by increasing concentrations of ammonium chloride, histidine or other substance with affinity for the chelated metal.

Cell disruption can be accomplished by lysing cells by shaking them in suspension in a cell mill with tiny glass beads, by sonication or in a French-press. Alternatively, antigens may be extracted directly from the cell-surface of the organism by exposing the cell to a detergent, by changing the ionic strength of the cell's environment or by slightly shifting the temperature. Alternatively, a starting material comprised of membrane blebs which are shed from cells may be used.

The extraction of the membrane fraction may be accomplished with a detergent which preferably has good solubilizing power, is non-denaturing and is compatible with ion-exchange chromatography. The preferred detergent is zwitterionic detergent 3–14 by Calbiochem, although any detergent or organic solvent may be used which has the above characteristics. The detergent is typically used at a concentration of 1% (w/v) but would be effective to varying degrees in the range of 0.01–10% (w/v). Detergent extraction is carried out at a temperature in the range of 0 to 60° C., preferably at 37° C. and should take from ten minutes to 8 hours, preferably one hour. Chaotropic agents such as urea could be used in addition to the detergent to improve the solubilization process.

The detergent solubilized antigens are then fractionated by DEAE-chromatography. Preferably, a DEAE ion-exchange resin is used but other anionic or cationic exchange resins may be used instead or in conjunction with one another. In accordance with the present invention, an ion-exchange resin comprises an insoluble matrix to which charged groups have been coupled. Functional groups used for anion exchangers include amino ethyl (AE), diethylaminoethyl (DEAE) and quaternary aminoethyl (QAE) groups. Cation-exchangers may have carboxymethyl (CM), phospho- or sulphopropyl (SP) groups. Although samples are applied to the column in a Tris suffer containing zwitterionic detergent 3–14 (1%), and the antigens are eluted with a gradient of NaCl, other formulations may be equally effective.

Antigens may be concentrated by binding them onto hydroxylapatite, according to methods well known in the art. An alternative or complementary procedure by which antigens can be further concentrated/purified is by immobilized metal-affinity chromatography. This latter method is preferred to hydroxylapatite chromatography for the purification of OspC since a better separation from OspA and OspB is achieved.

The advantage of the above described non-denaturing purification process is that the three-dimensional conformation of the protein is maintained, thereby keeping all the antibody combining sites found on the native protein, including those involved in protection. If a protein is denatured, the binding sites may be partially or completely destroyed and the capacity of the antigen to induce antibodies to the antigenic sites will be correspondingly diminished. Proteins thus altered therefore would be undesirable for use in vaccines.

Further, the invention comprises the recombinant preparation of novel OspC antigens as shown in FIG. 9B The invention also includes novel DNA sequences encoding OspC antigens according to FIG. 9A These DNA sequences are shown in FIGS. 8E–8H. Also comprised by the invention are those DNA sequences which have at least 80% homology to any of the sequences of FIGS. 8E–8H.

The invention also comprises the recombinant expression vectors in procaryotic or eucaryotic host cells, especially expression vectors useful in yeast, preferably *Pichia. pastoris*. According to a preferred embodiment of the invention the expression vector is inducible by methanol.

The invention comprises novel OspC antigens as (i) encoded by any of the sequences according to FIGS. 8E–8H or (ii) having a homology of at least 80% with any of the amino acid sequences of FIG. 9B.

The present invention is described in more detail in the following examples, which are illustrative and in no way intended to limit the scope of the invention.

EXAMPLE 1

CMAT Typing of *Borrelia Burgdorferi* Strains and Cluster Analysis of the Results Which Thereby Permits the Elucidation of CMAT Clusters, CMAT Families, "Human Disease Associated" Clones and Clonal Clusters Seventy Seven strains (see FIG. 1) were obtained from numerous sources listed in FIG. 2. Care was taken that the collection contained strains of widely differing geographical origin and from as many differing epidemiological and clinical situations as possible.

Membrane Fractions were then Prepared from all Strains as Follows:

Lyme disease Borrelia cells were harvested by centrifugation (7000×g, 20 minutes, 4° C.), the cell pellet was washed twice in PBS containing 5 mM $MgCl_2$ and the cell wet-weight was determined. The washed cells were then lysed by shaking the mixture in a Vibrogen cell-mill (Model V14, Buhler). Three minute cycles of shaking with cooling (4° C.) were repeated until lysis was greater than 99% complete, as assessed by dark-field microscopy. The lysate was then filtered on a sintered glass filter to remove the glass beads and the retained beads were washed with buffer to improve the yield of bacterial antigens in the filtrate. The lysate was centrifuged for 20 minutes at 7500×g at 4° C. to produce a crude membrane fraction termed membrane 2 or the "lsp" (low speed pellet) fraction. The supernatant was further centrifuged for 30 minutes at 100,000×g at 4° C. to produce a more purified membrane fraction, termed membrane 1 or "hsp" (high speed pellet). Both membrane fractions were washed twice in 100 mM Tris-HCL buffer pH =7.4, using the original centrifugation conditions. The membrane 2 fraction was used for typing purposes whereas the membrane 1 fractions were reserved for antigen purification.

Membrane proteins present in the membrane 2 fractions of each strain were then analyzed by SDS-PAGE, as described in Laemmli, U.K., Nature (London) 227: 680–85 (1970). Variations in molecular weight were determined by reference to the electrophoretic mobility of a set of standard proteins covering the molecular weight range of the full spectrum of membrane antigen markers used in the analysis.

The antigens are transferred to a nitrocellulose filter and are identified using a panel of monoclonal antibodies, for example, by immunoblotting methods well known in the art. Ausubel, et al., 2 CURRENT PROTOCOLS IN MOLECULAR BIOLOGY 10.8.1 et seq. (1992). Monoclonal antibodies are produced by well-known hybridoma technology, Kohler and Millstein, Nature 256: 495–97 (1975). In the preferred embodiment of the present invention, the strains set forth in FIG. 1 are analyzed. In general, the selection of a membrane antigen for inclusion in the analysis is governed by (a) the availability of monoclonal antibodies to detect it and to distinguish it from the numerous other antigens present in the SDS-PAGE membrane antigen profiles of bacterial strains; (b) by the antigen in question being present in a significant proportion of the strains analyzed i.e. a common antigen; (c) by the fact that it can be reproducibly detected in multiple, separately prepared, membrane fractions of the same strain, i.e., there is no evidence for intra-strain variation for the particular antigen in question; (d) by the fact that the antigen marker is stably expressed in the same isolate after multiple cultivation and passage and after storage for considerable time (up to 2 years); and (e) by lack of evidence by published scientific literature that the genes encoding the markers are extrachromosomally inherited or that variations of the antigens were under specific antigen variation mechanisms which can lead to intra-strain variation.

FIG. 3 indicates the monoclonal antibodies used to identify the 9 common membrane antigens used in the analysis (E90, E60, E59, E43, Fla, E29, E22 antigens, the E18+E20 antigen combined and the E10 antigen). The antigens are scored according to ascending molecular weight and, in the case where more than one monoclonal antibody exists, by their slightly differing reactivity (for example, E60 and E43), according to the reaction pattern of the antigen with those monoclonal antibodies.

FIG. 4 lists all unique combinations of 9 scores found for the strains analyzed which are represented as a 9-digit number. This 9-digit number then is designated as the common membrane antigen type (CMAT) of that strain. A cluster analysis was then performed to establish the relationship between all the CMATs observed. This was performed by determining the genetic diversity of each antigen and establishing an unweighted dissimilarity matrix calculated from the data of all unique CMATs. Absence of an individual common antigen score was treated as if it were missing data. The matrix formed was then subjected to cluster analysis with linkage by a weighted pair group method using arithmetic averages (Sneath and Sokal, supra) on an IBM compatible personal computer running CSS Statistica Statsoft software.

The resulting dendrogram of the cluster analysis is shown in FIG. 5. In general, the dendrogram indicates that the Lyme disease Borrelia population is indeed well structured. By plotting the Eigen values at which each of the clustering steps occurs, it is possible to choose the most appropriate level at which to segregate the bacteria into categories.

The most ideal position to make divisions occurs at points in the curve where there are major jumps in the Eigen values for successive clustering steps. As shown in the dendrogram of FIG. 5, this occurs at a level where there is between 68% and 88% difference in CMAT scores. This division divides the population into four major groups termed CMAT groups. A second major jump in the Eigen values for successive clustering occurs between the 40% and 52% difference between CMAT scores. This segregation divides each CMAT group into two to three clusters of individual CMATs. For convenience the 80% difference between scores was taken as the level at which CMAT grouping occurs, and 50% difference in scores at the level at which CMAT clustering occurs.

From the foregoing, it is apparent that the population of *B. burgdorferi* can be divided into four major CMAT groups, each of which is composed of two to three CMAT clusters. Each CMAT cluster was itself composed of between one and five individual CMATs. Comparison of these results with those of other population structure analysis taxinomic studies (Marconi & Garon, J. Bacteriol 174: 241–44 (1992); Boerlin et al., Infect. Immun. 60: 1677–83 (1992) Baranton et al., Int. J. Syst. Bacteriol. 42: 378–383, (1992)) indicates that the CMAT group 1 corresponds to the genospecies

*Borrelia bugdorferi* sensu stricto, that CMAT group 3 is equivalent to *Borrelia afzelii* also known as "group VS461" and that CMAT groups 2 and 4 correspond to *B. garinii* sp. nov. The reason why the CMAT analysis divided the *B. garinii* genospecies into 2 CMAT groups is unclear but it may be due to the fact that fewer markers were used than for example in the multi locus isoenzyme electrophoresis study (Boerlin et al., Infect. Immun. 60: 1677–83 (1992)).

When looking at the occurrences of particular strains within each CMAT (FIG. 5) it is apparent that 7 CMATs have more than one representative and thus can be considered as clones, i.e. strains having a common ancestry. Indeed 67i of all strains fell just within three distinct CMAT clones, for example, CMAT 4 (Clone 1:2:4) comprised 12 strains, CMAT 13 (Clone 3:2:13) comprising 23 strains, and CMAT 18 (Clone 4:2:18) with 15 strains. Notably, 76% (31 of 41,) of the human isolates analyzed were found to be distributed among these three major clones. Futhermore, if one considers CMATs 17, 18, 20 and 22 together as part of a related clonal cluster, all belong to CMAT cluster 4.2, then the human disease associated goes up to a 87%. Due to this strong association with human disease, they can be considered as "human disease associated" (HDA) clones or clonal clusters (see definitions above). If one further looks at the types of isolates found among these three major clones, it becomes evident that CMAT 13, for example, appears to be associated with the chronic skin syndrome ACA (5 strains) and that in general this clone is associated with syndromes of the skin (17 out of 19). In contrast, the other two HDA clones seem to be more prevalent in disseminating disease, that is, they are isolated form the blood or CSF from patients suffering from neuroborreliosis or Lyme arthritis. In the case of CMAT cluster 4.2 (i.e. CMATs 17,18,20 and 22) the epidemiological data seems to suggest a strong association with Neuroborreliosis. Of the 10 human isolates 6 were isolated from CSF material or from Neuroborreliosis patients, and four were isolated from patients with ECM, a syndrome normally associated with acute disease which can also be associated with neuroborreliosis. The syndrome association of CMAT 4 strains is not quite so clear cut as 2 of human isolates were isolated from blood, 3 from CSF and 1 from a patient with EM.

A further analysis of epidemiological data pertaining to the various strains reveals that the three major clones or clonal clusters have distinctive geographic distributions, and that this feature in turn correlates with general differences in the primary syndrome of Lyme disease observed within these regions. For example, CMAT 4 is the most predominant CMAT observed in North America, an area of the world where arthritic syndromes predominate. CMAT 13 and CMAT 18 are found predominantly in North Central Europe, where neurological syndromes and chronic skin syndromes predominate. Of the 3 major clones, only CMAT 4 is found in both North America and Europe (France, Austria and Russia), being widely distributed on both continents. Interestingly in areas of Central Europe, in particular Austria and Switzerland, where Lyme disease is endemic, all 3 major human disease associated clones co-exist.

The realization that human disease is predominanly caused by just one clone (CMAT 4) in CMAT group 1 (*Borrelia bugdorferi* sensu stricto) and one clone (CMAT 18) of CMAT group 3 (*Borrelia afzelii*) and a clonal cluster (CMAT cluster 4.2) in CMAT group 4 (*B. garinii* sp. nov.) allows one, in accordance with the present invention, to focus on these clones/clonal clusters with the aim of designing vaccines, such as an OspC vaccine or a combined OspC/OspA vaccine, which specifically protects against them. This vaccine then could be used in geographical regions where these clones are extremely prevalent. Furthermore, because of the differing clinical syndromes asociated with the differing clones, one can target a vaccine against these clones and, hence, in effect design vaccines to protect against specific syndromes.

EXAMPLE 2

Development of an OspC Serovar Typing Scheme to Analyse the Serological Variation of the OspC Antigen of Lyme Disease Borrelia Preparation of Anti-OspC Antibodies A panel of 25 monoclonal antibodies was produced against (a) four purified OspC proteins derived from (1) the Austrian strain Orth (BBM 34–39); (2) the German strain PKO (BBM 42–45); (3) the Czechoslovakian strains E61 (BBM 46, 47, and 49) and (4) KL10 (BBM 40–41); (b) an OspC protein enriched cocktail of antigens derived from the Austrian strain W (BBM 22, 24, 25, 27, 28, and 29); and (c) a membrane 2 fraction of the Czech strain M57(BBM 75–77).

The anti-OspC protein specificity of various monoclonal antibodies were confirmed by surfblot analysis against a membrane fraction of strain W or M57 in the case of BBM22, 24, 25, 27–29, and BBM 75–77, respectively, and in the case of the others by line blot analysis against the appropriate purified protein.

Membrane ELISA Method

Serotyping of the OspC proteins was performed using a standard membrane ELISA technique. Membrane 2 fractions of all strains, prepared as describe in Example 1, were diluted to 0.1 mg/ml in phosphate buffered saline (PBS) pH 7.4 dispensed into individual wells of microtiter plates. The plates were allowed to dry out overnight at 37° C. Prior to use, the plates were washed twice in PBS, and then 50 ml of the diluted antibody solution in PBS containing 1% human albumin were added to each well and the plates incubated for one hour at 37° C. The plates were washed four times before the addition of the anti-mouse IgG alkaline phosphates conjugated antibody. The plates were incubated at 37° C. for another hour before being washed four times prior to the addition of substrate, in order to estimate the amount of bound antibody.

Initially all strains were tested against all 25 monoclonal antibodies in order to see which monoclonals were most appropiate for serotyping purposes. Attempts were made to establish uniform positive and negative test criteria, however it became clear that this was not possible due to the vastly different levels of expresssion of the Osp C antigens within differing strains. To overcome this problem membrane 2 fractions were analysed be Western blot method, transfered to nitrocellulose and stained using Aurogold. Those strains which expressed no or low amounts of Osp C proteins (15 strains in all), as judged by the absence of a major protein in the 22 to 28 Kd molecular weight range, were removed from the study. Despite this, in a number of cases (for example, when using BBM 28, 29, 37 43, and 45), there was still no readily observed distinction between postive and negative results and thus these monoclonal antibodies were deemed unsuitable for typing purposes. All these antibodies recognise common epitopes and are thus of little discriminatory value anyway. Based on the strain coverage data of the initial analysis, a number of monoclonal antibodies were also found to recognise similar epitopes, e.g. BBM 24, 25 and 27, BBM 38 and 39 and BBM 75, 76, and 77, and thus only one from each group (BBM 24, BBM 39 and BBM 77, respectively) were used in the final serovar typing scheme. By removing these strains and monoclonal antibodies it was then possible to establish the criteria of a positive reaction as being one in which the optical density value obtained was significantly (three times) higher than the background level of negative strains. In practice this meant that a positive result had an Optical Density (OD) value greater than 0.6. All positive reactions were also confirmed by western blot analysis of the same membrane preparations. As a result of the western blot analysis it was discovered that BBM 48 strongly cross-reacted with a protein of approximately 60 kilodaltons, and gave rise to numerous false positive results in the ELISA analysis. Thus BBM 48 it was also omitted from the serovar analysis. Consequently the serovar analysis was somewhat simplified using only 13 of the inital 25 anti-OspC antibodies available.

The reaction pattern of each strain with the complete panel of 13 monoclonal antibodies then was collated, and each unique pattern designated as a "serovar" (see FIG. 6). In the collection of 62 strains ultimately analyzed, 16 unique serovars were observed, thereby demonstrating the enormous degree of serological heterogeneity displayed by this membrane protein. The number of positive reactions observed among individual serovars ranged from between 1 to 7.

The full listing of serovar found for each strain is presented in FIG. 12. As can be seen 12 strains (19% of the strains analysed) did not react with any of the panel of 13 monocloal antibodies (denoted by "NR" non-reactive) and were deemed non-typable. Taken together with the strains that were ommitted because of lack of or low level of expression (15 strains), a total of 22% of the strains available could not be typed. The frequency of occurrence of the serovars among the 78% of strains that could be unequivicably typed varied considerably. only single representatives of serovars 6, 8 and 9 were observed whereas 10 strains were of serovar 2, the most common serovar. There were strong correlations between the family and genotype of the OspC protein and its serovar. Indeed in most cases there seemed to be a one to one relationship e.g. for families 1, 2, 4, 5, 7, 9, 10, 14, and 15. Families 3, 12, 13, 17, 18 and 19 could either not be tested or were non typable using the monoclonal antibodies currently available. Families 6, 8 and 11 could be further subdivided serologically into 2 or 3 serovars, however it is interesting to note that the genotypes of these families also showed some diversity. One serovar (serovar 16) was observed in more that one family (families 16 and 20). This might have occurred because there are only two positive reactions in this serovar and thus the current monoclonal antibodies were not able to discriminate between the two families.

EXAMPLE 3

Restriction Fragment Length Polymorphism (RFLP) Analysis of ospC Heterogeneity

The ospC gene from strain Orth was cloned and the nucleotide sequence determined as previously described (U.S. application, Ser. No. 07/903,580). Oligonucleotides corresponding to the proximal (coding strand, ATGAAAAAGAATACATTAAGTGC (SEQ ID NO:55), start codon underlined) and distal (non-coding strand, TAA TTAAAGGTTTTTTTGGAGTTTCTG (SEQ ID NO:56), stop codon underlined) ends of the ospC gene from strain Orth were then used in the polymerase chain reaction (see example 4) to amplify the OspC genes from 77 strains in our culture collection. All strains tested, including 14 strains from the United States, yielded PCR fragments of the predicted size (627–642 bp) indicating that the plasmid-encoded ospC gene is not only stably maintained but is much more prevalent than previously supposed. The failure to detect the OspC antigen in vitro grown cultures is unlikely to be due to the absence of the ospC gene but rather to the absence or low level of antigen being expressed.

The polymorphism among ospC genes from different strains was determined by analysis of the restriction fragment patterns obtained after digestion of the PCR amplified ospC gene (prepared as described above) with the restriction enzymes Dpn11, Dde1 and Dra1. An analysis of the data from the 82 strains (i.e. experimental data from all 77 strains in our culture collection plus information deduced from 5 published ospC sequences; see FIG. 1) revealed the presence of 35 distinct RFLP ospC types. The number and sizes of the fragments experimentally determined using standard procedures, was confirmed in many instances by sequencing i.e. for at least one representative of RFLP types 1–23, type 24 is based on the sequence data of Padula et al. The RFLP patterns associated with each RFLP type are shown in FIG. 7. Where available, the fragment sizes deduced from sequence information has been presented (RFLP types 1–24) in preference to the measured values. A complete listing of the RFLP-types for each strain analysed is given in FIG. 12).

EXAMPLE 4

PCR Amplification and Nucleotide Sequencing of Different Alleles of the ospC Gene and Cluster Analysis of the Deduced Amino Acid Sequences As described in Examples 1 and 2, and summarized in FIG. 12, it was possible to classify Borrelia strains into OspC serovars and OspC RFLP-types. Strains representing ospC RFLP-types 1–17 and 19–23 were selected, the ospC gene was amplified by the polymerase chain reaction and the nucleotide and deduced amino acid sequence determined. In several cases, the relationship between closely related OspC proteins was investigated as a further check on the validity of the typing systems and to check for further undetected heterogeneity within OspC types. A total of 27 ospC genes were PCR amplified and sequenced as described below. The sequence information has been used to classify OspC proteins into OspC families.

Materials and Methods

A frozen Borrelia stock cell-suspension was thawed and 2 $\mu$l ($5\times10^6$–$1\times10^8$ cells/ml) was centrifuged for 5 minutes at top speed in a Heraeus Biofuge A microfuge. The cell pellet was resuspended in 10 $\mu$l of 1×TAQ-buffer (Boehringer Mannheim), overlaid with 50 $\mu$l mineral oil (Pharmacia), then incubated in a boiling water bath for 8 minutes and placed immediately on ice. To the cell-lysate was added 90 $\mu$l of a reagent mixture [9 $\mu$l 10×Taq polymerase buffer, Boehringer Mannheim; 2 $\mu$l 10 mM DNTP solution, Boehringer Mannheim; 5 $\mu$l primer 1 (ATGAAAAAGAATACATTAAGTGCG)(SEQ ID NO:57), 10 mM stock; 5 $\mu$l primer 2 (ATTAAGGTTTTTTTGGAGTTTCTG)(SEQ ID NO:58), 10 mM stock; 0,5 $\mu$l 5,000 U/ml Taq polymerase, Boehringer Mannheim; and 68.5 $\mu$l H$_2$O]. DNA amplification was performed in a LKB Thermocycler (95° C. for 36 seconds, 53° C. for 60 seconds, 70° C. for 84 seconds, 30 cycles). Amplification was monitored by analyzing 5 $\mu$l of the product on a 1% (w/v) agarose gel in Tris-Acetate buffer (40 mM Tris acetate, 2 mM EDTA, pH 8.0), staining with ethidium bromide and visualization under UV light. Amplified products were concentrated using Spin Bind microcentrifugation cartridges (FMC). DNA then was collected in 30 μl H$_2$O and recovery was monitored by running 2 μl of the purified product on an agarose gel as described above.

Amplified DNA fragments (2–7 μl) were prepared for sequencing on a LKB Thermocycler (25 cycles at 95° C. for 36 seconds, 53° C. for 30 seconds, 70° C. for 80 seconds) using the Auto Cycle Sequencing kit (Pharmacia) with the fluorescein labeled primers 5'-ATGAAAAAGAATACATTAAGTGCG-3'(SEQ ID NO:59) and 5'-ATTAAGGTTTTTTTGGAGTTTCTG-3' (SEQ ID NO:60). Samples were electrophoresed on a 6% polyacrylamide sequencing gel using an automated laser fluorescent [ALF] sequencing apparatus (Pharmacia LKB) as specified by the manufacturer. The nucleotide sequence data files from the ALF were collated and analyzed using the software package DNASIS and the deduced protein sequences with PROSIS (Pharmacia-LKB).

The amino acid sequences for the OspC proteins from 24 different strains of the Lyme disease spirochetes (i.e. 22 sequences from this study and 2 published sequences for strains 2591 and PBI) were aligned by the fast/approximate method of Wilbur and Lipman, PNAS USA 80: 726–30 (1983), and the similarity scores thus generated were used to construct a dendrogram by the UPGMA method (a form of cluster analysis) of Sneath and Sokal, supra. These analyses were performed using the software package Clustal V (Higgins and Sharp, CABIOS 5: 151–53 (1989); Higgins et al., CABIOS (1991).

Results and Discussion

The aligned, nucleotide and deduced partial amino acid sequences for the OspC genes and proteins from 24 strains, representing 24 different RFLP-types, are shown in. FIGS. 8A–9B (SEQ ID NO:1–54). Since the amino acids preceding the first cysteine residue (amino acid 19 in the Orth sequence) in the OspC protein are the leader sequence and not present in the mature protein (the sequence FISC is a putative signal peptidase cleavage site) they were not included in the sequence comparison. At the carboxy terminal end of the protein, the last 16 amino acids were excluded. This includes the region corresponding to the binding site of primer 2 (equivalent to last 7 amino acids) and then a gap of 9 further amino acids until the first sequence data were obtained. This terminal portion of the OspC genes appears to be highly conserved and of minor importance in generating the diversity observed among the OspC proteins as indicated by the ability to amplify and sequence the ospC gene from all strains tested using primer 2. Moreover, monoclonal antibodies which bind to this region of OspC are broadly reactive (for example, BBM 29, 42 and 45 in FIGS. 13 and 14.

The OspC sequences are highly variable with the most distantly related amino acid sequences (B. burgdorferi strain 297, SEQ ID NO:12 and B. garinii strain IP90, SEQ ID NO:42 showing only 59% amino acid sequence identity (80% similarity). However, no sequence differences were detected between members of the same RFLP-type indicating that this typing method very accurately represents the heterogeneity among ospC genes (i.e. the OspC sequences for RFLP-type 1 strains VS215, VS219 and DK7 are identical to that of ZS7, SEQ ID NO:9; RFLP-type 2 strains IP2, SEQ ID NO:5, and 26816 are identical to B31; RFLP-type 6 strains H15 and ACA1 are the same RFLP-type 7 strains PKO and DK26 are identical to JSB, SEQ ID NO:25; RFLP-type 10 strains H4 and W, SEQ ID NO:31, are the same; RFLP-type 13 strains 871104 and KL11, SEQ ID NO:47, are identical; RFLP-type 14 strains 20047 and VS185 are the same).

The degree of relatedness between the partial OspC amino acid sequences determined by cluster analysis is presented as a dendrogram in FIG. 10. OspC proteins from strains of the same species are more closely related to each other than to OspC proteins from different species. Nevertheless, even within one species, considerable variability is evident. The OspC sequence diversity is particularly high among the B. garinii strains, as indicated by the deeper branching observed within this part of the phylogenetic tree and the larger number of OspC variants associated with B. garinii than with the other two Borrelia species. The clonal structure of ospC inheritance suggests that there has been no significant exchange of genetic material, either by intragenic recombination or horizontal transfer of the plasmid-encoded ospC, between the different Lyme disease Borrelia species.

OspC proteins have been assigned to OspC families, an OspC family being defined as a group of OspC proteins that have more than 80% amino acid sequence identity over the first 92% of the mature OspC protein i.e. excluding the information for the 18aa leader sequence and the final 16aa. Eighteen different OspC families are depicted in FIG. 1 but two further OspC families (19 and 20) have been identified from incomplete sequence information for the OspC proteins from strains H13 (SEQ ID NO:51) and 28691 (SEQ ID NO:1) which has not been included in the dendrogram.

Despite the great diversity among the OspC proteins, the first third of the mature OspC protein is conserved (FIG. 10), with strains of the same species showing around 80–90% sequence identity in this region. However, the sequence identity between OspC proteins from different species is not so high in this part of the protein due to the presence of species-specific sequence motifs at the amino-terminal end of the OspC protein. As indicated above, the carboxy-terminal portion of OspC, which has not been shown, is also apparently highly conserved. The intervening region (i.e. the lower two blocks of FIG. 9 between amino acid residues KKI and NS) is highly variable and the major source of diversity associated with OspC. It is to be expected that serotype-specific epitopes would lie within this variable region. Analysis of the hydrophilicity profiles of the individual protein sequences, by the method of Hopp and Woods, found that the highest hydrophilic peak, highly predictive of the existence of an epitcpe, lies within this region. More specifically, despite the great variability between the OspC sequences in this region a putative epitope invariably lay between amino acid residues 120–155 of the mature protein. In the OspC of strain Orth, the hydrophilic peak occurs at residues 136–141 (DNDSKE), a region of high flexibility and a predicted β-turn, parameters which would also be indicative of an epitope (analyses done using PC/GENE).

EXAMPLE 5

Epitope Mapping of the Anti-OspC Monoclonal

The epitopes of certain of the anti-OspC monoclonal antibodies were mapped using a commercial available Custom Designated Epitope Scanning kit from Cambridge Research Biochemicals Ltd., Gradbrook Park, Northwich, Cheshire, England which uses either the pin technology method described by Geysen et al., J. Immunol. Methods 102: 259–74 (1987) or an biotinylated peptide ELISA or Dot Blot method described by the manufacturer. The 2026 custom synthesized peptides tested were single step, overlapping 10 mers of the OspC proteins sequences shown in FIG. 9. Overlapping peptides of the signal peptide sequence of strain Orth and the C terminal ends of the OspC proteins of Strains Orth PKO and B31 were also included in the analysis.

The combined sequence of sequential peptides reacting with a monoclonal antibody is described as a "full epitope sequence". FIG. 13 lists the full epitope sequence of those monoclonal antibodies for which epitopes could be discerned (SEQ ID NO:67–76). The sequence enclosed within brackets, [ ], includes the amino acids common to all reacting peptides and therefore form an important part of the epitope. The location of each full sequence within a generalized OspC protein the protein is shown in FIG. 14. In one instance, e.g. with, a number of epitopes could be discerned, however, only that for the primary epitope, i.e., the most highly reactive, is given (FIG. 13) and shown (FIG. 14). In cases where the monoclonal reacted with peptides corresponding to similar regions in more than one OspC protein only that for the Orth strain is given. Conversely, where the monoclonal antibody does not react with the Orth protein (e.g. BBM 43) the reacting sequence given is that for the homologous strain (PKO). At the bottom of FIG. 13 the monoclonal antibodies are grouped into categories based on the frequency of occurrence of the epitope they recognize which are shown in the upper part of the figure. As can be seen, over half of them recognize highly-specific epitopes, in that they occur in fewer than ten of the strains analyzed. Five of the monoclonal antibodies recognize epitopes of intermediate occurrence, while the seven remaining can be considered to recognize common epitopes because they occur in more than twenty five of the of the 77 strains analyzed. The monoclonal antibodies which were found to be suitable for the serovar analysis are denoted in FIG. 13 by an asterix.

It is interesting to note that it was primarily the monoclonal antibodies that recognize common epitopes (BBM 28, 29, 34, 37, 42, 43, and 45) or those of intermediate occurrence (BBM 22, 35, and 40) which could be unequivocally mapped. Indeed only three monoclonal antibodies which could be considered as type specific (BBM 38, 39 and 44), i.e. reacting with fewer than 10 strains, could be mapped. Both BBM 38 and 39 have the same strain reaction pattern and mapped to the same region (amino acid 155 and 170). Base on hydrophilicity plots of the amino acid sequence of the Orth protein, a hydrophilic peak and predicted β turn coincides with this region, parameters highly indicative of an epitope. The epitope of BBM 44 lies between amino acid 79 to 90, also an area of considerable variation. Unfortunately none of the epitopes of the other type specific monoclonal antibodies could be mapped, suggesting that they are dependent on the confirmation of the molecule. However, since all 3 type specific antibodies map to regions that are among the most variable of the protein, it is highly likely that it is also involved in other type specific epitopes. Interestingly, BBM 28 which reacts with an epitope of high frequency also maps to same regions as BBM 38 and 39. The reasons for this is unknown however there may be slight differences in the number and the actual amino acids involved at the binding site which bring about this ambiguity.

Four of the antibodies (BBM 29, 42, 43 and 45) which react with common epitope map at the distial C terminal end of the protein (amino acids 200 to 212), where as two others react close to the N terminal end of the protein (amino acids 41 to 35 67), regions which have been shown to be highly conserved. The monoclonal antibodies recognizing epitopes with intermediate occurrence mapped within the semi-conserved regions (amino acids 103 to 114 and amino acids 176 to 196) of the molecule.

These result were also confirmed in a further experiment where polyvalent rabbit sera specific for membrane 2 fractions of strains expressing each of the 16 serovar variants of the Osp C protein were screened against the 203 overlapping peptides of the Orth protein. All common, cross reacting epitopes were found within the conserved and semi-conserved regions outlined above. Interestingly sera from strains of CMAT group 1 (*B. burgdorferi* sensu stricto) did not cross react as frequently as those sera from strains of CMAT groups 3 (*B. afzelii*) and 4 (*B. garinii*)

EXAMPLE 6

Cross-Protection Studies in Gerbils

To ascertain whether cross-protection between different OspC families was possible, OspC proteins were purified from *B. burgdorferi* strain ZS7 (OspC family 1), *B. afzelii* strain PKO (OspC family 7) and *B. garinii* strain W (OspC family 10) and used as immunogens in the gerbil model of Lyme borreliosis against a challenge with *B. afzelii* strain Orth (OspC family 5). To test protection within a family, the OspC from strain H7 (OspC family 5) was used as an immunoqen against strain Orth. The OspC from strain H7 belongs to the same serovar and RFLP-type as the OspC from strain Orth.

Gerbils were given either a single, subcutaneous immunization of purified OspC (20 µg protein/200 µl, adjuvanted with TiterMax #R-1 (CytRx), that is, were prepared as a water-in-oil (squalene) emulsion with a synthetic immunomodulator (copolymer CRL89-41) or two intraperitoneal injections of OspC (10 µg protein/500 µl) adjuvanted with aluminium hydroxide. The purified antigens were prepared from strains by methods described in U.S. patent application Ser. No. 07/903,580, the contents of which were previously incorporated above by reference. Three and a half weeks after the first immunization, blood samples were taken from the eye and plasma prepared so that the antibody response to the immunogen at the time of the challenge could be ascertained (unimmunized control animals were likewise treated). Four weeks after the first immunization, the animals were challenged intraperitoneally with $10^4$ cells (25–100 $ID_{50}$) of strain Orth, as were a group of unimmunized control animals. The challenge suspension was also titrated in unimmunized gerbils to determine the dose required to infect 50% of the animals. After a further two weeks, the animals challenged with the $10^4$ dose were killed and the bladder, heart, kidneys and spleens cultured in BSK medium. Cultures were inspected for spirochetes at weekly intervals, from the second to the sixth week post-inoculation, by dark-field microscopy. Blood also was taken and the resultant plasma analyzed by western blotting for sero-conversion, i.e. the development of antibodies post-challenge to antigens from strain Orth other than the immunogen. There was good agreement between the cultural and serological tests used to ascertain which animals were infected. Only serological testing was used for the ID(50) determinations but in this instance the animals were bled three weeks post-challenge, the extra time being given to ensure that the antibody response in infected gerbils was sufficiently strong to be easily detected.

There were no signs of cross-protection between species i.e. OspC proteins from OspC families 1 (*B. burgdorferi*) and (*B. garinii*) were ineffective as immunogens against the challenge strain Orth (*B. afzelii*). Likewise there was no sign of cross-protection between different OspC families of the same species i.e. the OspC protein from an OspC family 7 isolate (*B. afzelii* strain PKO) was ineffective as an immunogen against a challenge with strain Orth which expresses an OspC protein from OspC family 5. By contrast, immunization with the OspC protein from strain H7 (OspC family 5) was effective against a challenge strain Orth (OspC family 5). These data (FIG. 15) indicate that cross-protection between the OspC families is unlikely and that protection within a family is possible. A multivalent vaccine comprising one or more types of OspC proteins from each of the OspC families should be sufficient to protect against most Lyme disease Borrelia strains.

EXAMPLE 7

Frequency of Occurence Geographical Distribution of Various Families of OspC Proteins Associated with Human Disease Due to the high degree of variability of the OspC protein, it is extremely difficult to design vaccine formulations which give good protective coverage, yet do not require the inclusion of excessively large numbers of variants in order to achieve this goal. One way of optimizing the selection of OspC variants would be to determine which OspC variants are associated with human disease and occur with a high frequency. Rare OspC variants or OspC variants rarely associated with human disease would thus be excluded from any vaccine formulation with minimal loss of vaccine efficacy. Furthermore, if the vaccine is designed only for use in a particular geographic region, it would be unneccessary to include those OspC variants not prevalent among the Lyme disease Borrelia of that region. Using the epidemiological and OspC typing information on the Borrelia strains used in this study (FIG. 12) it has been possible to make selections on the OspC variants should be included in an OspC vaccine(s).

An analysis of the *B. burgdorferi* isolates (CMAT group 1 including strain 25015; total 23 strains) shows that the most prevalent OspC variants among those strains are those belonging to families 1 and 2. Family 1 strains are all European isolates and may cause human disease, although only 1 of the 5 strains was a human isolate which may be an indication that these strains are not highly virulent. Family 2 strains are the single most common type of OspC family with 10 members. Unlike family 1 strains, these strains are widely distributed with isolates from the United States, Europe and Russia. Family 2 strains are clearly associated with human diease with 50% of the isolates being clinical specimens. The remaining 8 *B. burgdorferi* isolates tested are all United States isolates and they are very diverse in terms of the OspC that they express, since each strain expresses a different OspC RFLP type. Only one of these strains (strain 297, family 3) was isolated from a case of Lyme disease. The family 2 and 3 strains belong, with the exception of strain 25015, to one of the 3 major human disease related clones CMAT type 1.2.4. (FIG. 5). The 26 strains of *B. afzelii* (i.e. Group VS461, CMAT group 3) fall into 6 discrete families; OspC families 4–8 and family 16 with 5, 4, 6, 2, or 4 members respectively. Except for one Japanese isolate, all the strains were from Europe; Austria (14), Czech Republic (4), Denmark (1), Germany (2), Italy (1) Slovenia (1), Sweden (1) and Switzerland (1). Eighty-eight percent of the European isolates were of human origin, with 80% of the isolates being from skin biopsies and 8% from blood samples. These data reflect a strong association between *B. afzelii* strains and the development of dermatological forms of Lyme disease. The human isolates were distributed evenly throughout the various OspC families. The Austrian isolates belonged predominantly to families 4–6 (86%) but single representatives were also found in families 7 and 8. The low incidence of Austrian isolates among OspC family 7 (i.e. 1/5) and the absence of isolates from family 16 (0/4) suggests that within Europe there are geographical variations in the prevalence of the various *B. afzelii* OspC families. Nevertheless, *B. afzelii* strains from the OspC families 4–8 and 16 are widely scattered throughout Europe. These strains are almost exclusively members of another major human disease related clone, namely 3.2.13. (FIG. 5).

Thirty *B. garinii* strains (i.e CMAT group 4, excluding atypical strains 19857 and 19952, and CMAT 2 strains 20047, IP90 and NBS16) can be sub-divided into 9 OspC families plus 2 RFLP types for which there is no family assignment. Fifty-three percent of the *B. garinii* strains tested were human isolates and these strains are distributed throughout all but one (RFLP 34) of the OspC types. Seventy-five percent (12/16) of these *B. garinii* strains were isolated from cases of neuroborreliosis with the remainder being skin isolates. Therefore, *B. garinii* is primarily associated with neuroborreliosis, although the occurence of skin isolates is to be expected since the development of a skin-lesion (EM) is a manifestation common to all forms of Lyme disease irrespective of the causative agent. Strains of OspC family 13 were the most commonly isolated OspC type, accounting for 23% (7/30) of the total *B. garinii* OspC types and 25% (4/16) of the human isolates. Strains of this OspC family are widespread within Europe and include isolates from 6 different countries. OspC family 11 is also widely distributed and occurs reasonably frequently (17% or 5/30) but the association with human disease is less clear, since only one isolate was of human origin, but this may reflect sampling error and the small numbers of strains analysed. These latter comments are also applicable to strains of OspC family 14 (4 strains but only 1 human isolate). Isolates from the other OspC families (9, 10, 12, 15, 17, 19 and RFLP types 33 and 34) were found at a lower frequency. However, for a vaccine against Austrian *B. garinii* strains OspC families 10 and 19 should be considered, in addition, since all 4 *B. garinii* isolates from Austria belonged to these 2 OspC families.

In addition, to the direct analysis of Borrelia strains, as described above, it is also possible to determine the prevalence of the various OspC variants and their association with human borreliosis indirectly. This can be achieved by testing the specificity of OspC antibodies in the serum from Lyme disease patients. Fifty sera taken from patients in the Prague area (Czech Republic) suffering from EM (15), ACA (15), neurological disorders (10) or joint and muscle associated syndromes (10) have been tested for antibodies to OspC. When screened against a panel of 18 strains, 17 (34%) of the sera (3 EM, 10 ACA, 3 Lyme arthritis and 1 neuroborreliosis) were found to react with one or more of the 16 OspC families tested (FIG. 16). Twelve of the sera reacted specifically with just one OspC [family 5 (4×), family 7 (3×), family 6 (2×), family 8, 13 and 14 (1×)] Three sera reacted with both families 4 and 6 while 2 other sera were broadly cross reactive reacting with 6 and 8 of the families tested. Therefore, Borrelia strains expressing OspC variants from OspC families 5–7, 13, 14 and probably 4 are present in the Czech Republic. This serological data is consistent with, and therefore substantiates, the results obtained from the strain analysis for the neighbouring country Austria.

Based upon the results described above, vaccines have been formulated for use in;

1) United States; OspCs from OspC families 2 and 3
2) Europe; 14 OspC variants from OspC families 2, 4–7, 9, 10, 12, 13, 14, 15–17 and 19
3) Austria; 8 or more OspCs from OspC families 2,4–7, 10,13 and 19.

EXAMPLE 8

Expression of Recombinant OspC in *P. pastoris*
Construction of the *Pichia Pastoris* OspC Expression Vector

| B. burgdorferi Strain | Primer | Vector pHIL-A1 digested |
|---|---|---|
| Orth<br>SEQ ID NOS 63 and 64 | 5'-AA ACG ATG TGT AAT AAT TCA GGG AAA GG-3'<br>5'- ATTAAGGTTTTTTTGGTTTCTG-3' | SfuI/Klenow |
| KL10<br>SEQ ID NOS 65 and 66 | 5'-GGGACTTCGAAACGA ATG TGTAATAATTCAGGTGGG-3'<br>5'-GGA ATT CAT TAA GGT TTT TTT GGA-3' | SfuI/EcoRI |
| ZS7<br>SEQ ID NOS 77 and 66 | 5'-CGGACTTCGAAACGA ATG TGTAATAATTCAGGGAAAG-3'<br>5'-GGA ATT CAT TAA GGT TTT TTT GGA-3' | SfuI/EcoRI |
| B31<br>SEQ ID NOS 77 and 66 | 5'-CGGACTTCGAAACGA ATG TGTAATAATTCAGGGAAAG-3'<br>5'-GGA ATT CAT TAA GGT TTT TTT GGA-3' | SfuI/EcoRI |
| E61<br>SEQ ID NOS 77 and 66 | 5'-CGGACTTCGAAACGA ATG TGTAATAATTCAGGGAAAG-3'<br>5'-GGA ATT CAT TAA GGT TTT TTT GGA-3' | SfuI/EcoRI |
| PK0<br>SEQ ID NOS 77 and 66 | 5'-CGGACTTCGAAACGA ATG TGTAATAATTCAGGGAAAG-3'<br>5'-GGA ATT CAT TAA GGT TTT TTT GGA-3' | SfuI/EccRI |

The recombinant *P. pastoris/E. coli* shuttle vector pHIL-A1 (provided from Phillips Petroleum) was used to clone the OspC coding sequence of *B. burgdorferi*. A panel of strains comprising one or more representatives from each family was selected and the OspC gene was amplified by the polymerase chain reaction. The coding sequence of the mature OspC protein starting with the first cysteine amono acid (amino acid 19 in the OspC protein sequence from strain Orth) was amplified by using the strain specific primers deduced from the OspC nucleotide sequences as disclosed U.S. Ser. No. 07/903,580 (EP 0 522 560).

To create the 5' and 3' end of the *B. burgdorferi* Orth OspC gene, the polymerase chain re Column: Protein-PAK DEAE 5PW from Waters
Sample: 45 ml dialysed antigen preparation
Equilibration buffer (A): 10 mM Tris/HCl pH 7.5
Eluation buffer (B): 10 mM Tris/HCl, 1 M NaCl, pH 7.5
Flow rate: 4 ml/min
Gradient: 0% for 70 min, 0–100% for 50 min The column was equilibrated with buffer A and the antigens eluted with increasing amounts of NaCl. To identify fractions containing the antigen of interest, aliquots of fractions were precipitated with acetone and the pellets were analyzed by SDS-PAGE and/or immunoblotting.

Fractions from the DEAE ion-exchange chromatography separation enriched for OspC antigen were further purified by immobilized metal-affinity chromatography as described in EP 0 522 560.

Large Scale Production of OspC protein in the Fermenter

The production of OspC was examined in continuous fermentation run. Each run was performed using a fermenter equipped with monitors and controls for pH, dissolved oxygen, agitator speed, temperature, air flow and oxygen flow. Temperature was held at 30° C. Cell yield was determined from washed cell wet weight.

Inocula for the fermenter runs were grown in 2 l Erlenmeyer flasks containing 500 ml of modified FM21 medium as disclosed in EP 0 263 311. The fermenter cultures grown in the batch mode were propagated with glycerol as sole source of carbon and energy. Continous cultures were established with constant glycerol feed until a biomass concentration of 500–700 g wet cell weight/litre was reached. Once baseline control samples were taken, methanol was added to the culture as methanol-salts-biotin feed over a period of several days to keep the methanol concentration between 0.05 and 1.5 %. Produced biomass were removed every day. *P. pastoris* cells were collected by centrifugation and resuspended in buffer (150 mM Tris/HCl, 2 mM EDTA, 1 mM benzamidine hydrochloride, 0,1% $NaN_3$, pH 7.4). Cell lysates were obtained by using French press. OspC protein concentration was determined by the method of Bradford. Preliminary results showed an antigen production of about 100 fold increased yield of OspC antigen (per unit volume culture)derived from *P. pastoris* compared to the yields obtained from the *B. burgdorferi* strains.

Immunization and Challenge (Protection) Studies of the *P. Pastoris* Derived OspC Antigen Protection studies were performed in gerbils as described in example 6. Twenty microgram amounts of OspC from *P. pastoris* (cloned from strain Orth) or Borrelia strain Orth were tested for their protective efficacy as shown in FIG. 18. All gerbils immunized with *P. pastoris* derived OspC were protected against a challenge with the homologous strain Orth and results are comparative to protection studies obtained with Borrelia derived OspC antigen.

What is claimed is:

1. A vaccine effective to immunize a susceptible mammal against Lyme borreliosis infection comprising a) an immunogenic amount of an OspC antigen consisting essentially of SEQ ID NO. 2; an OspC antigen consisting essentially of SEQ ID No. 4; an OspC antigen consisting essentially of SEQ ID No. 8 and an OspC antigen consisting essentially of SEQ ID No. 12, wherein said amount is in the range of 1 to 100 ug per antigen b) an antigen selected from the group consisting of an OspA antigen from *B. burgdorteri* strain B31, an OspA antigen from *B. burgdorferi* strain Orth and an OspA antigen from *B. burgdorferi* H4, and an OspA antigen from *B. burgodorferi* strain KL11, and c) a physiologically acceptable excipient.

2. The vaccine of claim 1, wherein said mammal is a human.

3. The vaccine of claim 1, wherein said amount is in the range of 10 to 50μ per antigen per dose.

4. The vaccine of claim 1, wherein said OspC antigen is a recombinant polypeptide produced in transformed microbial cells.

5. A method of immunizing a mammal against Lyme borreliosis comprising administering to said mammal the vaccine of claim 1.

6. The method of claim 5, wherein said mammal is a human.

7. The method of claim 5, wherein said vaccine is administered in an amount in the range of 10 to 50 micrograms per antigen per dose.

* * * * *

SEQUENCE LISTING (1) GENERAL INFORMATION:

(iii) NUMBER OF SEQUENCES: 77

(2) INFORMATION FOR SEQ ID NO: 1:

(i) SEQUENCE CHARACTERISTICS:
       (A) LENGTH: 576 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (A) ORGANISM: Borrelia burgdorferi
       (B) STRAIN: 28691

(ix) FEATURE:
       (A) NAME/KEY: CDS
       (B) LOCATION: 1..576

(xi) SEQUENCE DESCRIPTION: SEQ ID NO: 1:

```
TGT AAT AAT TCA GGA AAA GAT GGG AAT GCA TCT GCA AAT TCT GCT GAT        48
Cys Asn Asn Ser Gly Lys Asp Gly Asn Ala Ser Ala Asn Ser Ala Asp
  1               5                  10                  15

GAG TCT GTT AAA GGG CCT AAT CTT ACA GAA ATA AGT AAA AAA ATT ACA        96
Glu Ser Val Lys Gly Pro Asn Leu Thr Glu Ile Ser Lys Lys Ile Thr
             20                  25                  30

GAA TCT AAC GCA GTT GTT CTG GCC GTG AAA GAA GTT GAG ACC TTA CTT       144
Glu Ser Asn Ala Val Val Leu Ala Val Lys Glu Val Glu Thr Leu Leu
         35                  40                  45

GCA TCT ATA GAT GAA CTT GCT ACC AAA GCT ATT GGT AAA AAA ATA GGC       192
Ala Ser Ile Asp Glu Leu Ala Thr Lys Ala Ile Gly Lys Lys Ile Gly
     50                  55                  60
```

-continued

```
AAT AAT GGT TTA GAG GCC AAT CAG AGT AAA AAC ACA TCA TTG TTA TCA      240
Asn Asn Gly Leu Glu Ala Asn Gln Ser Lys Asn Thr Ser Leu Leu Ser
 65              70                  75                  80

GGA GCT TAT GCA ATA TCT GAC CTA ATA GCA GAA AAA TTA AAT GTA TTG      288
Gly Ala Tyr Ala Ile Ser Asp Leu Ile Ala Glu Lys Leu Asn Val Leu
                 85                  90                  95

AAA AAT GAA GAA TTA AAG GAA AAG ATT GAT ACA GCT AAG CAA TGT TCT      336
Lys Asn Glu Glu Leu Lys Glu Lys Ile Asp Thr Ala Lys Gln Cys Ser
            100                 105                 110

ACA GAA TTT ACT AAT AAA CTA AAA AGT GAA CAT GCA GTG CTT GGT CTG      384
Thr Glu Phe Thr Asn Lys Leu Lys Ser Glu His Ala Val Leu Gly Leu
        115                 120                 125

GAC AAT CTT ACT GAT GAT AAT GCA CAA AGA GCT ATT TTA AAA AAA CAT      432
Asp Asn Leu Thr Asp Asp Asn Ala Gln Arg Ala Ile Leu Lys Lys His
130                 135                 140

GCA AAT AAA GAT AAG GGT GCT GCA GAA CTT GAA AAG TTA TTT AAA GCG      480
Ala Asn Lys Asp Lys Gly Ala Ala Glu Leu Glu Lys Leu Phe Lys Ala
145                 150                 155                 160

GTA GAA AAC TTA TCA AAA GCA GCT CAA GAC ACA TTA AAA AAT GCT GTT      528
Val Glu Asn Leu Ser Lys Ala Ala Gln Asp Thr Leu Lys Asn Ala Val
                165                 170                 175

AAA GAG CTT ACA AGT CCT ATT GTG GCA GAA AGT CCA AAA AAA CCT TAA      576
Lys Glu Leu Thr Ser Pro Ile Val Ala Glu Ser Pro Lys Lys Pro
            180                 185                 190
```

(2) INFORMATION FOR SEQ ID NO: 2:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 2:

```
Cys Asn Asn Ser Gly Lys Asp Gly Asn Ala Ser Ala Asn Ser Ala Asp
  1               5                  10                  15

Glu Ser Val Lys Gly Pro Asn Leu Thr Glu Ile Ser Lys Lys Ile Thr
                 20                  25                  30

Glu Ser Asn Ala Val Val Leu Ala Val Lys Glu Val Glu Thr Leu Leu
            35                  40                  45

Ala Ser Ile Asp Glu Leu Ala Thr Lys Ala Ile Gly Lys Lys Ile Gly
        50                  55                  60

Asn Asn Gly Leu Glu Ala Asn Gln Ser Lys Asn Thr Ser Leu Leu Ser
 65                  70                  75                  80

Gly Ala Tyr Ala Ile Ser Asp Leu Ile Ala Glu Lys Leu Asn Val Leu
                 85                  90                  95

Lys Asn Glu Glu Leu Lys Glu Lys Ile Asp Thr Ala Lys Gln Cys Ser
            100                 105                 110

Thr Glu Phe Thr Asn Lys Leu Lys Ser Glu His Ala Val Leu Gly Leu
        115                 120                 125

Asp Asn Leu Thr Asp Asp Asn Ala Gln Arg Ala Ile Leu Lys Lys His
130                 135                 140

Ala Asn Lys Asp Lys Gly Ala Ala Glu Leu Glu Lys Leu Phe Lys Ala
145                 150                 155                 160

Val Glu Asn Leu Ser Lys Ala Ala Gln Asp Thr Leu Lys Asn Ala Val
                165                 170                 175

Lys Glu Leu Thr Ser Pro Ile Val Ala Glu Ser Pro Lys Lys Pro
            180                 185                 190
```

(2) INFORMATION FOR SEQ ID NO: 3:

(i) SEQUENCE CHARACTERISTICS:
        (A) LENGTH: 585 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia burgdorfi
        (B) STRAIN: 2591

&nb (B) TYPE: amino acid
        (D) TOPOLOGY: linear (ii) MOLECULE TYPE: protein (xi) SEQUENCE DESCRIPTION: SEQ ID NO: 4:

Cys Asn Asn Ser Gly Lys Asp Gly Asn Thr Ser Ala Asn Ser Ala Asp
 1               5                  10                  15

Glu Ser Val Lys Gly Pro Asn Leu Thr Glu Ile Ser Lys Lys Ile Thr
            20                  25                  30

Glu Ser Asn Ala Val Leu Ala Val Lys Glu Val Glu Thr Leu Leu
        35                  40                  45

Ala Ser Ile Asp Glu Val Ala Lys Lys Ala Ile Gly Asn Leu Ile Ala
    50                  55                  60

Gln Asn Gly Leu Asn Ala Gly Ala Asn Gln Asn Gly Ser Leu Leu Ala
65                  70                  75                  80

Gly Ala Tyr Val Ile Ser Thr Leu Ile Ala Glu Lys Leu Asp Gly Leu
                85                  90                  95

Lys Asn Ser Glu Glu Leu Lys Glu Lys Ile Glu Asp Ala Lys Lys Cys
            100                 105                 110

Asn Lys Ala Phe Thr Asp Lys Leu Lys Ser Ser His Ala Glu Leu Gly
        115                 120                 125

Ile Ala Asn Gly Ala Ala Ser Asp Ala Asn Ala Lys Ala Ala Ile Leu
    130                 135                 140

Lys Thr Asn Gly Thr Lys Asp Lys Gly Ala Gln Glu Leu Glu Lys Leu
145                 150                 155                 160

Phe Glu Ser Val Lys Asn Leu Ser Lys Ala Ala Gln Glu Thr Leu Asn
                165                 170                 175

Asn Ser Val Lys Glu Leu Thr Ser Pro Val Val Ala Glu Asn Pro Lys
            180                 185                 190

Lys Pro (2) INFORMATION FOR SEQ ID NO: 5:

(i) SEQUENCE CHARACTERISTICS:
        (A) LENGTH: 579 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia burgdorferi
        (B) STRAIN: IP2

(ix) FEATURE:
        (A) NAME/KEY: CDS
        (B) LOCATION: 1..579

(xi) SEQUENCE DESCRIPTION: SEQ ID NO: 5:

```
TGT AAT AAT TCA GGG AAA GAT GGG AAT ACA TCT GCA AAT TCT GCT GAT        48
Cys Asn Asn Ser Gly Lys Asp Gly Asn Thr Ser Ala Asn Ser Ala Asp
 1               5                  10                  15

GAG TCT GTT AAA GGG CCT AAT CTT ACA GAA ATA AGT AAA AAA ATT ACG        96
Glu Ser Val Lys Gly Pro Asn Leu Thr Glu Ile Ser Lys Lys Ile Thr
            20                  25                  30

GAT TCT AAT GCG GTT TTA CTT GCT GTG AAA GAG GTT GAA GCG TTG CTG       144
Asp Ser Asn Ala Val Leu Leu Ala Val Lys Glu Val Glu Ala Leu Leu
        35                  40                  45

TCA TCT ATA GAT GAA ATT GCT GCT AAA GCT ATT GGT AAA AAA ATA CAC       192
```

```
Ser Ser Ile Asp Glu Ile Ala Ala Lys Ala Ile Gly Lys Lys Ile His
    50              55                  60

CAA AAT AAT GGT TTG GAT ACC GAA AAT AAT CAC AAT GGA TCA TTG TTA      240
Gln Asn Asn Gly Leu Asp Thr Glu Asn Asn His Asn Gly Ser Leu Leu
 65              70                  75                  80

GCG GGA GCT TAT GCA ATA TCA ACC CTA ATA AAA CAA AAA TTA GAT GGA      288
Ala Gly Ala Tyr Ala Ile Ser Thr Leu Ile Lys Gln Lys Leu Asp Gly
                 85                  90                  95

TTG AAA AAT GAA GGA TTA AAG GAA AAA ATT GAT GCG GCT AAG AAA TGT      336
Leu Lys Asn Glu Gly Leu Lys Glu Lys Ile Asp Ala Ala Lys Lys Cys
                100                 105                 110

TCT GAA ACA TTT ACT AAT AAA TTA AAA GAA AAA CAC ACA GAT CTT GGT      384
Ser Glu Thr Phe Thr Asn Lys Leu Lys Glu Lys His Thr Asp Leu Gly
            115                 120                 125

AAA GAA GGT GTT ACT GAT GCT GAT GCA AAA GAA GCC ATT TTA AAA ACA      432
Lys Glu Gly Val Thr Asp Ala Asp Ala Lys Glu Ala Ile Leu Lys Thr
        130                 135                 140

AAT GGT ACT AAA ACT AAA GGT GCT GAA GAA CTT GGA AAA TTA TTT GAA      480
Asn Gly Thr Lys Thr Lys Gly Ala Glu Glu Leu Gly Lys Leu Phe Glu
145                 150                 155                 160

TCA GTA GAG GTC TTG TCA AAA GCA GCT AAA GAG ATG CTT GCT AAT TCA      528
Ser Val Glu Val Leu Ser Lys Ala Ala Lys Glu Met Leu Ala Asn Ser
                165                 170                 175

GTT AAA GAG CTT ACA AGC CCT GTT GTG GCA GAA AGT CCA AAA AAA CCT      576
Val Lys Glu Leu Thr Ser Pro Val Val Ala Glu Ser Pro Lys Lys Pro
            180                 185                 190

TAA                                                                  579

(2) INFORMATION FOR SEQ ID NO: 6:

(i) SEQUENCE CHARACTERISTICS:
        (A) LENGTH: 192 amino acids
        (B) TYPE: amino acid
        (D) TOPOLOGY: linear (ii) MOLECULE TYPE: protein (xi) SEQUENCE DESCRIPTION: SEQ ID NO: 6:

Cys Asn Asn Ser Gly Lys Asp Gly Asn Thr Ser Ala Asn Ser Ala Asp
 1               5                  10                  15

Glu Ser Val Lys Gly Pro Asn Leu Thr Glu Ile Ser Lys Lys Ile Thr
                 20                  25                  30

Asp Ser Asn Ala Val Leu Leu Ala Val Lys Glu Val Glu Ala Leu Leu
             35                  40                  45

Ser Ser Ile Asp Glu Ile Ala Ala Lys Ala Ile Gly Lys Lys Ile His
    50                  55                  60

Gln Asn Asn Gly Leu Asp Thr Glu Asn Asn His Asn Gly Ser Leu Leu
 65              70                  75                  80

Ala Gly Ala Tyr Ala Ile Ser Thr Leu Ile Lys Gln Lys Leu Asp Gly
                 85                  90                  95

Leu Lys Asn Glu Gly Leu Lys Glu Lys Ile Asp Ala Ala Lys Lys Cys
                100                 105                 110

Ser Glu Thr Phe Thr Asn Lys Leu Lys Glu Lys His Thr Asp Leu Gly
            115                 120                 125

Lys Glu Gly Val Thr Asp Ala Asp Ala Lys Glu Ala Ile Leu Lys Thr
        130                 135                 140

Asn Gly Thr Lys Thr Lys Gly Ala Glu Glu Leu Gly Lys Leu Phe Glu
145                 150                 155                 160
```

```
Ser Val Glu Val Leu Ser Lys Ala Ala Lys Glu Met Leu Ala Asn Ser
            165                 170                 175

Val Lys Glu Leu Thr Ser Pro Val Val Ala Glu Ser Pro Lys Lys Pro
            180                 185                 190

(2) INFORMATION FOR SEQ ID NO: 7:

(i) SEQUENCE CHARACTERISTICS:
        (A) LENGTH: 531 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia burgdorferi
        (B) STRAIN: 25015

(ix) FEATURE:
        (A) NAME/KEY: CDS
        (B) LOCATION: 1..531

(xi) SEQUENCE DESCRIPTION: SEQ ID NO: 7:
```

| | | | | | | | | | | | | | | | | |
|---|---|---|---|---|---|---|---|---|---|---|---|---|---|---|---|---|
| TGT | AAT | AAT | TCA | GGA | AAA | GAT | GGG | AAC | GCT | GCA | TCT | ACT | AAT | CCT | GCT | 48 |
| Cys | Asn | Asn | Ser | Gly | Lys | Asp | Gly | Asn | Ala | Ala | Ser | Thr | Asn | Pro | Ala | |
| 1 | | | | 5 | | | | | 10 | | | | | 15 | | |
| GAT | GAG | TCT | GTT | AAA | GGG | CCT | AAT | CTT | ACA | GAA | ATA | AGT | AAA | AAA | ATT | 96 |
| Asp | Glu | Ser | Val | Lys | Gly | Pro | Asn | Leu | Thr | Glu | Ile | Ser | Lys | Lys | Ile | |
| | | | 20 | | | | | 25 | | | | | 30 | | | |
| ACA | GAT | TCT | AAT | ACG | GTT | GTG | CTA | GCT | GTA | AAA | GAA | GTT | GAA | GCT | TTG | 144 |
| Thr | Asp | Ser | Asn | Thr | Val | Val | Leu | Ala | Val | Lys | Glu | Val | Glu | Ala | Leu | |
| | | 35 | | | | | 40 | | | | | 45 | | | | |
| CTT | ACA | TCT | ATA | GAT | GAA | CTT | GCT | ACT | AAA | GCT | ATT | GGT | AAA | AAA | ATA | 192 |
| Leu | Thr | Ser | Ile | Asp | Glu | Leu | Ala | Thr | Lys | Ala | Ile | Gly | Lys | Lys | Ile | |
| | 50 | | | | | 55 | | | | | 60 | | | | | |
| CAC | CAA | AAT | AAT | GGT | TTG | GAT | ACC | GAA | AAT | AAT | CAC | AAT | GGA | TCA | TTG | 240 |
| His | Gln | Asn | Asn | Gly | Leu | Asp | Thr | Glu | Asn | Asn | His | Asn | Gly | Ser | Leu | |
| 65 | | | | | 70 | | | | | 75 | | | | | 80 | |
| TTA | GCG | GGG | GCC | TAT | GCA | ATA | TCA | ACG | CTA | ATA | ACA | CAA | AAG | TTA | GGT | 288 |
| Leu | Ala | Gly | Ala | Tyr | Ala | Ile | Ser | Thr | Leu | Ile | Thr | Gln | Lys | Leu | Gly | |
| | | | | 85 | | | | | 90 | | | | | 95 | | |
| GGA | TTG | AAA | AAT | GAA | GAA | TTA | AAG | GAA | AAG | ATT | GCC | GCA | GTC | AAG | AAA | 336 |
| Gly | Leu | Lys | Asn | Glu | Glu | Leu | Lys | Glu | Lys | Ile | Ala | Ala | Val | Lys | Lys | |
| | | | 100 | | | | | 105 | | | | | 110 | | | |
| TGT | TCT | GAA | GAA | TTT | ACT | AAT | AAA | CTA | AAA | AGT | AGT | CAC | ACA | GAG | CTC | 384 |
| Cys | Ser | Glu | Glu | Phe | Thr | Asn | Lys | Leu | Lys | Ser | Ser | His | Thr | Glu | Leu | |
| | | 115 | | | | | 120 | | | | | 125 | | | | |
| GGC | AAA | CAG | GAT | GCT | CAG | GAT | GAT | GAT | GCA | AAA | AAG | GCT | ATC | TTA | AGA | 432 |
| Gly | Lys | Gln | Asp | Ala | Gln | Asp | Asp | Asp | Ala | Lys | Lys | Ala | Ile | Leu | Arg | |
| | 130 | | | | | 135 | | | | | 140 | | | | | |
| ACA | CAT | AAT | ACT | AAG | GAT | AAG | GGT | GCT | GAA | GAA | CTT | GAT | AAG | TTA | TTT | 480 |
| Thr | His | Asn | Thr | Lys | Asp | Lys | Gly | Ala | Glu | Glu | Leu | Asp | Lys | Leu | Phe | |
| 145 | | | | | 150 | | | | | 155 | | | | | 160 | |
| AAA | CCG | GTG | GAG | AAC | TTG | TCA | AAA | GCT | GCT | AAA | GAG | ATG | CTA | TCC | AAT | 528 |
| Lys | Pro | Val | Glu | Asn | Leu | Ser | Lys | Ala | Ala | Lys | Glu | Met | Leu | Ser | Asn | |
| | | | | 165 | | | | | 170 | | | | | 175 | | |
| TCA | | | | | | | | | | | | | | | | 531 |
| Ser | | | | | | | | | | | | | | | | |

```
(2) INFORMATION FOR SEQ ID NO: 8:

(i) SEQUENCE CHARACTERISTICS:
        (A) LENGTH: 177 amino acids
```

```
            (B) TYPE: amino acid
            (D) TOPOLOGY: linear (ii) MOLECULE TYPE: protein (xi) SEQUENCE DESCRIPTION: SEQ ID NO: 8:

Cys Asn Asn Ser Gly Lys Asp Gly Asn Ala Ala Ser Thr Asn Pro Ala
 1               5                  10                  15

Asp Glu Ser Val Lys Gly Pro Asn Leu Thr Glu Ile Ser Lys Lys Ile
             20                  25                  30

Thr Asp Ser Asn Thr Val Val Leu Ala Val Lys Glu Val Glu Ala Leu
         35                  40                  45

Leu Thr Ser Ile Asp Glu Leu Ala Thr Lys Ala Ile Gly Lys Lys Ile
     50                  55                  60

His Gln Asn Asn Gly Leu Asp Thr Glu Asn Asn His Asn Gly Ser Leu
 65                  70                  75                  80

Leu Ala Gly Ala Tyr Ala Ile Ser Thr Leu Ile Thr Gln Lys Leu Gly
                 85                  90                  95

Gly Leu Lys Asn Glu Glu Leu Lys Glu Lys Ile Ala Ala Val Lys Lys
            100                 105                 110

Cys Ser Glu Glu Phe Thr Asn Lys Leu Lys Ser Ser His Thr Glu Leu
        115                 120                 125

Gly Lys Gln Asp Ala Gln Asp Asp Ala Lys Lys Ala Ile Leu Arg
    130                 135                 140

Thr His Asn Thr Lys Asp Lys Gly Ala Glu Glu Leu Asp Lys Leu Phe
145                 150                 155                 160

Lys Pro Val Glu Asn Leu Ser Lys Ala Ala Lys Glu Met Leu Ser Asn
                165                 170                 175

Ser (2) INFORMATION FOR SEQ ID NO: 9:

(i) SEQUENCE CHARACTERISTICS:
            (A) LENGTH: 582 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Borrelia burgdorferi
            (B) STRAIN: ZS7

(ix) FEATURE:
            (A) NAME/KEY: CDS
            (B) LOCATION: 1..582

(xi) SEQUENCE DESCRIPTION: SEQ ID NO: 9:

TGT AAT AAT TCA GGA AAA GAT GGG AAT ACA TCT GCA AAT TCT GCT GAT      48
Cys Asn Asn Ser Gly Lys Asp Gly Asn Thr Ser Ala Asn Ser Ala Asp
 1               5                  10                  15

GAG TCT GTT AAA GGG CCT AAT CTT ACA GAA ATA AGT AAA AAA ATT ACG      96
Glu Ser Val Lys Gly Pro Asn Leu Thr Glu Ile Ser Lys Lys Ile Thr
             20                  25                  30

GAT TCT AAT GCG GTT TTA CTT GCT GTG AAA GAG GTT GAA GCG TTG CTG     144
Asp Ser Asn Ala Val Leu Leu Ala Val Lys Glu Val Glu Ala Leu Leu
         35                  40                  45

TCA TCT ATA GAT GAG CTT GCT AAA GCT ATT GGT AAA AAA ATA AAA AAC     192
Ser Ser Ile Asp Glu Leu Ala Lys Ala Ile Gly Lys Lys Ile Lys Asn
     50                  55                  60
```

```
GAT GGT AGT TTA GGT GAT GAA GCA AAT CAC AAC GAG TCA TTG TTA GCA      240
Asp Gly Ser Leu Gly Asp Glu Ala Asn His Asn Glu Ser Leu Leu Ala
65              70                  75                  80

GGA GCT TAT ACA ATA TCA ACC TTA ATA ACA CAA AAA TTA AGT AAA TTA      288
Gly Ala Tyr Thr Ile Ser Thr Leu Ile Thr Gln Lys Leu Ser Lys Leu
                85                  90                  95

AAC GGA TCA GAA GGT TTA AAG GAA AAG ATT GCC GCA GCT AAG AAA TGC      336
Asn Gly Ser Glu Gly Leu Lys Glu Lys Ile Ala Ala Ala Lys Lys Cys
            100                 105                 110

TCT GAA GAG TTT AGT ACT AAA CTA AAA GAT AAT CAT GCA CAG CTT GGT      384
Ser Glu Glu Phe Ser Thr Lys Leu Lys Asp Asn His Ala Gln Leu Gly
        115                 120                 125

ATA CAG GGC GTT ACT GAT GAA AAT GCA AAA AAA GCT ATT TTA AAA GCA      432
Ile Gln Gly Val Thr Asp Glu Asn Ala Lys Lys Ala Ile Leu Lys Ala
130                 135                 140

AAT GCA GCG GGT AAA GAT AAG GGC GTT GAA GAA CTT GAA AAG TTG TCC      480
Asn Ala Ala Gly Lys Asp Lys Gly Val Glu Glu Leu Glu Lys Leu Ser
145                 150                 155                 160

GGA TCA TTA GAA AGC TTA TCA AAA GCA GCT AAA GAG ATG CTT GCT AAT      528
Gly Ser Leu Glu Ser Leu Ser Lys Ala Ala Lys Glu Met Leu Ala Asn
                165                 170                 175

TCA GTT AAA GAG CTT ACA AGT CCT GTT GTG GTA GAA AGT CCA AAA AAA      576
Ser Val Lys Glu Leu Thr Ser Pro Val Val Val Glu Ser Pro Lys Lys
            180                 185                 190

CCT TAA                                                              582
Pro (2) INFORMATION FOR SEQ ID NO: 10:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 10:

Cys Asn Asn Ser Gly Lys Asp Gly Asn Thr Ser Ala Asn Ser Ala Asp
1               5                   10                  15

Glu Ser Val Lys Gly Pro Asn Leu Thr Glu Ile Ser Lys Lys Ile Thr
                20                  25                  30

Asp Ser Asn Ala Val Leu Leu Ala Val Lys Glu Val Glu Ala Leu Leu
            35                  40                  45

Ser Ser Ile Asp Glu Leu Ala Lys Ala Ile Gly Lys Lys Ile Lys Asn
        50                  55                  60

Asp Gly Ser Leu Gly Asp Glu Ala Asn His Asn Glu Ser Leu Leu Ala
65              70                  75                  80

Gly Ala Tyr Thr Ile Ser Thr Leu Ile Thr Gln Lys Leu Ser Lys Leu
                85                  90                  95

Asn Gly Ser Glu Gly Leu Lys Glu Lys Ile Ala Ala Ala Lys Lys Cys
            100                 105                 110

Ser Glu Glu Phe Ser Thr Lys Leu Lys Asp Asn His Ala Gln Leu Gly
        115                 120                 125

Ile Gln Gly Val Thr Asp Glu Asn Ala Lys Lys Ala Ile Leu Lys Ala
130                 135                 140

Asn Ala Ala Gly Lys Asp Lys Gly Val Glu Glu Leu Glu Lys Leu Ser
145                 150                 155                 160

Gly Ser Leu Glu Ser Leu Ser Lys Ala Ala Lys Glu Met Leu Ala Asn
                165                 170                 175
```

```
Ser Val Lys Glu Leu Thr Ser Pro Val Val Glu Ser Pro Lys Lys
            180                 185                 190
Pro
```

(2) INFORMATION FOR SEQ ID NO: 11:

(i) SEQUENCE CHARACTERISTICS:
        (A) LENGTH: 579 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia burgdorferi
        (B) STRAIN: 297

(ix) FEATURE:
        (A) NAME/KEY: CDS
        (B) LOCATION: 1..579

(xi) SEQUENCE DESCRIPTION: SEQ ID NO: 11:

```
TGT AAT AAT TCA GGG AAA GAT GGG AAT ACA TCT GCA AAT TCT GCT GAT      48
Cys Asn Asn Ser Gly Lys Asp Gly Asn Thr Ser Ala Asn Ser Ala Asp
  1               5                  10                  15

GAG TCT GTT AAA GGG CCT AAT CTT ACA GAA ATA AGT AAA AAA ATT ACA      96
Glu Ser Val Lys Gly Pro Asn Leu Thr Glu Ile Ser Lys Lys Ile Thr
             20                  25                  30

GAA TCT AAC GCA GTT GTT CTC GCC GTG AAA GAA GTT GAA ACT TTG CTT     144
Glu Ser Asn Ala Val Val Leu Ala Val Lys Glu Val Glu Thr Leu Leu
         35                  40                  45

ACA TCT ATA GAT GAG CTT GCT AAA GCT ATT GGT AAA AAA ATA AAA AAC     192
Thr Ser Ile Asp Glu Leu Ala Lys Ala Ile Gly Lys Lys Ile Lys Asn
     50                  55                  60

GAT GTT AGT TTA GAT AAT GAG GCA GAT CAC AAC GGA TCA TTA ATA TCA     240
Asp Val Ser Leu Asp Asn Glu Ala Asp His Asn Gly Ser Leu Ile Ser
 65                  70                  75                  80

GGA GCA TAT TTA ATT TCA ACA TTA ATA ACA AAA AAA ATA AGT GCA ATA     288
Gly Ala Tyr Leu Ile Ser Thr Leu Ile Thr Lys Lys Ile Ser Ala Ile
                 85                  90                  95

AAA GAT TCA GGA GAA TTG AAG GCA GAA ATT GAA AAG GCT AAG AAA TGT     336
Lys Asp Ser Gly Glu Leu Lys Ala Glu Ile Glu Lys Ala Lys Lys Cys
            100                 105                 110

TCT GAA GAA TTT ACT GCT AAA TTA AAA GGT GAA CAC ACA GAT CTT GGT     384
Ser Glu Glu Phe Thr Ala Lys Leu Lys Gly Glu His Thr Asp Leu Gly
        115                 120                 125

AAA GAA GGC GTT ACT GAT GAT AAT GCA AAA AAA GCC ATT TTA AAA ACA     432
Lys Glu Gly Val Thr Asp Asp Asn Ala Lys Lys Ala Ile Leu Lys Thr
    130                 135                 140

AAT AAT GAT AAA ACT AAG GGC GCT GAT GAA CTT GAA AAG TTA TTT GAA     480
Asn Asn Asp Lys Thr Lys Gly Ala Asp Glu Leu Glu Lys Leu Phe Glu
145                 150                 155                 160

TCA GTA AAA AAC TTG TCA AAA GCA GCT AAA GAG ATG CTT ACT AAT TCA     528
Ser Val Lys Asn Leu Ser Lys Ala Ala Lys Glu Met Leu Thr Asn Ser
                165                 170                 175

GTT AAA GAG CTT ACA AGC CCT GTT GTG GCA GAA AGT CCA AAA AAA CCT     576
Val Lys Glu Leu Thr Ser Pro Val Val Ala Glu Ser Pro Lys Lys Pro
            180                 185                 190

TAA                                                                  579
```

(2) INFORMATION FOR SEQ ID NO: 12:

(i) SEQUENCE CHARACTERISTICS:
        (A) LENGTH: 192 amino acids
        (B) TYPE: amino acid
        (D) TOPOLOGY: linear (ii) MOLECULE TYPE: protein (xi) SEQUENCE DESCRIPTION: SEQ ID NO: 12:

Cys Asn Asn Ser Gly Lys Asp Gly Asn Thr Ser Ala Asn Ser Ala Asp
 1               5                  10                  15

Glu Ser Val Lys Gly Pro Asn Leu Thr Glu Ile Ser Lys Lys Ile Thr
            20                  25                  30

Glu Ser Asn Ala Val Val Leu Ala Val Lys Glu Val Glu Thr Leu Leu
        35                  40                  45

Thr Ser Ile Asp Glu Leu Ala Lys Ala Ile Gly Lys Lys Ile Lys Asn
    50                  55                  60

Asp Val Ser Leu Asp Asn Glu Ala Asp His Asn Gly Ser Leu Ile Ser
65                  70                  75                  80

Gly Ala Tyr Leu Ile Ser Thr Leu Ile Thr Lys Lys Ile Ser Ala Ile
                85                  90                  95

Lys Asp Ser Gly Glu Leu Lys Ala Glu Ile Glu Lys Ala Lys Lys Cys
            100                 105                 110

Ser Glu Glu Phe Thr Ala Lys Leu Lys Gly Glu His Thr Asp Leu Gly
        115                 120                 125

Lys Glu Gly Val Thr Asp Asp Asn Ala Lys Lys Ala Ile Leu Lys Thr
    130                 135                 140

Asn Asn Asp Lys Thr Lys Gly Ala Asp Glu Leu Glu Lys Leu Phe Glu
145                 150                 155                 160

Ser Val Lys Asn Leu Ser Lys Ala Ala Lys Glu Met Leu Thr Asn Ser
                165                 170                 175

Val Lys Glu Leu Thr Ser Pro Val Val Ala Glu Ser Pro Lys Lys Pro
            180                 185                 190

(2) INFORMATION FOR SEQ ID NO: 13:

(i) SEQUENCE CHARACTERISTICS:
        (A) LENGTH: 534 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia afzelii
        (B) STRAIN: SIMON (ix) FEATURE:
        (A) NAME/KEY: CDS
        (B) LOCATION: 1..534

(xi) SEQUENCE DESCRIPTION: SEQ ID NO: 13:

TGT AAT AAT TCA GGA AAA GGT GGG GAT TCT ACA TCT ACT AAT CCT GCT      48
Cys Asn Asn Ser Gly Lys Gly Gly Asp Ser Thr Ser Thr Asn Pro Ala
 1               5                  10                  15

GAC GAG TCT GCT AAA GGG CCT AAT CTT ACA GAA ATA AGT AAA AAA ATT      96
Asp Glu Ser Ala Lys Gly Pro Asn Leu Thr Glu Ile Ser Lys Lys Ile
            20                  25                  30

ACA AAT TCT AAT GCA TTT GTA CTT GCT GTT AAA GAA GTT GAG ACT TTG     144
Thr Asn Ser Asn Ala Phe Val Leu Ala Val Lys Glu Val Glu Thr Leu
        35                  40                  45

-continued

```
GTT GCA TCT ATA GAT GAA CTT GCT ACT AAA GCT ATT GGT AAA AAA ATA        192
Val Ala Ser Ile Asp Glu Leu Ala Thr Lys Ala Ile Gly Lys Lys Ile
 50                  55                  60

AAA AAT GAT GGC ACT TTA GAG AAC GAA GCA AAT CAC AAC GGA TCA TTG        240
Lys Asn Asp Gly Thr Leu Glu Asn Glu Ala Asn His Asn Gly Ser Leu
 65                  70                  75                  80

TTA GCG GGA GCT TAT GCA ATA TCA AAT CTA ATA AAA CAA AAA TTA GAT        288
Leu Ala Gly Ala Tyr Ala Ile Ser Asn Leu Ile Lys Gln Lys Leu Asp
                     85                  90                  95

GGA TTG AAA GGT TTA GAA GGA TTA AAT AAG GAA ATT GCG GAG GCC AAG        336
Gly Leu Lys Gly Leu Glu Gly Leu Asn Lys Glu Ile Ala Glu Ala Lys
                100                 105                 110

AAC TGT TCT GAA GCA TTT ACT AAA AAA CTA AAA GAG AAG CAC ACA GAT        384
Asn Cys Ser Glu Ala Phe Thr Lys Lys Leu Lys Glu Lys His Thr Asp
        115                 120                 125

CTT GGG AAA GAG AAT GCT ACC GAT GAA GAT GCA AAA AAA GCT ATT TTA        432
Leu Gly Lys Glu Asn Ala Thr Asp Glu Asp Ala Lys Lys Ala Ile Leu
130                 135                 140

AAA ACA GAT GCT ACT AAA GAT AAG GGT GCT GCT GAA CTT GAA AAG CTA        480
Lys Thr Asp Ala Thr Lys Asp Lys Gly Ala Ala Glu Leu Glu Lys Leu
145                 150                 155                 160

TCT GAA TCA GTA GCA AGC TTA GTA AAA GCG GCT CAA GAA GCA CTA ACT        528
Ser Glu Ser Val Ala Ser Leu Val Lys Ala Ala Gln Glu Ala Leu Thr
                165                 170                 175

AAT TCA                                                                534
Asn Ser
```

(2) INFORMATION FOR SEQ ID NO: 14:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO: 14:

```
Cys Asn Ser Gly Lys Gly Gly Asp Ser Thr Ser Thr Asn Pro Ala
  1               5                  10                  15

Asp Glu Ser Ala Lys Gly Pro Asn Leu Thr Glu Ile Ser Lys Lys Ile
                 20                  25                  30

Thr Asn Ser Asn Ala Phe Val Leu Ala Val Lys Glu Val Glu Thr Leu
                 35                  40                  45

Val Ala Ser Ile Asp Glu Leu Ala Thr Lys Ala Ile Gly Lys Lys Ile
 50                  55                  60

Lys Asn Asp Gly Thr Leu Glu Asn Glu Ala Asn His Asn Gly Ser Leu
 65                  70                  75                  80

Leu Ala Gly Ala Tyr Ala Ile Ser Asn Leu Ile Lys Gln Lys Leu Asp
                     85                  90                  95

Gly Leu Lys Gly Leu Glu Gly Leu Asn Lys Glu Ile Ala Glu Ala Lys
                100                 105                 110

Asn Cys Ser Glu Ala Phe Thr Lys Lys Leu Lys Glu Lys His Thr Asp
        115                 120                 125

Leu Gly Lys Glu Asn Ala Thr Asp Glu Asp Ala Lys Lys Ala Ile Leu
130                 135                 140

Lys Thr Asp Ala Thr Lys Asp Lys Gly Ala Ala Glu Leu Glu Lys Leu
145                 150                 155                 160

Ser Glu Ser Val Ala Ser Leu Val Lys Ala Ala Gln Glu Ala Leu Thr
                165                 170                 175
```

Asn Ser (2) INFORMATION FOR SEQ ID NO: 15:

(i) SEQUENCE CHARACTERISTICS:
        (A) LENGTH: 582 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia afzelii
        (B) STRAIN: E61

(ix) FEATURE:
        (A) NAME/KEY: CDS
        (B) LOCATION: 1..582

(xi) SEQUENCE DESCRIPTION: SEQ ID NO: 15:

```
TGT AAT AAT TCA GGG AAA GGT GGG GAT TCT ACA TCT ACT AAT CCT GCT      48
Cys Asn Asn Ser Gly Lys Gly Gly Asp Ser Thr Ser Thr Asn Pro Ala
 1               5                  10                  15

GAC GAG TCT GCT AAA GGG CCT AAT CTT ACA GAA ATA AGT AAA AAA ATT      96
Asp Glu Ser Ala Lys Gly Pro Asn Leu Thr Glu Ile Ser Lys Lys Ile
                20                  25                  30

ACA GAT TCT AAT GCA TTT GTA CTT GCT GTT AAA GAA GTT GAG ACT TTG     144
Thr Asp Ser Asn Ala Phe Val Leu Ala Val Lys Glu Val Glu Thr Leu
             35                  40                  45

GTT GCA TCT ATA GAT GAA CTT GCT ACT AAA GCT ATT GGT AAA AAA ATA     192
Val Ala Ser Ile Asp Glu Leu Ala Thr Lys Ala Ile Gly Lys Lys Ile
     50                  55                  60

AAA AAT GAT GGC ACT TTA GAT AAC GAA GCA AAT CAC AAC GGA TCA TTG     240
Lys Asn Asp Gly Thr Leu Asp Asn Glu Ala Asn His Asn Gly Ser Leu
 65                  70                  75                  80

TTA GCA GGA GCC TAT GCA ATA TCA ACT CTA ATA ACA CAA AAA TTA AGT     288
Leu Ala Gly Ala Tyr Ala Ile Ser Thr Leu Ile Thr Gln Lys Leu Ser
                 85                  90                  95

GTA TTG AAT TCA GAA GAA TTA AAG GCA GAA ATT GTA AAG GCT AAG AAA     336
Val Leu Asn Ser Glu Glu Leu Lys Ala Glu Ile Val Lys Ala Lys Lys
                100                 105                 110

TGT TCC GAA GAC TTT ACT AAA AAA CTA AAA GAT AAG CAC ACA GAA CTT     384
Cys Ser Glu Asp Phe Thr Lys Lys Leu Lys Asp Lys His Thr Glu Leu
             115                 120                 125

GGT AAA CAG GAT GCT AAT GAT GAT GAT GCA AAA AAA GCT ATT TTA AAA     432
Gly Lys Gln Asp Ala Asn Asp Asp Asp Ala Lys Lys Ala Ile Leu Lys
 130                 135                 140

ACA AAT GGC GAT AAA ACT TTG GGT GCT GCT GAA CTT GAA AAG CTA TCT     480
Thr Asn Gly Asp Lys Thr Leu Gly Ala Ala Glu Leu Glu Lys Leu Ser
145                 150                 155                 160

GAA TCA GTA ACA AGC TTG TCA AAA GCA GCT AAA GAA TCA CTA ACC AAT     528
Glu Ser Val Thr Ser Leu Ser Lys Ala Ala Lys Glu Ser Leu Thr Asn
                 165                 170                 175

TCA GTT AAA GAG CTT ACA AGT CCT GTT GTA GCA GAA ACT CCA AAA AAA     576
Ser Val Lys Glu Leu Thr Ser Pro Val Val Ala Glu Thr Pro Lys Lys
                 180                 185                 190

CCT TAA                                                             582
Pro
```

(2) INFORMATION FOR SEQ ID NO: 16:

(i) SEQUENCE CHARACTERISTICS:

(A) LENGTH: 193 amino acids
(B) TYPE: amino acid
(D) TOPOLOGY: linear (ii) MOLECULE TYPE: protein (xi) SEQUENCE DESCRIPTION: SEQ ID NO: 16:

```
Cys Asn Asn Ser Gly Lys Gly Gly Asp Ser Thr Ser Thr Asn Pro Ala
  1               5                  10                  15

Asp Glu Ser Ala Lys Gly Pro Asn Leu Thr Glu Ile Ser Lys Lys Ile
             20                  25                  30

Thr Asp Ser Asn Ala Phe Val Leu Ala Val Lys Glu Val Glu Thr Leu
         35                  40                  45

Val Ala Ser Ile Asp Glu Leu Ala Thr Lys Ala Ile Gly Lys Lys Ile
     50                  55                  60

Lys Asn Asp Gly Thr Leu Asp Asn Glu Ala Asn His Asn Gly Ser Leu
 65                  70                  75                  80

Leu Ala Gly Ala Tyr Ala Ile Ser Thr Leu Ile Thr Gln Lys Leu Ser
                 85                  90                  95

Val Leu Asn Ser Glu Glu Leu Lys Ala Glu Ile Val Lys Ala Lys Lys
            100                 105                 110

Cys Ser Glu Asp Phe Thr Lys Lys Leu Lys Asp Lys His Thr Glu Leu
        115                 120                 125

Gly Lys Gln Asp Ala Asn Asp Asp Ala Lys Lys Ala Ile Leu Lys
    130                 135                 140

Thr Asn Gly Asp Lys Thr Leu Gly Ala Ala Glu Leu Glu Lys Leu Ser
145                 150                 155                 160

Glu Ser Val Thr Ser Leu Ser Lys Ala Ala Lys Glu Ser Leu Thr Asn
                165                 170                 175

Ser Val Lys Glu Leu Thr Ser Pro Val Val Ala Glu Thr Pro Lys Lys
            180                 185                 190

Pro
```

(2) INFORMATION FOR SEQ ID NO: 17:

(i) SEQUENCE CHARACTERISTICS:
(A) LENGTH: 585 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Borrelia afzelii
(B) STRAIN: ORTH (ix) FEATURE:
(A) NAME/KEY: CDS
(B) LOCATION: 1..585

(xi) SEQUENCE DESCRIPTION: SEQ ID NO: 17:

```
TGT AAT AAT TCA GGG AAA GGT GGA GAT TCT GCA TCT ACT AAT CCT GCT      48
Cys Asn Asn Ser Gly Lys Gly Gly Asp Ser Ala Ser Thr Asn Pro Ala
  1               5                  10                  15

GAC GAG TCT GCG AAA GGA CCT AAT CTT ACA GAA ATA AGC AAA AAA ATT      96
Asp Glu Ser Ala Lys Gly Pro Asn Leu Thr Glu Ile Ser Lys Lys Ile
             20                  25                  30

ACA GAT TCT AAT GCA TTT GTA CTG GCT GTT AAA GAA GTT GAG ACT TTG    144
Thr Asp Ser Asn Ala Phe Val Leu Ala Val Lys Glu Val Glu Thr Leu
         35                  40                  45
```

```
GTT TCA TCT ATA GAT GAA CTT GCT ACT AAA GCT ATT GGT AAA AAA ATA      192
Val Ser Ser Ile Asp Glu Leu Ala Thr Lys Ala Ile Gly Lys Lys Ile
     50              55                  60

CAA CAA AAT AAT GGT TTA GGC GCC AAT GCG GAT AAA AAC GGA TCA TTG      240
Gln Gln Asn Asn Gly Leu Gly Ala Asn Ala Asp Lys Asn Gly Ser Leu
 65              70                  75                  80

TTA GCA GGA GCT TAT GCA ATA TCA ACC CTA ATA ACA GAA AAA TTA AAG      288
Leu Ala Gly Ala Tyr Ala Ile Ser Thr Leu Ile Thr Glu Lys Leu Lys
                 85                  90                  95

GCA TTG AAA AAT TCA GGA GAA TTA AAG GCA AAA ATT GAA GAT GCT AAG      336
Ala Leu Lys Asn Ser Gly Glu Leu Lys Ala Lys Ile Glu Asp Ala Lys
             100                 105                 110

AAA TGT TCT GAA GAT TTT ACT AAA AAA CTA GCT GCT GGG CAT GCA CAG      384
Lys Cys Ser Glu Asp Phe Thr Lys Lys Leu Ala Ala Gly His Ala Gln
         115                 120                 125

CTT GGT ATA GAC GGA GCT ACT GAT AAT GAT TCA AAA GAA GCA ATT TTG      432
Leu Gly Ile Asp Gly Ala Thr Asp Asn Asp Ser Lys Glu Ala Ile Leu
130                 135                 140

AAA ACA AAT GGG ACT AAA ACT AAG GGT GCT GAA GAA CTT GTA AAG TTA      480
Lys Thr Asn Gly Thr Lys Thr Lys Gly Ala Glu Glu Leu Val Lys Leu
145                 150                 155                 160

TCT GAA TCA GTA GCA AGC TTG TCA AAA GCG GCT CAA GAA GCA TCA GCT      528
Ser Glu Ser Val Ala Ser Leu Ser Lys Ala Ala Gln Glu Ala Ser Ala
                 165                 170                 175

AAT TCA GTT AAA GAG CTT ACA AGT CCT GTT GTA GCA GAA ACT CCA AAA      576
Asn Ser Val Lys Glu Leu Thr Ser Pro Val Val Ala Glu Thr Pro Lys
             180                 185                 190

AAA CCT TAA                                                          585
Lys Pro
    195
```

(2) INFORMATION FOR SEQ ID NO: 18:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO: 18:

```
Cys Asn Asn Ser Gly Lys Gly Gly Asp Ser Ala Ser Thr Asn Pro Ala
 1               5                  10                  15

Asp Glu Ser Ala Lys Gly Pro Asn Leu Thr Glu Ile Ser Lys Lys Ile
             20                  25                  30

Thr Asp Ser Asn Ala Phe Val Leu Ala Val Lys Glu Val Glu Thr Leu
         35                  40                  45

Val Ser Ser Ile Asp Glu Leu Ala Thr Lys Ala Ile Gly Lys Lys Ile
     50              55                  60

Gln Gln Asn Asn Gly Leu Gly Ala Asn Ala Asp Lys Asn Gly Ser Leu
 65              70                  75                  80

Leu Ala Gly Ala Tyr Ala Ile Ser Thr Leu Ile Thr Glu Lys Leu Lys
                 85                  90                  95

Ala Leu Lys Asn Ser Gly Glu Leu Lys Ala Lys Ile Glu Asp Ala Lys
             100                 105                 110

Lys Cys Ser Glu Asp Phe Thr Lys Lys Leu Ala Ala Gly His Ala Gln
         115                 120                 125

Leu Gly Ile Asp Gly Ala Thr Asp Asn Asp Ser Lys Glu Ala Ile Leu
130                 135                 140
```

-continued

```
Lys Thr Asn Gly Thr Lys Thr Lys Gly Ala Glu Glu Leu Val Lys Leu
145                 150                 155                 160

Ser Glu Ser Val Ala Ser Leu Ser Lys Ala Ala Gln Glu Ala Ser Ala
                165                 170                 175

Asn Ser Val Lys Glu Leu Thr Ser Pro Val Val Ala Glu Thr Pro Lys
            180                 185                 190

Lys Pro
```

(2) INFORMATION FOR SEQ ID NO: 19:

(i) SEQUENCE CHARACTERISTICS:
        (A) LENGTH: 582 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia afzelii
        (B) STRAIN: ACA1

(ix) FEATURE:
        (A) NAME/KEY: CDS
        (B) LOCATION: 1..582

(xi) SEQUENCE DESCRIPTION: SEQ ID NO: 19:

```
TGT AAT AAT TCA GGG AAA GGT GGG GAT TCT GCA TCT ACT AAT CCT GCT      48
Cys Asn Asn Ser Gly Lys Gly Gly Asp Ser Ala Ser Thr Asn Pro Ala
 1               5                  10                  15

GAC GAG TCT GCG AAA GGG CCT AAT CTT ACA GAA ATA AGC AAA AAA ATT      96
Asp Glu Ser Ala Lys Gly Pro Asn Leu Thr Glu Ile Ser Lys Lys Ile
             20                  25                  30

ACA GAT TCT AAT GCA TTT GTA CTT GCT GTT AAA GAA GTT GAG ACT TTG     144
Thr Asp Ser Asn Ala Phe Val Leu Ala Val Lys Glu Val Glu Thr Leu
         35                  40                  45

GTT TCA TCT ATA GAT GAA CTT GCC AAT AAA GCT ATT GGT AAA AAA ATA     192
Val Ser Ser Ile Asp Glu Leu Ala Asn Lys Ala Ile Gly Lys Lys Ile
     50                  55                  60

CAA CAA AAT GGT TTA GGC GCC GAA GCG AAT CGC AAC GAA TCA TTG TTA     240
Gln Gln Asn Gly Leu Gly Ala Glu Ala Asn Arg Asn Glu Ser Leu Leu
 65                  70                  75                  80

GCA GGA GTT CAT GAA ATA TCA ACA CTA ATA ACA GAA AAA TTA AGT AAA     288
Ala Gly Val His Glu Ile Ser Thr Leu Ile Thr Glu Lys Leu Ser Lys
                 85                  90                  95

TTG AAA AAT TCA GGA GAA TTA AAG GCA AAA ATT GAA GAT GCT AAG AAA     336
Leu Lys Asn Ser Gly Glu Leu Lys Ala Lys Ile Glu Asp Ala Lys Lys
            100                 105                 110

TGT TCT GAA GAA TTT ACT AAT AAA CTA AGA GTT AGT CAT GCA GAT CTT     384
Cys Ser Glu Glu Phe Thr Asn Lys Leu Arg Val Ser His Ala Asp Leu
        115                 120                 125

GGT AAA CAA GGT GTT AAT GAC GAT GAT GCA AAA AAA GCT ATT TTA AAA     432
Gly Lys Gln Gly Val Asn Asp Asp Asp Ala Lys Lys Ala Ile Leu Lys
    130                 135                 140

ACA AAT GCA GAT AAA ACT AAA GGT GCT GAA GAA CTT GGA AAG TTA TTT     480
Thr Asn Ala Asp Lys Thr Lys Gly Ala Glu Glu Leu Gly Lys Leu Phe
145                 150                 155                 160

AAA TCA GTG GAA GGT TTG GTA AAA GCA GCT CAA GAA GCA CTA ACT AAT     528
Lys Ser Val Glu Gly Leu Val Lys Ala Ala Gln Glu Ala Leu Thr Asn
                165                 170                 175

TCA GTT AAA GAG CTT ACA AGT CCT GTT GTA GCA GAA AGT CCA AAA AAA     576
Ser Val Lys Glu Leu Thr Ser Pro Val Val Ala Glu Ser Pro Lys Lys
            180                 185                 190
```

CCT TAA                                                                          582
Pro (2) INFORMATION FOR SEQ ID NO: 20:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 20:

Cys Asn Asn Ser Gly Lys Gly Gly Asp Ser Ala Ser Thr Asn Pro Ala
 1               5                  10                  15

Asp Glu Ser Ala Lys Gly Pro Asn Leu Thr Glu Ile Ser Lys Lys Ile
             20                  25                  30

Thr Asp Ser Asn Ala Phe Val Leu Ala Val Lys Glu Val Glu Thr Leu
         35                  40                  45

Val Ser Ser Ile Asp Glu Leu Ala Asn Lys Ala Ile Gly Lys Lys Ile
     50                  55                  60

Gln Gln Asn Gly Leu Gly Ala Glu Ala Asn Arg Asn Glu Ser Leu Leu
 65                  70                  75                  80

Ala Gly Val His Glu Ile Ser Thr Leu Ile Thr Glu Lys Leu Ser Lys
                 85                  90                  95

Leu Lys Asn Ser Gly Glu Leu Lys Ala Lys Ile Glu Asp Ala Lys Lys
                100                 105                 110

Cys Ser Glu Glu Phe Thr Asn Lys Leu Arg Val Ser His Ala Asp Leu
            115                 120                 125

Gly Lys Gln Gly Val Asn Asp Asp Ala Lys Lys Ala Ile Leu Lys
        130                 135                 140

Thr Asn Ala Asp Lys Thr Lys Gly Ala Glu Glu Leu Gly Lys Leu Phe
145                 150                 155                 160

Lys Ser Val Glu Gly Leu Val Lys Ala Ala Gln Glu Ala Leu Thr Asn
                165                 170                 175

Ser Val Lys Glu Leu Thr Ser Pro Val Val Ala Glu Ser Pro Lys Lys
            180                 185                 190

Pro (2) INFORMATION FOR SEQ ID NO: 21:

(i) SEQUENCE CHARACTERISTICS:
        (A) LENGTH: 585 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia afzelii
        (B) STRAIN: H9

(ix) FEATURE:
        (A) NAME/KEY: CDS
        (B) LOCATION: 1..585

(xi) SEQUENCE DESCRIPTION: SEQ ID NO: 21:

TGT AAT AAT TCA GGG AAA GGT GGA GAT TCT GCA TCT ACT AAT CCT GCT      48
Cys Asn Asn Ser Gly Lys Gly Gly Asp Ser Ala Ser Thr Asn Pro Ala
 1               5                  10                  15

```
GAC GAG TCT GCG AAA GGG CCT AAT CTT ACA GAA ATA AGC AAA AAA ATT        96
Asp Glu Ser Ala Lys Gly Pro Asn Leu Thr Glu Ile Ser Lys Lys Ile
            20                  25                  30

ACA GAT TCT AAT GCA TTT GTA CTT GCT GTT AAA GAA GTT GAG ACT TTG       144
Thr Asp Ser Asn Ala Phe Val Leu Ala Val Lys Glu Val Glu Thr Leu
        35                  40                  45

GTT TCA TCT ATA GAT GAA CTT GCT GCT CAA GCT ATT GGT AAA AAA ATA       192
Val Ser Ser Ile Asp Glu Leu Ala Ala Gln Ala Ile Gly Lys Lys Ile
    50                  55                  60

CAA AAC AAT GGT TTG ACT GCC GAA CAG AAT CAA AAC GGA TCA TTG TTG       240
Gln Asn Asn Gly Leu Thr Ala Glu Gln Asn Gln Asn Gly Ser Leu Leu
65                  70                  75                  80

GCC GGA GCC TAT GCA ATA TCA GCC CTA ATA ACA AAA AAA TTA GAT GAA       288
Ala Gly Ala Tyr Ala Ile Ser Ala Leu Ile Thr Lys Lys Leu Asp Glu
                85                  90                  95

TTG ACC AAA AAT TCA GGA GAA TTA AAA GGA GAA GTT GAA AAA GCT AAG       336
Leu Thr Lys Asn Ser Gly Glu Leu Lys Gly Glu Val Glu Lys Ala Lys
            100                 105                 110

AAA TGT TCC GAA GAA TTT ACT AAT AAA CTA AAA GGT GGT CAT GCA GAG       384
Lys Cys Ser Glu Glu Phe Thr Asn Lys Leu Lys Gly Gly His Ala Glu
        115                 120                 125

CTT GGA CTT GCT GCT GCT ACT GAT GAA AAT GCA AAA AAA GCC ATT TTA       432
Leu Gly Leu Ala Ala Ala Thr Asp Glu Asn Ala Lys Lys Ala Ile Leu
    130                 135                 140

AAA ACA AAT GGA ACT AAA GAT AAG GGG GCT GAA GAA CTT GAA AAG TTA       480
Lys Thr Asn Gly Thr Lys Asp Lys Gly Ala Glu Glu Leu Glu Lys Leu
145                 150                 155                 160

TTT AAA TCA GTA GAA AGC TTG GCA AAA GCA GCT AAA GAA TCA CTA ACC       528
Phe Lys Ser Val Glu Ser Leu Ala Lys Ala Ala Lys Glu Ser Leu Thr
                165                 170                 175

AAT TCA GTT AAA GAG CTT ACA AAC CCT GTT GTA GCA GAA AGT CCA AAA       576
Asn Ser Val Lys Glu Leu Thr Asn Pro Val Val Ala Glu Ser Pro Lys
            180                 185                 190

AAA CCT TAA                                                           585
Lys Pro
    195

(2) INFORMATION FOR SEQ ID NO: 22:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO: 22:

Cys Asn Asn Ser Gly Lys Gly Gly Asp Ser Ala Ser Thr Asn Pro Ala
1               5                   10                  15

Asp Glu Ser Ala Lys Gly Pro Asn Leu Thr Glu Ile Ser Lys Lys Ile
            20                  25                  30

Thr Asp Ser Asn Ala Phe Val Leu Ala Val Lys Glu Val Glu Thr Leu
        35                  40                  45

Val Ser Ser Ile Asp Glu Leu Ala Ala Gln Ala Ile Gly Lys Lys Ile
    50                  55                  60

Gln Asn Asn Gly Leu Thr Ala Glu Gln Asn Gln Asn Gly Ser Leu Leu
65                  70                  75                  80

Ala Gly Ala Tyr Ala Ile Ser Ala Leu Ile Thr Lys Lys Leu Asp Glu
                85                  90                  95

Leu Thr Lys Asn Ser Gly Glu Leu Lys Gly Glu Val Glu Lys Ala Lys
```

```
              100                 105                 110
Lys Cys Ser Glu Glu Phe Thr Asn Lys Leu Lys Gly Gly His Ala Glu
        115                 120                 125

Leu Gly Leu Ala Ala Ala Thr Asp Glu Asn Ala Lys Lys Ala Ile Leu
        130                 135                 140

Lys Thr Asn Gly Thr Lys Asp Lys Gly Ala Glu Glu Leu Glu Lys Leu
145                 150                 155                 160

Phe Lys Ser Val Glu Ser Leu Ala Lys Ala Ala Lys Glu Ser Leu Thr
                165                 170                 175

Asn Ser Val Lys Glu Leu Thr Asn Pro Val Val Ala Glu Ser Pro Lys
                180                 185                 190

Lys Pro (2) INFORMATION FOR SEQ ID NO: 23:

(i) SEQUENCE CHARACTERISTICS:
        (A) LENGTH: 531 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia afzelii
        (B) STRAIN: J1

(ix) FEATURE:
        (A) NAME/KEY: CDS
        (B) LOCATION: 1..531

(xi) SEQUENCE DESCRIPTION: SEQ ID NO: 23:

TGT AAT AAT TCA GGG AAA GGT GGG GAT TCT GCA TCT ACT AAT CCT ACT      48
Cys Asn Asn Ser Gly Lys Gly Gly Asp Ser Ala Ser Thr Asn Pro Thr
  1               5                  10                  15

GAC GAG TCT GCG AAA GGG CCT AAT CTT ACA GAA ATA AGC AAA AAA ATT      96
Asp Glu Ser Ala Lys Gly Pro Asn Leu Thr Glu Ile Ser Lys Lys Ile
             20                  25                  30

ACA GAT TCT AAT GCA TTT GTA CTT GCT GTT AAA GAA GTT GAG ACT TTG     144
Thr Asp Ser Asn Ala Phe Val Leu Ala Val Lys Glu Val Glu Thr Leu
         35                  40                  45

GTT TCT TCT ATA GAT GAA CTT GCT AAT AAA GCT ATT GGT CAA AAA ATA     192
Val Ser Ser Ile Asp Glu Leu Ala Asn Lys Ala Ile Gly Gln Lys Ile
     50                  55                  60

CAA AAC AAT GGT TTG AGT GCC GAA CAG AAT CAA AAC GGA TCA TTA TTA     240
Gln Asn Asn Gly Leu Ser Ala Glu Gln Asn Gln Asn Gly Ser Leu Leu
 65                  70                  75                  80

GCA GGA GCC TAT GCA ATA TCA ACC CTA ATA AAA CAA AAA CTA GAT GGA     288
Ala Gly Ala Tyr Ala Ile Ser Thr Leu Ile Lys Gln Lys Leu Asp Gly
                 85                  90                  95

TTA AAA GGT CTA GAA GGA TTA AAT AAA GAA ATT ACA GAG GCC AAA AAA     336
Leu Lys Gly Leu Glu Gly Leu Asn Lys Glu Ile Thr Glu Ala Lys Lys
            100                 105                 110

TGT TCT CAA GAC TTT ATC AAT AAA CTA AAA GGT GGT CAT GCA GAG CTT     384
Cys Ser Gln Asp Phe Ile Asn Lys Leu Lys Gly Gly His Ala Glu Leu
        115                 120                 125

GGA CTT GTT GCT GCT ACT GAT GCT AAT GCA AAA GCA GCC ATT TTA AAA     432
Gly Leu Val Ala Ala Thr Asp Ala Asn Ala Lys Ala Ala Ile Leu Lys
        130                 135                 140

ACA AAT GGC GAT AAA ACT AAA GGG GCT GAC GAA TTT GAA AAG CTA TTT     480
Thr Asn Gly Asp Lys Thr Lys Gly Ala Asp Glu Phe Glu Lys Leu Phe
145                 150                 155                 160
```

| | | | | | | | | | | | | | | |
|---|---|---|---|---|---|---|---|---|---|---|---|---|---|---|
| AAA | TCA | GTA | GAA | GGT | TTG | TTA | AAA | GCA | GCT | CAA | GAA | GCA | CTA | ACT | AAT | 528
| Lys | Ser | Val | Glu | Gly | Leu | Leu | Lys | Ala | Ala | Gln | Glu | Ala | Leu | Thr | Asn |
| | | | 165 | | | | 170 | | | | | 175 | | | |

TCA　　　　　　　　　　　　　　　　　　　　　　　　531
Ser (2) INFORMATION FOR SEQ ID NO: 24:

(i) SEQUENCE CHARACTERISTICS:
        (A) LENGTH: 177 amino acids
        (B) TYPE: amino acid
        (D) TOPOLOGY: linear (ii) MOLECULE TYPE: protein (xi) SEQUENCE DESCRIPTION: SEQ ID NO: 24:

Cys Asn Asn Ser Gly Lys Gly Gly Asp Ser Ala Ser Thr Asn Pro Thr
1               5                  10                 15

Asp Glu Ser Ala Lys Gly Pro Asn Leu Thr Glu Ile Ser Lys Lys Ile
            20                  25                  30

Thr Asp Ser Asn Ala Phe Val Leu Ala Val Lys Glu Val Glu Thr Leu
        35                  40                  45

Val Ser Ser Ile Asp Glu Leu Ala Asn Lys Ala Ile Gly Gln Lys Ile
    50                  55                  60

Gln Asn Asn Gly Leu Ser Ala Glu Gln Asn Gln Asn Gly Ser Leu Leu
65                  70                  75                  80

Ala Gly Ala Tyr Ala Ile Ser Thr Leu Ile Lys Gln Lys Leu Asp Gly
                85                  90                  95

Leu Lys Gly Leu Glu Gly Leu Asn Lys Glu Ile Thr Glu Ala Lys Lys
            100                 105                 110

Cys Ser Gln Asp Phe Ile Asn Lys Leu Lys Gly Gly His Ala Glu Leu
        115                 120                 125

Gly Leu Val Ala Ala Thr Asp Ala Asn Ala Lys Ala Ala Ile Leu Lys
    130                 135                 140

Thr Asn Gly Asp Lys Thr Lys Gly Ala Asp Glu Phe Glu Lys Leu Phe
145                 150                 155                 160

Lys Ser Val Glu Gly Leu Leu Lys Ala Ala Gln Glu Ala Leu Thr Asn
                165                 170                 175

Ser (2) INFORMATION FOR SEQ ID NO: 25:

(i) SEQUENCE CHARACTERISTICS:
        (A) LENGTH: 585 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia afzelii
        (B) STRAIN: JSB (ix) FEATURE:
        (A) NAME/KEY: CDS
        (B) LOCATION: 1..585

(xi) SEQUENCE DESCRIPTION: SEQ ID NO: 25:

| | | | | | | | | | | | | | | |
|---|---|---|---|---|---|---|---|---|---|---|---|---|---|---|---|
| TGT | AAT | AAT | TCA | GGG | AAA | GGT | GGG | GAT | TCT | GCA | TCT | ACT | AAT | CCT | GCT | 48
| Cys | Asn | Asn | Ser | Gly | Lys | Gly | Gly | Asp | Ser | Ala | Ser | Thr | Asn | Pro | Ala |
| 1 | | | | 5 | | | | | 10 | | | | | 15 | |

```
GAC GAG TCT GCG AAA GGG CCT AAT CTT ACA GAA ATA AGC AAA AAA ATT      96
Asp Glu Ser Ala Lys Gly Pro Asn Leu Thr Glu Ile Ser Lys Lys Ile
             20                  25                  30

ACA GAT TCT AAT GCA TTT GTA CTT GCT GTT AAA GAA GTT GAG ACT TTG     144
Thr Asp Ser Asn Ala Phe Val Leu Ala Val Lys Glu Val Glu Thr Leu
         35                  40                  45

GTT TTA TCT ATA GAT GAA CTT GCT AAG AAA GCT ATT GGT CAA AAA ATA     192
Val Leu Ser Ile Asp Glu Leu Ala Lys Lys Ala Ile Gly Gln Lys Ile
     50                  55                  60

GAC AAT AAT AAT GGT TTA GCT GCT TTA AAT AAT CAG AAT GGA TCG TTG     240
Asp Asn Asn Asn Gly Leu Ala Ala Leu Asn Asn Gln Asn Gly Ser Leu
 65                  70                  75                  80

TTA GCA GGA GCC TAT GCA ATA TCA ACC CTA ATA ACA GAA AAA TTG AGT     288
Leu Ala Gly Ala Tyr Ala Ile Ser Thr Leu Ile Thr Glu Lys Leu Ser
                 85                  90                  95

AAA TTG AAA AAT TTA GAA GAA TTA AAG ACA GAA ATT GCA AAG GCT AAG     336
Lys Leu Lys Asn Leu Glu Glu Leu Lys Thr Glu Ile Ala Lys Ala Lys
             100                 105                 110

AAA TGT TCC GAA GAA TTT ACT AAT AAA CTA AAA AGT GGT CAT GCA GAT     384
Lys Cys Ser Glu Glu Phe Thr Asn Lys Leu Lys Ser Gly His Ala Asp
         115                 120                 125

CTT GGC AAA CAG GAT GCT ACC GAT GAT CAT GCA AAA GCA GCT ATT TTA     432
Leu Gly Lys Gln Asp Ala Thr Asp Asp His Ala Lys Ala Ala Ile Leu
     130                 135                 140

AAA ACA CAT GCA ACT ACC GAT AAA GGT GCT AAA GAA TTT AAA GAT TTA     480
Lys Thr His Ala Thr Thr Asp Lys Gly Ala Lys Glu Phe Lys Asp Leu
145                 150                 155                 160

TTT GAA TCA GTA GAA GGT TTG TTA AAA GCA GCT CAA GTA GCA CTA ACT     528
Phe Glu Ser Val Glu Gly Leu Leu Lys Ala Ala Gln Val Ala Leu Thr
                 165                 170                 175

AAT TCA GTT AAA GAA CTT ACA AGT CCT GTT GTA GCA GAA AGT CCA AAA     576
Asn Ser Val Lys Glu Leu Thr Ser Pro Val Val Ala Glu Ser Pro Lys
             180                 185                 190

AAA CCT TAA                                                          585
Lys Pro
        195
```

(2) INFORMATION FOR SEQ ID NO: 26:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO: 26:

```
Cys Asn Asn Ser Gly Lys Gly Gly Asp Ser Ala Ser Thr Asn Pro Ala
  1               5                  10                  15

Asp Glu Ser Ala Lys Gly Pro Asn Leu Thr Glu Ile Ser Lys Lys Ile
             20                  25                  30

Thr Asp Ser Asn Ala Phe Val Leu Ala Val Lys Glu Val Glu Thr Leu
         35                  40                  45

Val Leu Ser Ile Asp Glu Leu Ala Lys Lys Ala Ile Gly Gln Lys Ile
     50                  55                  60

Asp Asn Asn Asn Gly Leu Ala Ala Leu Asn Asn Gln Asn Gly Ser Leu
 65                  70                  75                  80

Leu Ala Gly Ala Tyr Ala Ile Ser Thr Leu Ile Thr Glu Lys Leu Ser
                 85                  90                  95
```

```
Lys Leu Lys Asn Leu Glu Glu Leu Lys Thr Glu Ile Ala Lys Ala Lys
            100                 105                 110

Lys Cys Ser Glu Glu Phe Thr Asn Lys Leu Lys Ser Gly His Ala Asp
            115                 120                 125

Leu Gly Lys Gln Asp Ala Thr Asp His Ala Lys Ala Ala Ile Leu
            130                 135                 140

Lys Thr His Ala Thr Thr Asp Lys Gly Ala Lys Glu Phe Lys Asp Leu
145                 150                 155                 160

Phe Glu Ser Val Glu Gly Leu Leu Lys Ala Ala Gln Val Ala Leu Thr
                165                 170                 175

Asn Ser Val Lys Glu Leu Thr Ser Pro Val Val Ala Glu Ser Pro Lys
            180                 185                 190

Lys Pro (2) INFORMATION FOR SEQ ID NO: 27:

(i) SEQUENCE CHARACTERISTICS:
        (A) LENGTH: 576 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Borrelia afzelii
         (B) STRAIN: VS461

(ix) FEATURE:
         (A) NAME/KEY: CDS
         (B) LOCATION: 1..576

(xi) SEQUENCE DESCRIPTION: SEQ ID NO: 27:

TGT AAT AAT TCA GGG AAA GGT GGG GAT ATT GCA TCT ACT AAT CCT GAT       48
Cys Asn Asn Ser Gly Lys Gly Gly Asp Ile Ala Ser Thr Asn Pro Asp
 1               5                  10                  15

GAG TCT GCG AAA GGA CCT AAT CTT ACA GAA ATA AGC AAA AAA ATT ACA       96
Glu Ser Ala Lys Gly Pro Asn Leu Thr Glu Ile Ser Lys Lys Ile Thr
                20                  25                  30

GAT TCC AAT GCA GTT GTA CTA GCT GTG AAA GAA GTT GAG GCT TTG CTT      144
Asp Ser Asn Ala Val Val Leu Ala Val Lys Glu Val Glu Ala Leu Leu
            35                  40                  45

TCA TCT ATA GAT GAA CTT GCT AAA ACT ATT GGT AAA AAA ATA GAG GCA      192
Ser Ser Ile Asp Glu Leu Ala Lys Thr Ile Gly Lys Lys Ile Glu Ala
        50                  55                  60

AAT GGT TTG GGT AAC GAA GCG GAT AAA AAC GGA TCA TTA TTA GCA GGA      240
Asn Gly Leu Gly Asn Glu Ala Asp Lys Asn Gly Ser Leu Leu Ala Gly
65                  70                  75                  80

GCC TAT GCA ATA TCA ACC CTA ATA AAA CAA AAA TTA GAT GGA TTG AAA      288
Ala Tyr Ala Ile Ser Thr Leu Ile Lys Gln Lys Leu Asp Gly Leu Lys
                85                  90                  95

GGT CTA GAA GGA TTA AAT AAA GAA ATT GCG GAG GCC AAG AAA TGT TCC      336
Gly Leu Glu Gly Leu Asn Lys Glu Ile Ala Glu Ala Lys Lys Cys Ser
            100                 105                 110

GAA GCA TTT ACT AAA AAG CTA CAA GAT AGT AAC GCA GAT CTT GGA AAA      384
Glu Ala Phe Thr Lys Lys Leu Gln Asp Ser Asn Ala Asp Leu Gly Lys
        115                 120                 125

CAT AAT GCT ACT GAT GCT GAT TCA AAA GAA GCA ATT TTG AAA ACA AAT      432
His Asn Ala Thr Asp Ala Asp Ser Lys Glu Ala Ile Leu Lys Thr Asn
130                 135                 140

GGG ACT AAA ACT AAG GGT GCT AAA GAA CTT GAA GAG TTG TTT AAA TCA      480
Gly Thr Lys Thr Lys Gly Ala Lys Glu Leu Glu Glu Leu Phe Lys Ser
```

```
                145                 150                 155                 160
GTA GAA AGC TTG TCA AAA GCA GCT AAA GAA GCA TTA AGT AAT TCA GTT          528
Val Glu Ser Leu Ser Lys Ala Ala Lys Glu Ala Leu Ser Asn Ser Val
                165                 170                 175

AAA GAG CTT ACA AGC CCT GTT GTA GCA GAA AGT CCA AAA AAA CCT TAA          576
Lys Glu Leu Thr Ser Pro Val Val Ala Glu Ser Pro Lys Lys Pro
        180                 185                 190
```

(2) INFORMATION FOR SEQ ID NO: 28:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 28:

```
Cys Asn Asn Ser Gly Lys Gly Gly Asp Ile Ala Ser Thr Asn Pro Asp
 1               5                  10                  15

Glu Ser Ala Lys Gly Pro Asn Leu Thr Glu Ile Ser Lys Lys Ile Thr
             20                  25                  30

Asp Ser Asn Ala Val Val Leu Ala Val Lys Glu Val Glu Ala Leu Leu
         35                  40                  45

Ser Ser Ile Asp Glu Leu Ala Lys Thr Ile Gly Lys Lys Ile Glu Ala
 50                  55                  60

Asn Gly Leu Gly Asn Glu Ala Asp Lys Asn Gly Ser Leu Leu Ala Gly
 65                  70                  75                  80

Ala Tyr Ala Ile Ser Thr Leu Ile Lys Gln Lys Leu Asp Gly Leu Lys
             85                  90                  95

Gly Leu Glu Gly Leu Asn Lys Glu Ile Ala Glu Ala Lys Lys Cys Ser
            100                 105                 110

Glu Ala Phe Thr Lys Lys Leu Gln Asp Ser Asn Ala Asp Leu Gly Lys
        115                 120                 125

His Asn Ala Thr Asp Ala Asp Ser Lys Glu Ala Ile Leu Lys Thr Asn
130                 135                 140

Gly Thr Lys Thr Lys Gly Ala Lys Glu Leu Glu Glu Leu Phe Lys Ser
145                 150                 155                 160

Val Glu Ser Leu Ser Lys Ala Ala Lys Glu Ala Leu Ser Asn Ser Val
            165                 170                 175

Lys Glu Leu Thr Ser Pro Val Val Ala Glu Ser Pro Lys Lys Pro
        180                 185                 190
```

(2) INFORMATION FOR SEQ ID NO: 29:

(i) SEQUENCE CHARACTERISTICS:
        (A) LENGTH: 576 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: M57

(ix) FEATURE:
        (A) NAME/KEY: CDS
        (B) LOCATION: 1..576

(xi) SEQUENCE DESCRIPTION: SEQ ID NO: 29:

| | |
|---|---|
|TGT AAT AAT TCA GGT GGG GAT ACC GCA TCT ACT AAT CCT GAT GAG TCT<br>Cys Asn Asn Ser Gly Gly Asp Thr Ala Ser Thr Asn Pro Asp Glu Ser<br>1               5                      10                      15 | 48 |
|GCA AAA GGA CCT AAT CTT ACA GTA ATA AGC AAA AAA ATT ACA GAT TCT<br>Ala Lys Gly Pro Asn Leu Thr Val Ile Ser Lys Lys Ile Thr Asp Ser<br>                20                      25                      30 | 96 |
|AAT GCA TTT GTA CTG GCT GTG AAA GAA GTT GAG GCT TTG ATC TCA TCT<br>Asn Ala Phe Val Leu Ala Val Lys Glu Val Glu Ala Leu Ile Ser Ser<br>        35                      40                      45 | 144 |
|ATA GAT GAA CTT GCT AAT AAA GCT ATT GGT AAA GTA ATA CAT CAA AAT<br>Ile Asp Glu Leu Ala Asn Lys Ala Ile Gly Lys Val Ile His Gln Asn<br>50                      55                      60 | 192 |
|AAT GGT TTA AAT GCT AAT GCG GGT CAA AAC GGA TCA TTG TTA GCA GGA<br>Asn Gly Leu Asn Ala Asn Ala Gly Gln Asn Gly Ser Leu Leu Ala Gly<br>65                      70                      75                      80 | 240 |
|GCC TAT GCA ATA TCA ACC CTA ATA ACA GAA AAA TTA AGT AAA TTG AAA<br>Ala Tyr Ala Ile Ser Thr Leu Ile Thr Glu Lys Leu Ser Lys Leu Lys<br>                85                      90                      95 | 288 |
|AAT TCA GAA GAG TTA AAT AAA AAA ATT GAA GAG GCT AAG AAC CAT TCT<br>Asn Ser Glu Glu Leu Asn Lys Lys Ile Glu Glu Ala Lys Asn His Ser<br>        100                     105                     110 | 336 |
|GAA GCA TTT ACT AAT AGA CTA AAA GGT TCT CAT GCA CAA CTT GGA GTT<br>Glu Ala Phe Thr Asn Arg Leu Lys Gly Ser His Ala Gln Leu Gly Val<br>        115                     120                     125 | 384 |
|GCT GCT GCT ACT GAT GAT CAT GCA AAA GAA GCT ATT TTA AAG TCA AAT<br>Ala Ala Ala Thr Asp Asp His Ala Lys Glu Ala Ile Leu Lys Ser Asn<br>130                     135                     140 | 432 |
|CCT ACT AAA GAT AAG GGT GCT AAA GAA CTT AAA GAC TTA TCT GAA TCA<br>Pro Thr Lys Asp Lys Gly Ala Lys Glu Leu Lys Asp Leu Ser Glu Ser<br>145                     150                     155                     160 | 480 |
|GTA GAA AGC TTG GCA AAA GCA GCG CAA GAA GCA TTA GCT AAT TCA GTT<br>Val Glu Ser Leu Ala Lys Ala Ala Gln Glu Ala Leu Ala Asn Ser Val<br>                165                     170                     175 | 528 |
|AAA GAG CTT ACA AGT CCT GTT GTG GCA GAA ACT CCA AAA AAA CCT TAA<br>Lys Glu Leu Thr Ser Pro Val Val Ala Glu Thr Pro Lys Lys Pro<br>        180                     185                     190 | 576 |

(2) INFORMATION FOR SEQ ID NO: 30:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 30:

```
Cys Asn Asn Ser Gly Gly Asp Thr Ala Ser Thr Asn Pro Asp Glu Ser
1               5                      10                      15

Ala Lys Gly Pro Asn Leu Thr Val Ile Ser Lys Lys Ile Thr Asp Ser
                20                      25                      30

Asn Ala Phe Val Leu Ala Val Lys Glu Val Glu Ala Leu Ile Ser Ser
        35                      40                      45

Ile Asp Glu Leu Ala Asn Lys Ala Ile Gly Lys Val Ile His Gln Asn
50                      55                      60

Asn Gly Leu Asn Ala Asn Ala Gly Gln Asn Gly Ser Leu Leu Ala Gly
65                      70                      75                      80

Ala Tyr Ala Ile Ser Thr Leu Ile Thr Glu Lys Leu Ser Lys Leu Lys
                85                      90                      95

Asn Ser Glu Glu Leu Asn Lys Lys Ile Glu Glu Ala Lys Asn His Ser
```

```
                100               105                110
Glu Ala Phe Thr Asn Arg Leu Lys Gly Ser His Ala Gln Leu Gly Val
        115                 120                 125

Ala Ala Ala Thr Asp Asp His Ala Lys Glu Ala Ile Leu Lys Ser Asn
130                 135                 140

Pro Thr Lys Asp Lys Gly Ala Lys Glu Leu Lys Asp Leu Ser Glu Ser
145                 150                 155                 160

Val Glu Ser Leu Ala Lys Ala Gln Glu Ala Leu Ala Asn Ser Val
                165                 170                 175

Lys Glu Leu Thr Ser Pro Val Val Ala Glu Thr Pro Lys Lys Pro
        180                 185                 190
```

(2) INFORMATION FOR SEQ ID NO: 31:

(i) SEQUENCE CHARACTERISTICS:
        (A) LENGTH: 579 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: W (ix) FEATURE:
        (A) NAME/KEY: CDS
        (B) LOCATION: 1..579

(xi) SEQUENCE DESCRIPTION: SEQ ID NO: 31:

```
TGT AAT AAT TCA GGT GGG GAT ACT GCA TCT ACT AAT CCT GAT GAG TCT      48
Cys Asn Asn Ser Gly Gly Asp Thr Ala Ser Thr Asn Pro Asp Glu Ser
1               5                   10                  15

GCG AAA GGA CCT AAT CTT ATA GAA ATA AGC AAA AAA ATT ACA GAT TCT      96
Ala Lys Gly Pro Asn Leu Ile Glu Ile Ser Lys Lys Ile Thr Asp Ser
            20                  25                  30

AAT GCA TTT GTA CTG GCT GTG AAA GAA GTT GAG GCT TTG ATC TCA TCT     144
Asn Ala Phe Val Leu Ala Val Lys Glu Val Glu Ala Leu Ile Ser Ser
        35                  40                  45

ATA GAT GAA CTT GCT AAT AAA GCT ATT GGT AAA AAA ATA AAT CAA AAT     192
Ile Asp Glu Leu Ala Asn Lys Ala Ile Gly Lys Lys Ile Asn Gln Asn
50                  55                  60

GGT TTA GAT GCT GAT GCT AAT CAC AAC GGA TCA TTG TTA GCA GGA GCC     240
Gly Leu Asp Ala Asp Ala Asn His Asn Gly Ser Leu Leu Ala Gly Ala
65                  70                  75                  80

CAT GCA ATA TCA ACT CTA ATA AAA CAA AAA ACA GAT GGA TTG AAA GAT     288
His Ala Ile Ser Thr Leu Ile Lys Gln Lys Thr Asp Gly Leu Lys Asp
            85                  90                  95

CTA GAA GGG TTA AGT AAA GAA ATT GCA AAG GTG AAG GAA TGT TCC GAT     336
Leu Glu Gly Leu Ser Lys Glu Ile Ala Lys Val Lys Glu Cys Ser Asp
        100                 105                 110

AAA TTT ACT AAA AAG CTA ACA GAT AGT CAT GCA CAG CTT GGA GCA GTT     384
Lys Phe Thr Lys Lys Leu Thr Asp Ser His Ala Gln Leu Gly Ala Val
115                 120                 125

GGT GGT GCT ATT AAT GAT GAT CGT GCA AAA GAA GCT ATT TTA AAA ACA     432
Gly Gly Ala Ile Asn Asp Asp Arg Ala Lys Glu Ala Ile Leu Lys Thr
            130                 135                 140

CAT GGG ACT AAC GAT AAG GGT GCT AAA GAA CTT AAA GAG TTA TCT GAA     480
His Gly Thr Asn Asp Lys Gly Ala Lys Glu Leu Lys Glu Leu Ser Glu
145                 150                 155                 160

TCA GTA GAA AGC TTG GCA AAA GCA GCT CAA GCA GCA TTA GCT AAT TCA     528
```

```
Ser Val Glu Ser Leu Ala Lys Ala Ala Gln Ala Ala Leu Ala Asn Ser
            165                 170                 175

GTT AAA GAG CTT ACA AGT CCT GTT GTG GCA GAA ACT CCA AAA AAA CCT        576
Val Lys Glu Leu Thr Ser Pro Val Val Ala Glu Thr Pro Lys Lys Pro
            180                 185                 190

TAA                                                                    579
```

(2) INFORMATION FOR SEQ ID NO: 32:

(i) SEQUENCE CHARACTERISTICS:
        (A) LENGTH: 192 amino acids
        (B) TYPE: amino acid
        (D) TOPOLOGY: linear (ii) MOLECULE TYPE: protein (xi) SEQUENCE DESCRIPTION: SEQ ID NO: 32:

```
Cys Asn Asn Ser Gly Gly Asp Thr Ala Ser Thr Asn Pro Asp Glu Ser
 1               5                  10                  15

Ala Lys Gly Pro Asn Leu Ile Glu Ile Ser Lys Lys Ile Thr Asp Ser
            20                  25                  30

Asn Ala Phe Val Leu Ala Val Lys Glu Val Glu Ala Leu Ile Ser Ser
            35                  40                  45

Ile Asp Glu Leu Ala Asn Lys Ala Ile Gly Lys Lys Ile Asn Gln Asn
 50                  55                  60

Gly Leu Asp Ala Asp Ala Asn His Asn Gly Ser Leu Leu Ala Gly Ala
 65                  70                  75                  80

His Ala Ile Ser Thr Leu Ile Lys Gln Lys Thr Asp Gly Leu Lys Asp
            85                  90                  95

Leu Glu Gly Leu Ser Lys Glu Ile Ala Lys Val Lys Glu Cys Ser Asp
            100                 105                 110

Lys Phe Thr Lys Lys Leu Thr Asp Ser His Ala Gln Leu Gly Ala Val
            115                 120                 125

Gly Gly Ala Ile Asn Asp Asp Arg Ala Lys Glu Ala Ile Leu Lys Thr
            130                 135                 140

His Gly Thr Asn Asp Lys Gly Ala Lys Glu Leu Lys Glu Leu Ser Glu
145                 150                 155                 160

Ser Val Glu Ser Leu Ala Lys Ala Ala Gln Ala Ala Leu Ala Asn Ser
            165                 170                 175

Val Lys Glu Leu Thr Ser Pro Val Val Ala Glu Thr Pro Lys Lys Pro
            180                 185                 190
```

(2) INFORMATION FOR SEQ ID NO: 33:

(i) SEQUENCE CHARACTERISTICS:
        (A) LENGTH: 573 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: VSDA (ix) FEATURE:
        (A) NAME/KEY: CDS
        (B) LOCATION: 1..573

(xi) SEQUENCE DESCRIPTION: SEQ ID NO: 33:

```
TGT AAT AAT TCA GGT GGG GAT ACT GCA TCT ACT AAT CCT GAT GAA TCT        48
```

```
Cys Asn Asn Ser Gly Gly Asp Thr Ala Ser Thr Asn Pro Asp Glu Ser
 1               5                  10                  15

GCG AAA GGA CCT GAT CTT ACA GTA ATA AGC AAA AAA ATT ACA GAT TCT    96
Ala Lys Gly Pro Asp Leu Thr Val Ile Ser Lys Lys Ile Thr Asp Ser
            20                  25                  30

AAT GCA TTT GTA CTG GCT GTG AAA GAA GTT GAA GCT TTG CTT TCA TCT   144
Asn Ala Phe Val Leu Ala Val Lys Glu Val Glu Ala Leu Leu Ser Ser
        35                  40                  45

GTA GAT GAA CTT GCC AAA GCT ATT GGT AAA AAG ATA CAT CAA AAT AAT   192
Val Asp Glu Leu Ala Lys Ala Ile Gly Lys Lys Ile His Gln Asn Asn
 50                  55                  60

GGT TTA GAT ACT CTG TCA AAT CAA AAC GGA TCA TTG TTA GCA GGA GCC   240
Gly Leu Asp Thr Leu Ser Asn Gln Asn Gly Ser Leu Leu Ala Gly Ala
 65                  70                  75                  80

TAT GCA ATA TCA ACC CTA ATA ACA AAA AAA TTA GAT GGA TTG AAA GGT   288
Tyr Ala Ile Ser Thr Leu Ile Thr Lys Lys Leu Asp Gly Leu Lys Gly
                 85                  90                  95

TCA GAA GGA TTA AAA GCA GAA ATT GCA GAA GCT AAG AAA TGT TCT GAA   336
Ser Glu Gly Leu Lys Ala Glu Ile Ala Glu Ala Lys Lys Cys Ser Glu
            100                 105                 110

GAC TTT ACT AAA AAA CTA AAA GAG AAG CAT ACA GAA CTT GGA GTT GCT   384
Asp Phe Thr Lys Lys Leu Lys Glu Lys His Thr Glu Leu Gly Val Ala
        115                 120                 125

GCT GCT ACT GAT GAT AAT GCA AAA AAA GCT ATT TTA AAA GCA AAT GGG   432
Ala Ala Thr Asp Asp Asn Ala Lys Lys Ala Ile Leu Lys Ala Asn Gly
 130                 135                 140

GAT AAG ACT TTA GGT GTT GAA GAG CTT GAA AAG TTA TTT AAA TCA GTA   480
Asp Lys Thr Leu Gly Val Glu Glu Leu Glu Lys Leu Phe Lys Ser Val
145                 150                 155                 160

GAA AAA TTG TCA AAA GCA GCG CAA GAA GCA CTA GCT AAT TCA GTT CAA   528
Glu Lys Leu Ser Lys Ala Ala Gln Glu Ala Leu Ala Asn Ser Val Gln
                165                 170                 175

GAG CTT ACA AGT CCT GTT GTG GCA GAA ACT CCA AAA AAA CCT TAA       573
Glu Leu Thr Ser Pro Val Val Ala Glu Thr Pro Lys Lys Pro
            180                 185                 190
```

(2) INFORMATION FOR SEQ ID NO: 34:

(i) SEQUENCE CHARACTERISTICS:
       (A) LENGTH: 190 amino acids
       (B) TYPE: amino acid
       (D) TOPOLOGY: linear (ii) MOLECULE TYPE: protein (xi) SEQUENCE DESCRIPTION: SEQ ID NO: 34:

```
Cys Asn Asn Ser Gly Gly Asp Thr Ala Ser Thr Asn Pro Asp Glu Ser
 1               5                  10                  15

Ala Lys Gly Pro Asp Leu Thr Val Ile Ser Lys Lys Ile Thr Asp Ser
            20                  25                  30

Asn Ala Phe Val Leu Ala Val Lys Glu Val Glu Ala Leu Leu Ser Ser
        35                  40                  45

Val Asp Glu Leu Ala Lys Ala Ile Gly Lys Lys Ile His Gln Asn Asn
 50                  55                  60

Gly Leu Asp Thr Leu Ser Asn Gln Asn Gly Ser Leu Leu Ala Gly Ala
 65                  70                  75                  80

Tyr Ala Ile Ser Thr Leu Ile Thr Lys Lys Leu Asp Gly Leu Lys Gly
                 85                  90                  95

Ser Glu Gly Leu Lys Ala Glu Ile Ala Glu Ala Lys Lys Cys Ser Glu
            100                 105                 110
```

```
Asp Phe Thr Lys Lys Leu Lys Glu Lys His Thr Glu Leu Gly Val Ala
        115                 120                 125

Ala Ala Thr Asp Asp Asn Ala Lys Lys Ala Ile Leu Lys Ala Asn Gly
    130                 135                 140

Asp Lys Thr Leu Gly Val Glu Glu Leu Glu Lys Leu Phe Lys Ser Val
145                 150                 155                 160

Glu Lys Leu Ser Lys Ala Ala Gln Glu Ala Leu Ala Asn Ser Val Gln
                165                 170                 175

Glu Leu Thr Ser Pro Val Val Ala Glu Thr Pro Lys Lys Pro
            180                 185                 190
```

(2) INFORMATION FOR SEQ ID NO: 35:

(i) SEQUENCE CHARACTERISTICS:
        (A) LENGTH: 582 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: NBS23a (ix) FEATURE:
        (A) NAME/KEY: CDS
        (B) LOCATION: 1..582

(xi) SEQUENCE DESCRIPTION: SEQ ID NO: 35:

```
TGT AAT AAT TCA GGT GGG GAT ACT GCA TCT ACT AAT CCT GAT GAG TCT     48
Cys Asn Asn Ser Gly Gly Asp Thr Ala Ser Thr Asn Pro Asp Glu Ser
  1               5                  10                  15

GCG AAA GGA CCT AAT CTT ACA GAA ATA AGC AAA AAA ATT ACA GAT TCT     96
Ala Lys Gly Pro Asn Leu Thr Glu Ile Ser Lys Lys Ile Thr Asp Ser
                 20                  25                  30

AAT GCA TTT GTA CTC GCC GTT AAA GAA GTT GAG GCT TTG ATT TCA TCT    144
Asn Ala Phe Val Leu Ala Val Lys Glu Val Glu Ala Leu Ile Ser Ser
             35                  40                  45

GTA GAT GAA CTT GCT AAG GCT ATT GGT AAA AAA ATA GAT AAC AAT ACT    192
Val Asp Glu Leu Ala Lys Ala Ile Gly Lys Lys Ile Asp Asn Asn Thr
         50                  55                  60

GGT TTA AGT GCT AAT CAG AAT CAT AAC ACT TCA TTG TTA GCA GGA GCC    240
Gly Leu Ser Ala Asn Gln Asn His Asn Thr Ser Leu Leu Ala Gly Ala
 65                  70                  75                  80

TAT TCA ATA TCA ACC CTA ATA ACA GAA AAA TTA AGT AAA TTA AAA AAT    288
Tyr Ser Ile Ser Thr Leu Ile Thr Glu Lys Leu Ser Lys Leu Lys Asn
                 85                  90                  95

TTA GAA GGG TTA AAA GCA GAG ATT GCA GAA GCT AAG AAA TGT TCT GAA    336
Leu Glu Gly Leu Lys Ala Glu Ile Ala Glu Ala Lys Lys Cys Ser Glu
            100                 105                 110

GAC TTT ACT AAA AAA CTA AAG GAT AAT CAT GCA GAT CTT GGA GTG GCG    384
Asp Phe Thr Lys Lys Leu Lys Asp Asn His Ala Asp Leu Gly Val Ala
        115                 120                 125

GGG AAT GGA GCT TCT ACT GAT GAA AAT GCA CAG AAA GCT ATT TTA AAA    432
Gly Asn Gly Ala Ser Thr Asp Glu Asn Ala Gln Lys Ala Ile Leu Lys
    130                 135                 140

ACA AAT GCG ATT GTC GAT AAG GGT GCT AAA GAC CTT AAA GAG TTA TTT    480
Thr Asn Ala Ile Val Asp Lys Gly Ala Lys Asp Leu Lys Glu Leu Phe
145                 150                 155                 160

GAA TCA GTA GAA AAA TTG TCA AAA GCA GCG CAA GAA GCA CTA GCT AAT    528
Glu Ser Val Glu Lys Leu Ser Lys Ala Ala Gln Glu Ala Leu Ala Asn
```

-continued

```
                           165                 170                 175
TCA GTT AAA GAG CTT ACA AGT CCT GTT GTG GCA GAA ACT CCA AAA AAA        576
Ser Val Lys Glu Leu Thr Ser Pro Val Val Ala Glu Thr Pro Lys Lys
            180                 185                 190

CCT TAA                                                                582
Pro
```

(2) INFORMATION FOR SEQ ID NO: 36:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 36:

```
Cys Asn Asn Ser Gly Gly Asp Thr Ala Ser Thr Asn Pro Asp Glu Ser
 1               5                  10                  15

Ala Lys Gly Pro Asn Leu Thr Glu Ile Ser Lys Lys Ile Thr Asp Ser
            20                  25                  30

Asn Ala Phe Val Leu Ala Val Lys Glu Val Glu Ala Leu Ile Ser Ser
        35                  40                  45

Val Asp Glu Leu Ala Lys Ala Ile Gly Lys Lys Ile Asp Asn Asn Thr
    50                  55                  60

Gly Leu Ser Ala Asn Gln Asn His Asn Thr Ser Leu Leu Ala Gly Ala
65                  70                  75                  80

Tyr Ser Ile Ser Thr Leu Ile Thr Glu Lys Leu Ser Lys Leu Lys Asn
                85                  90                  95

Leu Glu Gly Leu Lys Ala Glu Ile Ala Glu Ala Lys Lys Cys Ser Glu
            100                 105                 110

Asp Phe Thr Lys Lys Leu Lys Asp Asn His Ala Asp Leu Gly Val Ala
            115                 120                 125

Gly Asn Gly Ala Ser Thr Asp Glu Asn Ala Gln Lys Ala Ile Leu Lys
        130                 135                 140

Thr Asn Ala Ile Val Asp Lys Gly Ala Lys Asp Leu Lys Glu Leu Phe
145                 150                 155                 160

Glu Ser Val Glu Lys Leu Ser Lys Ala Ala Gln Glu Ala Leu Ala Asn
                165                 170                 175

Ser Val Lys Glu Leu Thr Ser Pro Val Val Ala Glu Thr Pro Lys Lys
            180                 185                 190

Pro
```

(2) INFORMATION FOR SEQ ID NO: 37:

(i) SEQUENCE CHARACTERISTICS:
        (A) LENGTH: 576 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: 20047

(ix) FEATURE:
        (A) NAME/KEY: CDS
        (B) LOCATION: 1..576

(xi) SEQUENCE DESCRIPTION: SEQ ID NO: 37:

```
TGT AAT AAT TCA GGT GGG GAT ACT GCA TCT ACT AAT CCT GAT GAA TCT        48
Cys Asn Asn Ser Gly Gly Asp Thr Ala Ser Thr Asn Pro Asp Glu Ser
 1               5                  10                  15

GTT AAG GGG CCT AAT CTT ACA GAA ATA AGC AAA AAA ATT ACA GAT TCT        96
Val Lys Gly Pro Asn Leu Thr Glu Ile Ser Lys Lys Ile Thr Asp Ser
                20                  25                  30

AAT GCA TTT GTA CTG GCT GTG AAA GAA GTT GAG GCT TTG ATC TCA TCT       144
Asn Ala Phe Val Leu Ala Val Lys Glu Val Glu Ala Leu Ile Ser Ser
            35                  40                  45

ATA GAT GAA CTT GCT AAA GCT ATT GGT CAA AGA ATA CAA CAA AAT GGT       192
Ile Asp Glu Leu Ala Lys Ala Ile Gly Gln Arg Ile Gln Gln Asn Gly
        50                  55                  60

TTA GTT GCT GAT GCG GGT CAC AAC AGC GCA TTG TTA GCA GGA GCC CAT       240
Leu Val Ala Asp Ala Gly His Asn Ser Ala Leu Leu Ala Gly Ala His
 65                  70                  75                  80

GAA ATA TCA ATC CTA ATA ACA CAA AAA TTA GAT GGA TTA AAA GGT TTA       288
Glu Ile Ser Ile Leu Ile Thr Gln Lys Leu Asp Gly Leu Lys Gly Leu
                85                  90                  95

GAA GGA TTA AAA GCA GAG ATT GCA GAA GCT AAG AAA TAT TCT GAA GCA       336
Glu Gly Leu Lys Ala Glu Ile Ala Glu Ala Lys Lys Tyr Ser Glu Ala
               100                 105                 110

TTT ACT AAA AAA CTA AAA GAT AAT CAT GCA CAG CTT GGT ATA CAG AAT       384
Phe Thr Lys Lys Leu Lys Asp Asn His Ala Gln Leu Gly Ile Gln Asn
           115                 120                 125

GGT GCT TCT CTT GAT GAT GAG GCA AAA AAA GCT ATT TTA AAA ACA AAT       432
Gly Ala Ser Leu Asp Asp Glu Ala Lys Lys Ala Ile Leu Lys Thr Asn
       130                 135                 140

GTG GAC AAA ACC AAG GGT GCT GAA GAG CTT GAA AAG TTA TTT AAA TCA       480
Val Asp Lys Thr Lys Gly Ala Glu Glu Leu Glu Lys Leu Phe Lys Ser
145                 150                 155                 160

GTA GAA AGC TTG TCA AAA GCA GCG CAA GAA GCA CTA ACT AAT TCA GTT       528
Val Glu Ser Leu Ser Lys Ala Ala Gln Glu Ala Leu Thr Asn Ser Val
                   165                 170                 175

AAA GAG CTT ACA AAT CCT GTT GTG GCA GAA ACT CCA AAA AAA CCT TAA      576
Lys Glu Leu Thr Asn Pro Val Val Ala Glu Thr Pro Lys Lys Pro
               180                 185                 190
```

(2) INFORMATION FOR SEQ ID NO: 38:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 38:

```
Cys Asn Asn Ser Gly Gly Asp Thr Ala Ser Thr Asn Pro Asp Glu Ser
 1               5                  10                  15

Val Lys Gly Pro Asn Leu Thr Glu Ile Ser Lys Lys Ile Thr Asp Ser
                20                  25                  30

Asn Ala Phe Val Leu Ala Val Lys Glu Val Glu Ala Leu Ile Ser Ser
            35                  40                  45

Ile Asp Glu Leu Ala Lys Ala Ile Gly Gln Arg Ile Gln Gln Asn Gly
        50                  55                  60

Leu Val Ala Asp Ala Gly His Asn Ser Ala Leu Leu Ala Gly Ala His
 65                  70                  75                  80

Glu Ile Ser Ile Leu Ile Thr Gln Lys Leu Asp Gly Leu Lys Gly Leu
                85                  90                  95
```

-continued

```
Glu Gly Leu Lys Ala Glu Ile Ala Glu Ala Lys Lys Tyr Ser Glu Ala
            100                 105                 110

-continued

```
GAA TCA GTA AAA AGT TTG CTA AAA GCA GCG CAA GCA GCA TTA AGC AAT      528
Glu Ser Val Lys Ser Leu Leu Lys Ala Ala Gln Ala Ala Leu Ser Asn
            165                 170                 175

TCA GTT AAA GAG CTT ACA AGT CCT GTT GTG GCA GAA GCT CCA AAA AAA      576
Ser Val Lys Glu Leu Thr Ser Pro Val Val Ala Glu Ala Pro Lys Lys
        180                 185                 190

CCT TAA                                                              582
Pro
```

(2) INFORMATION FOR SEQ ID NO: 40:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 40:

```
Cys Asn Asn Ser Gly Gly Asp Thr Ala Ser Thr Asn Pro Asp Glu Ser
  1               5                  10                  15

Ala Lys Gly Pro Asn Leu Ile Glu Ile Ser Lys Lys Ile Thr Asp Ser
             20                  25                  30

Asn Ala Phe Val Leu Ala Val Lys Glu Val Glu Ala Leu Leu Ser Ser
         35                  40                  45

Ile Asp Glu Leu Ala Lys Gly Ile Gly Lys Lys Ile Asp Gln Asn Ser
     50                  55                  60

Gly Leu Ala Ala Ala Thr Gln Asn Lys Asn Thr Ser Leu Leu Ala Gly
 65                  70                  75                  80

Ala Tyr Ala Val Ser Ala Leu Ile Lys Gln Lys Leu Asp Gly Leu Gln
                 85                  90                  95

Gly Pro Glu Gly Leu Asn Lys Glu Ile Glu Ala Ala Lys Lys Cys Ser
            100                 105                 110

Glu Ala Phe Thr Asn Lys Leu Lys Glu Lys His Ala Glu Leu Gly Val
        115                 120                 125

Asn Gly Gly Asp Thr Thr Asp Asp Asn Ala Lys Ala Ala Ile Phe Lys
    130                 135                 140

Thr His Pro Thr Lys Asp Lys Gly Val Glu Asp Leu Glu Lys Leu Ser
145                 150                 155                 160

Glu Ser Val Lys Ser Leu Leu Lys Ala Ala Gln Ala Ala Leu Ser Asn
                165                 170                 175

Ser Val Lys Glu Leu Thr Ser Pro Val Val Ala Glu Ala Pro Lys Lys
            180                 185                 190

Pro
```

(2) INFORMATION FOR SEQ ID NO: 41:

(i) SEQUENCE CHARACTERISTICS:
        (A) LENGTH: 531 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: IP90

(ix) FEATURE:
        (A) NAME/KEY: CDS
        (B) LOCATION: 1..531

(xi) SEQUENCE DESCRIPTION: SEQ ID NO: 41:

```
TGT AAT AAT TCA GGT GGG GAT AGT GCA TCT ACT AAT CCT GAT GAG TCT        48
Cys Asn Asn Ser Gly Gly Asp Ser Ala Ser Thr Asn Pro Asp Glu Ser
 1               5                  10                  15

GCG AAA GGA CCT GAT CTT ACA GTA ATA AGC AAA AAA ATT ACA GAT TCT        96
Ala Lys Gly Pro Asp Leu Thr Val Ile Ser Lys Lys Ile Thr Asp Ser
                20                  25                  30

AAT GCA TTT GTA CTG GCT GTG AAA GAA GTT GAG GCT TTG CTT TCA TCT       144
Asn Ala Phe Val Leu Ala Val Lys Glu Val Glu Ala Leu Leu Ser Ser
            35                  40                  45

ATA GAT GAA CTT GCT AAA GCT ATT GGT CAA AAA ATA GAT CAA AAT AAT       192
Ile Asp Glu Leu Ala Lys Ala Ile Gly Gln Lys Ile Asp Gln Asn Asn
 50                  55                  60

GGT TTA GCT GCT GCT ACT CAG GAT AAA AAC ACC TCA TTG TTA GCA GGA       240
Gly Leu Ala Ala Ala Thr Gln Asp Lys Asn Thr Ser Leu Leu Ala Gly
 65                  70                  75                  80

GCC TAT GCA ATA TCA GCC CTA ATA AAA CAA AAA TTA GAT GGA TTG CAA       288
Ala Tyr Ala Ile Ser Ala Leu Ile Lys Gln Lys Leu Asp Gly Leu Gln
                85                  90                  95

GGT CCA GAA GGG TTA AAT AAA GAA ATT GAA GCG GCT AAG AAA TGT TCT       336
Gly Pro Glu Gly Leu Asn Lys Glu Ile Glu Ala Ala Lys Lys Cys Ser
                100                 105                 110

GAA GCA TTT ACT AAT AAA TTA AAA GAG AAG CAC CAA GAC CTT GGA GTG       384
Glu Ala Phe Thr Asn Lys Leu Lys Glu Lys His Gln Asp Leu Gly Val
            115                 120                 125

GCG AAT GGT GAT ACT ACT GAT AAT AAT GCA AAA GCA GCT ATT TTA AAA       432
Ala Asn Gly Asp Thr Thr Asp Asn Asn Ala Lys Ala Ala Ile Leu Lys
130                 135                 140

ACA CAT GGG ACT GAG GAC AAG GGT GTT AAA GAA CTT AAA GAT TTG TTG       480
Thr His Gly Thr Glu Asp Lys Gly Val Lys Glu Leu Lys Asp Leu Leu
145                 150                 155                 160

AAA TCA GTA GAA AGC TTG GCA AAA GCA GCG CAA GCA GCA TCA AGC AAT       528
Lys Ser Val Glu Ser Leu Ala Lys Ala Ala Gln Ala Ala Ser Ser Asn
                165                 170                 175

TCA                                                                   531
Ser
```

(2) INFORMATION FOR SEQ ID NO: 42:

(i) SEQUENCE CHARACTERISTICS:
        (A) LENGTH: 177 amino acids
        (B) TYPE: amino acid
        (D) TOPOLOGY: linear (ii) MOLECULE TYPE: protein (xi) SEQUENCE DESCRIPTION: SEQ ID NO: 42:

```
Cys Asn Asn Ser Gly Gly Asp Ser Ala Ser Thr Asn Pro Asp Glu Ser
 1               5                  10                  15

Ala Lys Gly Pro Asp Leu Thr Val Ile Ser Lys Lys Ile Thr Asp Ser
                20                  25                  30

Asn Ala Phe Val Leu Ala Val Lys Glu Val Glu Ala Leu Leu Ser Ser
            35                  40                  45

Ile Asp Glu Leu Ala Lys Ala Ile Gly Gln Lys Ile Asp Gln Asn Asn
 50                  55                  60

Gly Leu Ala Ala Ala Thr Gln Asp Lys Asn Thr Ser Leu Leu Ala Gly
 65                  70                  75                  80

Ala Tyr Ala Ile Ser Ala Leu Ile Lys Gln Lys Leu Asp Gly Leu Gln
                85                  90                  95
```

```
Gly Pro Glu Gly Leu Asn Lys Glu Ile Glu Ala Ala Lys Lys Cys Ser
            100                 105                 110

Glu Ala Phe Thr Asn Lys Leu Lys Glu Lys His Gln Asp Leu Gly Val
            115                 120                 125

Ala Asn Gly Asp Thr Thr Asp Asn Asn Ala Lys Ala Ala Ile Leu Lys
            130                 135                 140

Thr His Gly Thr Glu Asp Lys Gly Val Lys Glu Leu Lys Asp Leu Leu
145                 150                 155                 160

Lys Ser Val Glu Ser Leu Ala Lys Ala Ala Gln Ala Ala Ser Ser Asn
                165                 170                 175

Ser (2) INFORMATION FOR SEQ ID NO: 43:

(i) SEQUENCE CHARACTERISTICS:
        (A) LENGTH: 531 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: NBS1AB (ix) FEATURE:
        (A) NAME/KEY: CDS
        (B) LOCATION: 1..531

(xi) SEQUENCE DESCRIPTION: SEQ ID NO: 43:

TGT AAT AAT TCA GGT GGG GAT ACT GCA TCT ACT AAT CCT GAT GAG TCT        48
Cys Asn Asn Ser Gly Gly Asp Thr Ala Ser Thr Asn Pro Asp Glu Ser
 1               5                  10                  15

GCA AAA GGA CCT AAT CTT ATA GAA ATA AGC AAA AAA ATT ACA GAT TCT        96
Ala Lys Gly Pro Asn Leu Ile Glu Ile Ser Lys Lys Ile Thr Asp Ser
                20                  25                  30

AAT GCA TTT GTA CTG GCT GTG AAA GAA GTT GAG GCT TTG CTT TCA TCT       144
Asn Ala Phe Val Leu Ala Val Lys Glu Val Glu Ala Leu Leu Ser Ser
            35                  40                  45

ATA GAT GAA CTT GCT AAA GCT ATT GGT CAA AAA ATA GAT CAA AAT AAT       192
Ile Asp Glu Leu Ala Lys Ala Ile Gly Gln Lys Ile Asp Gln Asn Asn
 50                  55                  60

GGT TTA GCT GCT GCT ACT CAG GAT AAA AAC ACC TCA TTG TTA GCA GGA       240
Gly Leu Ala Ala Ala Thr Gln Asp Lys Asn Thr Ser Leu Leu Ala Gly
 65                  70                  75                  80

GCC TAT GCA ATA TCA GCT CTA ATA AAA CAA AAA TTA GAT GGA TTG CAA       288
Ala Tyr Ala Ile Ser Ala Leu Ile Lys Gln Lys Leu Asp Gly Leu Gln
                 85                  90                  95

GGT CCA GAA GGG TTA AAT AAA GAA ATT GAA GCG GCT AAG AAA TGT TCT       336
Gly Pro Glu Gly Leu Asn Lys Glu Ile Glu Ala Ala Lys Lys Cys Ser
            100                 105                 110

GAA GCA TTT ACT AAT AAA TTA AAA GAG AAG CAC CAA GAC CTT GGA GTG       384
Glu Ala Phe Thr Asn Lys Leu Lys Glu Lys His Gln Asp Leu Gly Val
            115                 120                 125

GCG AAT GGT GAT ACT ACT GAT AAT AAT GCA AAA GCA GCT ATT TTA AAA       432
Ala Asn Gly Asp Thr Thr Asp Asn Asn Ala Lys Ala Ala Ile Leu Lys
            130                 135                 140

ACA CAT GGG ACT GAG GAC AAG GGT GTT AAA GAA CTT AAA GAT TTG TTG       480
Thr His Gly Thr Glu Asp Lys Gly Val Lys Glu Leu Lys Asp Leu Leu
145                 150                 155                 160
```

```
AAA TCA GTA GAA AGC TTG GCA AAA GCA GCG CAA GCA GCA TCA AGC AAT      528
Lys Ser Val Glu Ser Leu Ala Lys Ala Ala Gln Ala Ala Ser Ser Asn
            165                 170                 175

TCA                                                                   531
Ser (2) INFORMATION FOR SEQ ID NO: 44:

(i) SEQUENCE CHARACTERISTICS:
        (A) LENGTH: 177 amino acids
        (B) TYPE: amino acid
        (D) TOPOLOGY: linear (ii) MOLECULE TYPE: protein (xi) SEQUENCE DESCRIPTION: SEQ ID NO: 44:

Cys Asn Asn Ser Gly Gly Asp Thr Ala Ser Thr Asn Pro Asp Glu Ser
 1               5                  10                  15

Ala Lys Gly Pro Asn Leu Ile Glu Ile Ser Lys Lys Ile Thr Asp Ser
                20                  25                  30

Asn Ala Phe Val Leu Ala Val Lys Glu Val Glu Ala Leu Leu Ser Ser
            35                  40                  45

Ile Asp Glu Leu Ala Lys Ala Ile Gly Gln Lys Ile Asp Gln Asn Asn
 50                  55                  60

Gly Leu Ala Ala Ala Thr Gln Asp Lys Asn Thr Ser Leu Leu Ala Gly
 65                  70                  75                  80

Ala Tyr Ala Ile Ser Ala Leu Ile Lys Gln Lys Leu Asp Gly Leu Gln
                85                  90                  95

Gly Pro Glu Gly Leu Asn Lys Glu Ile Glu Ala Ala Lys Lys Cys Ser
               100                 105                 110

Glu Ala Phe Thr Asn Lys Leu Lys Glu Lys His Gln Asp Leu Gly Val
            115                 120                 125

Ala Asn Gly Asp Thr Thr Asp Asn Asn Ala Lys Ala Ala Ile Leu Lys
        130                 135                 140

Thr His Gly Thr Glu Asp Lys Gly Val Lys Glu Leu Lys Asp Leu Leu
145                 150                 155                 160

Lys Ser Val Glu Ser Leu Ala Lys Ala Ala Gln Ala Ala Ser Ser Asn
                165                 170                 175

Ser (2) INFORMATION FOR SEQ ID NO: 45:

(i) SEQUENCE CHARACTERISTICS:
        (A) LENGTH: 582 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: BITS (ix) FEATURE:
        (A) NAME/KEY: CDS
        (B) LOCATION: 1..582

(xi) SEQUENCE DESCRIPTION: SEQ ID NO: 45:

TGT AAT AAT TCA GGT GGA GAT TCT GCA TCT ACT AAT CCT GAT GAG TCT       48
Cys Asn Asn Ser Gly Gly Asp Ser Ala Ser Thr Asn Pro Asp Glu Ser
 1               5                  10                  15
```

```
GCA AAA GGA CCT GAT CTT ACA GTA ATA AGC AAA AAA ATT ACA GAT TCT        96
Ala Lys Gly Pro Asp Leu Thr Val Ile Ser Lys Lys Ile Thr Asp Ser
             20                  25                  30

AAT GCA GTT GTA CTG GCT GTG AAA GAA GTT GAA GCT TTG CTT TCA TCT       144
Asn Ala Val Val Leu Ala Val Lys Glu Val Glu Ala Leu Leu Ser Ser
         35                  40                  45

ATA GAT GAA CTT GCT AAA GCT ATT GGT CAA AAA ATA GAT CGA AAT AAT       192
Ile Asp Glu Leu Ala Lys Ala Ile Gly Gln Lys Ile Asp Arg Asn Asn
 50                  55                  60

GGT TTA GCT GTC GAA GCG AAT TTT AAC ACC TCA TTG TTA GCA GGA GCC       240
Gly Leu Ala Val Glu Ala Asn Phe Asn Thr Ser Leu Leu Ala Gly Ala
 65                  70                  75                  80

TAT ACA ATA TCA ACC CTA ATA ACA AAA AAA TTA GAT GAA TTG ATC AAA       288
Tyr Thr Ile Ser Thr Leu Ile Thr Lys Lys Leu Asp Glu Leu Ile Lys
                 85                  90                  95

AAT TCA GGA GAA TTA AAA GGA GAA GTT GAA AAG GCT AAA AAC TGT TCT       336
Asn Ser Gly Glu Leu Lys Gly Glu Val Glu Lys Ala Lys Asn Cys Ser
            100                 105                 110

GAA GCA TTT ACT AAT AAA TTA AAA GAG AAG ACC CAA GAA CTT GCA GTG       384
Glu Ala Phe Thr Asn Lys Leu Lys Glu Lys Thr Gln Glu Leu Ala Val
        115                 120                 125

GCG GCT GGT GCT GCT ACT GAT ATT GAT GCA AAA AAA GCT ATT TTA AAA       432
Ala Ala Gly Ala Ala Thr Asp Ile Asp Ala Lys Lys Ala Ile Leu Lys
130                 135                 140

ACA AAT AGG GAC AAG GAC CTA GGT GCT GAT GAA CTT GGC AAG TTA TTT       480
Thr Asn Arg Asp Lys Asp Leu Gly Ala Asp Glu Leu Gly Lys Leu Phe
145                 150                 155                 160

AAA TCA GTA GAA AGC TTG TCA AAA GCA GCG CAA GAA GCA TCA GCT AAT       528
Lys Ser Val Glu Ser Leu Ser Lys Ala Ala Gln Glu Ala Ser Ala Asn
                165                 170                 175

TCA GTT AAA GAG CTT ACA AGT CCT GTT GTG GCA GAA ACT CCA AAA AAA       576
Ser Val Lys Glu Leu Thr Ser Pro Val Val Ala Glu Thr Pro Lys Lys
            180                 185                 190

CCT TAA                                                               582
Pro (2) INFORMATION FOR SEQ ID NO: 46:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 46:

Cys Asn Asn Ser Gly Gly Asp Ser Ala Ser Thr Asn Pro Asp Glu Ser
 1               5                  10                  15

Ala Lys Gly Pro Asp Leu Thr Val Ile Ser Lys Lys Ile Thr Asp Ser
             20                  25                  30

Asn Ala Val Val Leu Ala Val Lys Glu Val Glu Ala Leu Leu Ser Ser
         35                  40                  45

Ile Asp Glu Leu Ala Lys Ala Ile Gly Gln Lys Ile Asp Arg Asn Asn
 50                  55                  60

Gly Leu Ala Val Glu Ala Asn Phe Asn Thr Ser Leu Leu Ala Gly Ala
 65                  70                  75                  80

Tyr Thr Ile Ser Thr Leu Ile Thr Lys Lys Leu Asp Glu Leu Ile Lys
                 85                  90                  95

Asn Ser Gly Glu Leu Lys Gly Glu Val Glu Lys Ala Lys Asn Cys Ser
            100                 105                 110
```

```
Glu Ala Phe Thr Asn Lys Leu Lys Glu Lys Thr Gln Glu Leu Ala Val
        115                 120                 125

Ala Ala Gly Ala Ala Thr Asp Ile Asp Ala Lys Lys Ala Ile Leu Lys
    130                 135                 140

Thr Asn Arg Asp Lys Asp Leu Gly Ala Asp Glu Leu Gly Lys Leu Phe
145                 150                 155                 160

Lys Ser Val Glu Ser Leu Ser Lys Ala Ala Gln Glu Ala Ser Ala Asn
                165                 170                 175

Ser Val Lys Glu Leu Thr Ser Pro Val Val Ala Glu Thr Pro Lys Lys
            180                 185                 190

Pro (2) INFORMATION FOR SEQ ID NO: 47:

(i) SEQUENCE CHARACTERISTICS:
        (A) LENGTH: 570 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: KL11

(ix) FEATURE:
        (A) NAME/KEY: CDS
        (B) LOCATION: 1..570

(xi) SEQUENCE DESCRIPTION: SEQ ID NO: 47:

TGT AAT AAT TCA GGT GGG GAT ACT GCA TCT ACT AAT CCT GAT GAA TCT        48
Cys Asn Asn Ser Gly Gly Asp Thr Ala Ser Thr Asn Pro Asp Glu Ser
  1               5                  10                  15

GCG AAA GGA CCT GAT CTT ACA GTA ATA AGC AAA AAA ATT ACA GAT TCT        96
Ala Lys Gly Pro Asp Leu Thr Val Ile Ser Lys Lys Ile Thr Asp Ser
                 20                  25                  30

AAT GCA GTT GTA CTG GTT GTG AAA GAA GTT GAG GCT TTG CTT TCA TCT       144
Asn Ala Val Val Leu Val Val Lys Glu Val Glu Ala Leu Leu Ser Ser
             35                  40                  45

ATA GAT GAA CTT TCT AAA GCT ATT GGT AAA AAA ATA AGA AAT GAT GGT       192
Ile Asp Glu Leu Ser Lys Ala Ile Gly Lys Lys Ile Arg Asn Asp Gly
 50                  55                  60

ACT TTA GAT AAC GAA GCA AAT CGA AAC GAA TCA TTG ATA GCA GGA GCT       240
Thr Leu Asp Asn Glu Ala Asn Arg Asn Glu Ser Leu Ile Ala Gly Ala
 65                  70                  75                  80

TAT GAA ATA TCA AAA CTA ATA ACA CAA AAA TTA AGT GTA TTG AAT TCA       288
Tyr Glu Ile Ser Lys Leu Ile Thr Gln Lys Leu Ser Val Leu Asn Ser
                 85                  90                  95

GAA GAA TTA AAG GAA AAA ATT AAA GAG GCT AAG GAT TGT TCC GAA AAA       336
Glu Glu Leu Lys Glu Lys Ile Lys Glu Ala Lys Asp Cys Ser Glu Lys
            100                 105                 110

TTT ACT ACT AAG CTG AGA GAT AGT CAT GCA GAG CTT GGT ATA CAA AAC       384
Phe Thr Thr Lys Leu Arg Asp Ser His Ala Glu Leu Gly Ile Gln Asn
        115                 120                 125

GTT CAG GAT GAT AAT GCA AAA AGA GCT ATT TTA AAA ACA CAT GGG AAT       432
Val Gln Asp Asp Asn Ala Lys Arg Ala Ile Leu Lys Thr His Gly Asn
    130                 135                 140

AAA GAC AAG GGT GCT AAA GAA CTT AAA GAG TTA TCT GAA TCA TTA GAA       480
Lys Asp Lys Gly Ala Lys Glu Leu Lys Glu Leu Ser Glu Ser Leu Glu
145                 150                 155                 160
```

```
AAA TTG TCA AAA GCA GCG CAA GCA GCA CTA GCT AAT TCA GTT AAA GAG      528
Lys Leu Ser Lys Ala Ala Gln Ala Ala Leu Ala Asn Ser Val Lys Glu
            165                 170                 175

CTT ACA AGT CCT GTT GTG GCA GAA ACT CCA AAA AAA CCT TAA              570
Leu Thr Ser Pro Val Val Ala Glu Thr Pro Lys Lys Pro
            180                 185                 190
```

(2) INFORMATION FOR SEQ ID NO: 48:

(i) SEQUENCE CHARACTERISTICS:
        (A) LENGTH: 189 amino acids
        (B) TYPE: amino acid
        (D) TOPOLOGY: linear (ii) MOLECULE TYPE: protein (xi) SEQUENCE DESCRIPTION: SEQ ID NO: 48:

```
Cys Asn Asn Ser Gly Gly Asp Thr Ala Ser Thr Asn Pro Asp Glu Ser
 1               5                  10                  15

Ala Lys Gly Pro Asp Leu Thr Val Ile Ser Lys Lys Ile Thr Asp Ser
            20                  25                  30

Asn Ala Val Val Leu Val Val Lys Glu Val Glu Ala Leu Leu Ser Ser
            35                  40                  45

Ile Asp Glu Leu Ser Lys Ala Ile Gly Lys Lys Ile Arg Asn Asp Gly
        50                  55                  60

Thr Leu Asp Asn Glu Ala Asn Arg Asn Glu Ser Leu Ile Ala Gly Ala
65                  70                  75                  80

Tyr Glu Ile Ser Lys Leu Ile Thr Gln Lys Leu Ser Val Leu Asn Ser
            85                  90                  95

Glu Glu Leu Lys Glu Lys Ile Lys Glu Ala Lys Asp Cys Ser Glu Lys
            100                 105                 110

Phe Thr Thr Lys Leu Arg Asp Ser His Ala Glu Leu Gly Ile Gln Asn
            115                 120                 125

Val Gln Asp Asp Asn Ala Lys Arg Ala Ile Leu Lys Thr His Gly Asn
        130                 135                 140

Lys Asp Lys Gly Ala Lys Glu Leu Lys Glu Leu Ser Glu Ser Leu Glu
145                 150                 155                 160

Lys Leu Ser Lys Ala Ala Gln Ala Ala Leu Ala Asn Ser Val Lys Glu
            165                 170                 175

Leu Thr Ser Pro Val Val Ala Glu Thr Pro Lys Lys Pro
            180                 185
```

(2) INFORMATION FOR SEQ ID NO: 49:

(i) SEQUENCE CHARACTERISTICS:
        (A) LENGTH: 519 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia garinii
        (B) STRAIN: PB1

(ix) FEATURE:
        (A) NAME/KEY: CDS
        (B) LOCATION: 1..519

(xi) SEQUENCE DESCRIPTION: SEQ ID NO: 49:

```
TGT AAT AAT TCA GGT GGG GAT TCT GCA TCT ACT AAT CCT GAT GAG TCT      48
Cys Asn Asn Ser Gly Gly Asp Ser Ala Ser Thr Asn Pro Asp Glu Ser
```

```
      1               5                  10                  15
GCA AAA GGA CCT AAT CTT ACC GTA ATA AGC AAA AAA ATT ACA GAT TCT        96
Ala Lys Gly Pro Asn Leu Thr Val Ile Ser Lys Lys Ile Thr Asp Ser
                 20                  25                  30

AAT GCA TTT TTA CTG GCT GTG AAA GAA GTT GAG GCT TTG CTT TCA TCT       144
Asn Ala Phe Leu Leu Ala Val Lys Glu Val Glu Ala Leu Leu Ser Ser
             35                  40                  45

ATA GAT GAA CTT TCT AAA GCT ATT GGT AAA AAA ATA AAA AAT GAT GGT       192
Ile Asp Glu Leu Ser Lys Ala Ile Gly Lys Lys Ile Lys Asn Asp Gly
     50                  55                  60

ACT TTA GAT AAC GAA GCA AAT CGA AAC GAA TCA TTG ATA GCA GGA GCT       240
Thr Leu Asp Asn Glu Ala Asn Arg Asn Glu Ser Leu Ile Ala Gly Ala
 65                  70                  75                  80

TAT GAA ATA TCA AAA CTA ATA ACA CAA AAA TTA AGT GTA TTG AAT TCA       288
Tyr Glu Ile Ser Lys Leu Ile Thr Gln Lys Leu Ser Val Leu Asn Ser
                 85                  90                  95

GAA GAA TTA AAG GAA AAA ATT AAA GAG GCT AAG GAT TGT TCC CAA AAA       336
Glu Glu Leu Lys Glu Lys Ile Lys Glu Ala Lys Asp Cys Ser Gln Lys
            100                 105                 110

TTT ACT ACT AAG CTA AAA GAT AGT CAT GCA GAG CTT GGT ATA CAA AGC       384
Phe Thr Thr Lys Leu Lys Asp Ser His Ala Glu Leu Gly Ile Gln Ser
        115                 120                 125

GTT CAG GAT GAT AAT GCA AAA AAA GCT ATT TTA AAA ACA CAT GGA ACT       432
Val Gln Asp Asp Asn Ala Lys Lys Ala Ile Leu Lys Thr His Gly Thr
    130                 135                 140

AAA GAC AAG GGT GCT AAA GAA CTT GAA GAG TTA TTT AAA TCA CTA GAA       480
Lys Asp Lys Gly Ala Lys Glu Leu Glu Glu Leu Phe Lys Ser Leu Glu
145                 150                 155                 160

AGC TTG TCA AAA GCA GCG CAA GCA GCA TTA ACT AAT TCA                   519
Ser Leu Ser Lys Ala Ala Gln Ala Ala Leu Thr Asn Ser
                165                 170
```

(2) INFORMATION FOR SEQ ID NO: 50:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO: 50:

```
Cys Asn Asn Ser Gly Gly Asp Ser Ala Ser Thr Asn Pro Asp Glu Ser
 1               5                  10                  15

Ala Lys Gly Pro Asn Leu Thr Val Ile Ser Lys Lys Ile Thr Asp Ser
                20                  25                  30

Asn Ala Phe Leu Leu Ala Val Lys Glu Val Glu Ala Leu Leu Ser Ser
            35                  40                  45

Ile Asp Glu Leu Ser Lys Ala Ile Gly Lys Lys Ile Lys Asn Asp Gly
    50                  55                  60

Thr Leu Asp Asn Glu Ala Asn Arg Asn Glu Ser Leu Ile Ala Gly Ala
 65                  70                  75                  80

Tyr Glu Ile Ser Lys Leu Ile Thr Gln Lys Leu Ser Val Leu Asn Ser
                85                  90                  95

Glu Glu Leu Lys Glu Lys Ile Lys Glu Ala Lys Asp Cys Ser Gln Lys
           100                 105                 110

Phe Thr Thr Lys Leu Lys Asp Ser His Ala Glu Leu Gly Ile Gln Ser
       115                 120                 125

Val Gln Asp Asp Asn Ala Lys Lys Ala Ile Leu Lys Thr His Gly Thr
```

```
         130                 135                 140
Lys Asp Lys Gly Ala Lys Glu Leu Glu Glu Leu Phe Lys Ser Leu Glu
145                 150                 155                 160

Ser Leu Ser Lys Ala Ala Gln Ala Ala Leu Thr Asn Ser
                165                 170
```

(2) INFORMATION FOR SEQ ID NO: 51:

(i) SEQUENCE CHARACTERISTICS:
        (A) LENGTH: 570 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Borrelia
        (B) STRAIN: H13

(ix) FEATURE:
        (A) NAME/KEY: CDS
        (B) LOCATION: 1..570

(xi) SEQUENCE DESCRIPTION: SEQ ID NO: 51:

```
TGT AAT AAT TCA GGT GGG GAT ACT GCA TCT ACT AAT CCT GAT GAG TCC      48
Cys Asn Asn Ser Gly Gly Asp Thr Ala Ser Thr Asn Pro Asp Glu Ser
  1               5                  10                  15

ACT AAA GGA CCT AAT CTT ATA GAA ATA AGC AAA AAA ATT ACA GAT TCC      96
Thr Lys Gly Pro Asn Leu Ile Glu Ile Ser Lys Lys Ile Thr Asp Ser
                 20                  25                  30

AAT GCA GTT GTA CTG GCT GTG AAA GAA GTT GAG GCT TTG ATC TCA TCT     144
Asn Ala Val Val Leu Ala Val Lys Glu Val Glu Ala Leu Ile Ser Ser
             35                  40                  45

ATA GAT GAA CTT GCT AAG GCT ATT GGT AAA AAA GTA GAG GCA AAT GGT     192
Ile Asp Glu Leu Ala Lys Ala Ile Gly Lys Lys Val Glu Ala Asn Gly
 50                  55                  60

TTG GGT AAC GAA GCG GAT AGA AAC ACC TCA TTG TTA GCA GGA GCT CAT     240
Leu Gly Asn Glu Ala Asp Arg Asn Thr Ser Leu Leu Ala Gly Ala His
 65                  70                  75                  80

GAA ATA TCA ATT CTA ATA ACA CAA AAA TTA ACT GCA TTA AAA GAT TCA     288
Glu Ile Ser Ile Leu Ile Thr Gln Lys Leu Thr Ala Leu Lys Asp Ser
                 85                  90                  95

GGA GGA TTA AAA GCA GAG ATT GCA GAA GCT AAG AAA TGT TCT GAA GCA     336
Gly Gly Leu Lys Ala Glu Ile Ala Glu Ala Lys Lys Cys Ser Glu Ala
             100                 105                 110

TTT ACT AAA AAA CTA AAA GAT AAT AAT GCA CAG CTT GGT ATA CAA AAC     384
Phe Thr Lys Lys Leu Lys Asp Asn Asn Ala Gln Leu Gly Ile Gln Asn
         115                 120                 125

GTT CAG GAT GTT GAG GCA AAA AAA GCT ATT TTA AAA ACA AAT GGG GAC     432
Val Gln Asp Val Glu Ala Lys Lys Ala Ile Leu Lys Thr Asn Gly Asp
     130                 135                 140

ATA AGC AAG GGT GCT AAA GAA CTT AAA GAG TTA TTT GAA TCA GTA GAA     480
Ile Ser Lys Gly Ala Lys Glu Leu Lys Glu Leu Phe Glu Ser Val Glu
145                 150                 155                 160

AGC TTG GCA AAA GCA GCG CAA GCA GCA CTA GCT AAT TCA GTT CAA GAG     528
Ser Leu Ala Lys Ala Ala Gln Ala Ala Leu Ala Asn Ser Val Gln Glu
                165                 170                 175

CTT ACA AGC CCT GTT GTG GCA GAA ACT CCA AAA AAA CCT TAA             570
Leu Thr Ser Pro Val Val Ala Glu Thr Pro Lys Lys Pro
            180                 185                 190
```

(2) INFORMATION FOR SEQ ID NO: 52:

(i) SEQUENCE CHARACTERISTICS:
    (A) LENGTH: 189 amino acids
    (B) TYPE: amino acid
    (D) TOPOLOGY: linear (ii) MOLECULE TYPE: protein (xi) SEQUENCE DESCRIPTION: SEQ ID NO: 52:

```
Cys Asn Asn Ser Gly Gly Asp Thr Ala Ser Thr Asn Pro Asp Glu Ser
 1               5                  10                  15

Thr Lys Gly Pro Asn Leu Ile Glu Ile Ser Lys Lys Ile Thr Asp Ser
            20                  25                  30

Asn Ala Val Val Leu Ala Val Lys Glu Val Glu Ala Leu Ile Ser Ser
        35                  40                  45

Ile Asp Glu Leu Ala Lys Ala Ile Gly Lys Lys Val Glu Ala Asn Gly
     50                  55                  60

Leu Gly Asn Glu Ala Asp Arg Asn Thr Ser Leu Leu Ala Gly Ala His
 65                  70                  75                  80

Glu Ile Ser Ile Leu Ile Thr Gln Lys Leu Thr Ala Leu Lys Asp Ser
                 85                  90                  95

Gly Gly Leu Lys Ala Glu Ile Ala Glu Ala Lys Lys Cys Ser Glu Ala
            100                 105                 110

Phe Thr Lys Lys Leu Lys Asp Asn Asn Ala Gln Leu Gly Ile Gln Asn
        115                 120                 125

Val Gln Asp Val Glu Ala Lys Lys Ala Ile Leu Lys Thr Asn Gly Asp
    130                 135                 140

Ile Ser Lys Gly Ala Lys Glu Leu Lys Glu Leu Phe Glu Ser Val Glu
145                 150                 155                 160

Ser Leu Ala Lys Ala Ala Gln Ala Ala Leu Ala Asn Ser Val Gln Glu
                165                 170                 175

Leu Thr Ser Pro Val Val Ala Glu Thr Pro Lys Lys Pro
            180                 185
```

(2) INFORMATION FOR SEQ ID NO: 53:

(i) SEQUENCE CHARACTERISTICS:
       (A) LENGTH: 528 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (A) ORGANISM: Borrelia burgdorfi
       (B) STRAIN: B31

(ix) FEATURE:
       (A) NAME/KEY: CDS
       (B) LOCATION: 1..528

(xi) SEQUENCE DESCRIPTION: SEQ ID NO: 53:

```
TGT AAT AAT TCA GGG AAA GAT GGG AAT ACA TCT GCA AAT TCT GCT GAT       48
Cys Asn Asn Ser Gly Lys Asp Gly Asn Thr Ser Ala Asn Ser Ala Asp
 1               5                  10                  15

GAG TCT GTT AAA GGG CCT AAT CTT ACA GAA ATA AGT AAA AAA ATT ACG       96
Glu Ser Val Lys Gly Pro Asn Leu Thr Glu Ile Ser Lys Lys Ile Thr
            20                  25                  30

GAT TCT AAT GCG GTT TTA CTT GCT GTG AAA GAG GTT GAA GCG TTG CTG      144
Asp Ser Asn Ala Val Leu Leu Ala Val Lys Glu Val Glu Ala Leu Leu
        35                  40                  45
```

```
TCA TCT ATA GAT GAA ATT GCT GCT AAA GCT ATT GGT AAA AAA ATA CAC      192
Ser Ser Ile Asp Glu Ile Ala Ala Lys Ala Ile Gly Lys Lys Ile His
    50                  55                  60

CAA AAT AAT GGT TTG GAT ACC GAA AAT AAT CAC AAT GGA TCA TTG TTA      240
Gln Asn Asn Gly Leu Asp Thr Glu Asn Asn His Asn Gly Ser Leu Leu
65                  70                  75                  80

GCG GGA GCT TAT GCA ATA TCA ACC CTA ATA AAA CAA AAA TTA GAT GGA      288
Ala Gly Ala Tyr Ala Ile Ser Thr Leu Ile Lys Gln Lys Leu Asp Gly
                    85                  90                  95

TTG AAA AAT GAA GGA TTA AAG GAA AAA ATT GAT GCG GCT AAG AAA TGT      336
Leu Lys Asn Glu Gly Leu Lys Glu Lys Ile Asp Ala Ala Lys Lys Cys
                100                 105                 110

TCT GAA ACA TTT ACT AAT AAA TTA AAA GAA AAA CAC ACA GAT CTT GGT      384
Ser Glu Thr Phe Thr Asn Lys Leu Lys Glu Lys His Thr Asp Leu Gly
            115                 120                 125

AAA GAA GGT GTT ACT GAT GCT GAT GCA AAA GAA GCC ATT TTA AAA ACA      432
Lys Glu Gly Val Thr Asp Ala Asp Ala Lys Glu Ala Ile Leu Lys Thr
130                 135                 140

AAT GGT ACT AAA ACT AAA GGT GCT GAA GAA CTT GGA AAA TTA TTT GAA      480
Asn Gly Thr Lys Thr Lys Gly Ala Glu Glu Leu Gly Lys Leu Phe Glu
145                 150                 155                 160

TCA GTA GAG GTC TTG TCA AAA GCA GCT AAA GAG ATG CTT GCT AAT TCA      528
Ser Val Glu Val Leu Ser Lys Ala Ala Lys Glu Met Leu Ala Asn Ser
                165                 170                 175
```

(2) INFORMATION FOR SEQ ID NO: 54:

(i) SEQUENCE CHARACTERISTICS:
      (A) LENGTH: 176 amino acids
      (B) TYPE: amino acid
      (D) TOPOLOGY: linear (ii) MOLECULE TYPE: protein (xi) SEQUENCE DESCRIPTION: SEQ ID NO: 54:

```
Cys Asn Asn Ser Gly Lys Asp Gly Asn Thr Ser Ala Asn Ser Ala Asp
1               5                   10                  15

Glu Ser Val Lys Gly Pro Asn Leu Thr Glu Ile Ser Lys Lys Ile Thr
                20                  25                  30

Asp Ser Asn Ala Val Leu Leu Ala Val Lys Glu Val Glu Ala Leu Leu
            35                  40                  45

Ser Ser Ile Asp Glu Ile Ala Ala Lys Ala Ile Gly Lys Lys Ile His
        50                  55                  60

Gln Asn Asn Gly Leu Asp Thr Glu Asn Asn His Asn Gly Ser Leu Leu
65                  70                  75                  80

Ala Gly Ala Tyr Ala Ile Ser Thr Leu Ile Lys Gln Lys Leu Asp Gly
                85                  90                  95

Leu Lys Asn Glu Gly Leu Lys Glu Lys Ile Asp Ala Ala Lys Lys Cys
                100                 105                 110

Ser Glu Thr Phe Thr Asn Lys Leu Lys Glu Lys His Thr Asp Leu Gly
            115                 120                 125

Lys Glu Gly Val Thr Asp Ala Asp Ala Lys Glu Ala Ile Leu Lys Thr
130                 135                 140

Asn Gly Thr Lys Thr Lys Gly Ala Glu Glu Leu Gly Lys Leu Phe Glu
145                 150                 155                 160

Ser Val Glu Val Leu Ser Lys Ala Ala Lys Glu Met Leu Ala Asn Ser
                165                 170                 175
```

(2) INFORMATION FOR SEQ ID NO: 55:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

ATGAAAAAGA ATACATTAAG TGC                                               23

(2) INFORMATION FOR SEQ ID NO: 56:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

TAATTAAGGT TTTTTTGGAG TTTCTG                                            26

(2) INFORMATION FOR SEQ ID NO: 57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

ATGAAAAAGA ATACATTAAG TGCG                                              24

(2) INFORMATION FOR SEQ ID NO: 58:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

ATTAAGGTTT TTTTGGAGTT TCTG                                              24

(2) INFORMATION FOR SEQ ID NO: 59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 59:

ATGAAAAAGA ATACATTAAG TGCG                                              24

(2) INFORMATION FOR SEQ ID NO: 60:

(i) SEQUENCE CHARACTERISTICS:
        (A) LENGTH: 24 base pairs
        (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO: 60:

ATTAAGGTTT TTTTGGAGTT TCTG                                         24

(2) INFORMATION FOR SEQ ID NO: 61:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 61:

AAATGTGTAA TAATTCAGGG AAAGG                                        25

(2) INFORMATION FOR SEQ ID NO: 62:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 62:

ATTAAGGTTT TTTTGGAGTT TCTG                                         24

(2) INFORMATION FOR SEQ ID NO: 63:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 63:

AAACGATGTG TAATAATTCA GGGAAAGG                                     28

(2) INFORMATION FOR SEQ ID NO: 64:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 64:

ATTAAGGTTT TTTTGGTTTC TG                                           22

(2) INFORMATION FOR SEQ ID NO: 65:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO: 65:

GGGACTTCGA AACGAATGTG TAATAATTCA GGTGGG                                       36

(2) INFORMATION FOR SEQ ID NO: 66:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 66:

GGAATTCATT AAGGTTTTTT TGGA                                                    24

(2) INFORMATION FOR SEQ ID NO: 67:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 67:

Val Lys Leu Ser Glu Ser Val Ala Ser Leu Ser Lys Ala Ala
1               5                   10

(2) INFORMATION FOR SEQ ID NO: 68:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 68:

Thr Asp Asn Asp Ser Lys Glu Ala Ile Leu Lys Thr Asn Gly Thr
1               5                   10                  15

(2) INFORMATION FOR SEQ ID NO: 69:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 69:

Lys Glu Leu Thr Ser Pro Val Val Ala Glu Thr Pro Lys Lys Pro
1               5                   10                  15

(2) INFORMATION FOR SEQ ID NO: 70:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 70:

Phe Val Leu Ala Val Lys Glu Val Glu Thr Leu
1               5                   10

(2) INFORMATION FOR SEQ ID NO: 71:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 71:

Tyr Ala Ile Ser Thr Leu Ile Thr Glu Lys Leu Lys Ala Leu
1               5                   10

(2) INFORMATION FOR SEQ ID NO: 72:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 72:

Pro Asn Leu Thr Glu Ile Ser Lys Lys Ile Thr Asp Ser Asn Ala
1               5                   10                  15

(2) INFORMATION FOR SEQ ID NO: 73:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 73:

Ala Ser Ala Asn Ser Val Lys Glu Leu Thr Ser Pro Val Val
1               5                   10

(2) INFORMATION FOR SEQ ID NO: 74:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 74:

Ser Pro Val Val Ala Glu Thr Pro Lys Lys Pro
1               5                   10

(2) INFORMATION FOR SEQ ID NO: 75:

-continued

```
     (i) SEQUENCE CHARACTERISTICS:
          (A) LENGTH: 12 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO: 75:

Gly Lys Lys Ile Gln Gln Asn Asn Gly Leu Gly Ala
1               5                   10

(2) INFORMATION FOR SEQ ID NO: 76:

(i) SEQUENCE CHARACTERISTICS:
          (A) LENGTH: 10 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO: 76:

Ser Pro Val Val Ala Glu Ser Pro Lys Lys
1               5                   10

(2) INFORMATION FOR SEQ ID NO: 77:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 77:

CGGACTTCGA AACGAATGTG TAATAATTCA GGGAAAG                                37
```